(12) United States Patent
Grossman et al.

(10) Patent No.: US 8,105,553 B2
(45) Date of Patent: Jan. 31, 2012

(54) CRYSTAL FORMING DEVICES AND SYSTEMS AND METHODS FOR USING THE SAME

(75) Inventors: Robert Grossman, South San Francisco, CA (US); Marc Unger, San Mateo, CA (US); Phillip Lam, San Francisco, CA (US); Hou-Pu Chou, Sunnyvale, CA (US); Jake Kimball, Oakland, CA (US); Martin Pieprzyk, Belmont, CA (US)

(73) Assignee: Fluidigm Corporation, South San Francisco, CA (US)

( * ) Notice: Subject to any disclaimer, the term of this patent is extended or adjusted under 35 U.S.C. 154(b) by 80 days.

(21) Appl. No.: 11/043,895

(22) Filed: Jan. 25, 2005

(65) Prior Publication Data

US 2005/0201901 A1 Sep. 15, 2005

Related U.S. Application Data

(60) Provisional application No. 60/558,316, filed on Mar. 30, 2004, provisional application No. 60/557,715, filed on Mar. 29, 2004, provisional application No. 60/539,283, filed on Jan. 25, 2004.

(51) Int. Cl.
*C12Q 1/68* (2006.01)
*G01N 15/06* (2006.01)
*G01N 33/00* (2006.01)
*G01N 33/48* (2006.01)
*G01N 35/00* (2006.01)

(52) U.S. Cl. ......... 422/504; 422/50; 422/68.1; 422/502; 436/43

(58) Field of Classification Search .......... 422/50, 422/68.1, 100, 502, 504; 436/43
See application file for complete search history.

(56) References Cited

U.S. PATENT DOCUMENTS 2,620,938 A 12/1952 Jesnig
(Continued)

FOREIGN PATENT DOCUMENTS

EP 0 553 539 4/1993
(Continued)

OTHER PUBLICATIONS

"Biochips," Nature Biotechnology, vol. 18, Supplement 2000, pp. IT43-IT44, 2000.
(Continued)

*Primary Examiner* — Jan Ludlow
(74) *Attorney, Agent, or Firm* — Kilpatrick Townsend & Stockton LLP

(57) ABSTRACT

The present invention provides for microfluidic devices and methods for their use. The invention further provides for apparatus and systems for using the microfluidic devices, analyze reactions carried out in the microfluidic devices, and systems to generate, store, organize, and analyze data generated from using the microfluidic devices. The invention further provides methods of using and making microfluidic systems and devices which, in some embodiments, are useful for crystal formation. In one embodiment, an apparatus includes a platen having a platen face with one or more fluid ports therein. The fluid ports spatially correspond to one or more wells on a surface of the microfluidic device. A platform for holding the microfluidic device relative to the platen is included, and a platen actuator for urging the platen against the microfluidic device so that at least one of the fluid ports of the platen is urged against one of the wells to form a pressure chamber comprising the well and the port, so that when pressurized fluid is introduced or removed into or from the pressure chamber through one of the ports, fluid pressure is changed therein.

12 Claims, 43 Drawing Sheets

U.S. PATENT DOCUMENTS

| | | |
|---|---|---|
| 3,495,608 A | 2/1970 | O'Keefe |
| 3,570,515 A | 3/1971 | Kinner |
| 3,747,628 A | 7/1973 | Holster et al. |
| 3,801,949 A | 4/1974 | Larrabee |
| 4,046,159 A | 9/1977 | Pegourie |
| 4,119,368 A | 10/1978 | Yamazaki |
| 4,153,855 A | 5/1979 | Feingold |
| 4,245,673 A | 1/1981 | Bouteille et al. |
| 4,434,704 A | 3/1984 | Surjaatmadja |
| 4,848,722 A | 7/1989 | Webster |
| 4,895,706 A * | 1/1990 | Root et al. ................ 422/102 |
| 4,898,582 A | 2/1990 | Faste |
| 4,948,564 A | 8/1990 | Root et al. |
| 4,992,312 A | 2/1991 | Frisch |
| 5,085,562 A | 2/1992 | Van Lintel |
| 5,088,515 A | 2/1992 | Kamen |
| 5,096,388 A | 3/1992 | Weinberg |
| 5,123,563 A | 6/1992 | Nottingham et al. |
| 5,126,115 A | 6/1992 | Fujita et al. |
| 5,164,558 A | 11/1992 | Huff et al. |
| 5,171,132 A | 12/1992 | Miyazaki |
| 5,224,843 A | 7/1993 | Van Lintel |
| 5,259,737 A | 11/1993 | Kamisuki et al. |
| 5,265,327 A | 11/1993 | Faris et al. |
| 5,290,240 A | 3/1994 | Horres, Jr. |
| 5,336,062 A | 8/1994 | Richter |
| 5,346,372 A | 9/1994 | Naruse et al. |
| 5,375,979 A | 12/1994 | Trah |
| 5,376,252 A | 12/1994 | Ekstrom |
| 5,400,741 A | 3/1995 | DeTitta et al. |
| 5,423,287 A | 6/1995 | Usami et al. |
| 5,496,517 A | 3/1996 | Pfost et al. |
| 5,529,465 A | 6/1996 | Zengerle et al. |
| 5,546,416 A | 8/1996 | Basu |
| 5,593,130 A | 1/1997 | Hansson et al. |
| 5,637,469 A | 6/1997 | Wilding et al. |
| 5,642,015 A | 6/1997 | Whitehead et al. |
| 5,659,171 A | 8/1997 | Young et al. |
| 5,660,370 A | 8/1997 | Webster |
| 5,681,024 A | 10/1997 | Lisec et al. |
| 5,705,018 A | 1/1998 | Hartley |
| 5,759,014 A | 6/1998 | Van Lintel |
| 5,775,371 A | 7/1998 | Pan et al. |
| 5,788,468 A | 8/1998 | Dewa et al. |
| 5,836,750 A | 11/1998 | Cabuz |
| 5,842,787 A | 12/1998 | Kopf-Sill et al. |
| 5,856,174 A | 1/1999 | Lipshutz et al. |
| 5,875,817 A | 3/1999 | Carter |
| 5,876,187 A | 3/1999 | Afromowitz et al. |
| 5,876,675 A | 3/1999 | Kennedy |
| 5,885,470 A | 3/1999 | Parce et al. |
| 5,928,880 A | 7/1999 | Wilding et al. |
| 5,932,100 A | 8/1999 | Yager et al. |
| 5,932,799 A | 8/1999 | Moles |
| 5,942,443 A | 8/1999 | Parce et al. |
| 5,958,694 A | 9/1999 | Nikiforov |
| 5,972,187 A | 10/1999 | Parce et al. |
| 6,007,309 A | 12/1999 | Hartley |
| 6,043,080 A | 3/2000 | Lipshutz et al. |
| 6,046,056 A | 4/2000 | Parce et al. |
| 6,096,271 A * | 8/2000 | Bogen et al. ................ 422/64 |
| 6,123,769 A | 9/2000 | Sanjoh |
| 6,143,496 A | 11/2000 | Brown et al. |
| 6,155,282 A | 12/2000 | Zachary et al. |
| 6,165,694 A | 12/2000 | Liu |
| 6,168,948 B1 | 1/2001 | Anderson et al. |
| 6,174,365 B1 | 1/2001 | Sanjoh |
| 6,174,675 B1 | 1/2001 | Chow et al. |
| 6,251,343 B1 | 6/2001 | Dubrow et al. |
| 6,268,131 B1 | 7/2001 | Kang et al. |
| 6,296,673 B1 | 10/2001 | Santarsiero et al. |
| 6,306,659 B1 | 10/2001 | Parce et al. |
| 6,345,502 B1 | 2/2002 | Tai et al. |
| 6,395,232 B1 | 5/2002 | McBride |
| 6,395,483 B1 | 5/2002 | Patil et al. |
| 6,408,878 B2 | 6/2002 | Unger et al. |
| 6,409,832 B2 | 6/2002 | Weigl et al. |
| 6,448,090 B1 | 9/2002 | McBride |
| 6,485,690 B1 * | 11/2002 | Pfost et al. ................ 422/102 |
| 6,503,757 B1 | 1/2003 | Chow |
| 6,582,969 B1 | 6/2003 | Wagner et al. |
| 6,585,939 B1 | 7/2003 | Dapprich |
| 6,602,714 B1 | 8/2003 | Tagge et al. |
| 6,664,104 B2 | 12/2003 | Pourahmadi et al. |
| 6,677,151 B2 | 1/2004 | Sandell |
| 6,719,840 B2 | 4/2004 | David et al. |
| 6,767,706 B2 | 7/2004 | Quake et al. |
| 6,793,753 B2 | 9/2004 | Unger et al. |
| 6,797,056 B2 | 9/2004 | David |
| 6,814,934 B1 | 11/2004 | Higuchi |
| 6,893,879 B2 | 5/2005 | Petersen et al. |
| 6,899,137 B2 | 5/2005 | Unger et al. |
| 6,915,679 B2 | 7/2005 | Chien et al. |
| 6,929,030 B2 | 8/2005 | Unger et al. |
| 6,939,452 B2 | 9/2005 | Foret et al. |
| 6,977,145 B2 | 12/2005 | Fouillet et al. |
| 7,052,545 B2 | 5/2006 | Quake et al. |
| 7,144,616 B1 | 12/2006 | Unger et al. |
| 7,155,344 B1 | 12/2006 | Parce et al. |
| 7,171,983 B2 | 2/2007 | Chien et al. |
| 7,195,670 B2 | 3/2007 | Hansen et al. |
| 7,343,248 B2 | 3/2008 | Parce et al. |
| 7,347,975 B2 * | 3/2008 | Vann et al. ................ 422/100 |
| 2001/0027745 A1 | 10/2001 | Weigl et al. |
| 2001/0033796 A1 | 10/2001 | Unger et al. |
| 2001/0041357 A1 | 11/2001 | Fouillet et al. |
| 2001/0054778 A1 | 12/2001 | Unger et al. |
| 2002/0029814 A1 | 3/2002 | Unger et al. |
| 2002/0037499 A1 | 3/2002 | Quake et al. |
| 2002/0064885 A1 | 5/2002 | Bedingham et al. |
| 2002/0144738 A1 | 10/2002 | Unger et al. |
| 2002/0145231 A1 | 10/2002 | Hansen et al. |
| 2002/0191048 A1 | 12/2002 | Mutz et al. |
| 2002/0195050 A1 | 12/2002 | David |
| 2002/0197603 A1 | 12/2002 | Chow et al. |
| 2003/0008286 A1 | 1/2003 | Zou et al. |
| 2003/0027225 A1 | 2/2003 | Wada et al. |
| 2003/0061687 A1 | 4/2003 | Hansen et al. |
| 2003/0096310 A1 | 5/2003 | Hansen et al. |
| 2003/0143120 A1 | 7/2003 | Ruediger et al. |
| 2003/0175947 A1 | 9/2003 | Liu et al. |
| 2004/0115731 A1 | 6/2004 | Hansen et al. |
| 2004/0141887 A1 | 7/2004 | Mainquist et al. |
| 2004/0203055 A1 | 10/2004 | Kennedy et al. |
| 2005/0019794 A1 | 1/2005 | Nassef et al. |
| 2005/0042768 A1 | 2/2005 | Fredrick |
| 2005/0062196 A1 | 3/2005 | Hansen et al. |
| 2005/0112882 A1 | 5/2005 | Unger et al. |
| 2005/0129581 A1 | 6/2005 | McBride et al. |
| 2005/0166980 A1 | 8/2005 | Unger et al. |
| 2005/0205005 A1 | 9/2005 | Hansen et al. |
| 2005/0221373 A1 | 10/2005 | Enzelberger et al. |
| 2005/0226742 A1 | 10/2005 | Unger et al. |
| 2005/0229839 A1 | 10/2005 | Quake et al. |
| 2005/0282175 A1 | 12/2005 | Taylor et al. |
| 2006/0211134 A1 | 9/2006 | Kennedy et al. |

FOREIGN PATENT DOCUMENTS

| | | |
|---|---|---|
| EP | 0 592 094 A2 | 4/1994 |
| EP | 0 703 364 A1 | 3/1996 |
| EP | 0 706 004 A2 | 4/1996 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| GB | 2 155 152 A | 9/1985 |
| GB | 2 308 460 A | 6/1997 |
| WO | WO 98/07069 A1 | 2/1998 |
| WO | WO 99/00655 A2 | 1/1999 |
| WO | WO 99/04361 A1 | 1/1999 |
| WO | WO 99/17093 A1 | 4/1999 |
| WO | WO 99/52633 A1 | 10/1999 |
| WO | WO 00/00678 A1 | 1/2000 |
| WO | WO 00/43748 A1 | 7/2000 |
| WO | WO 00/60345 A1 | 10/2000 |
| WO | WO 01/09595 A2 | 2/2001 |

| WO | WO 01/09595 A3 | 2/2001 |
| WO | WO 02/082047 A2 | 10/2002 |
| WO | WO 03/053585 A1 | 7/2003 |

OTHER PUBLICATIONS

"Chapter 9: Microfluidic Devices," Micromachined Transducers Sourcebook, pp. 779-882, 1998.
"Last Chance For Micromachines," The Economist Technology Quarterly, 8 pages, Dec. 7, 2000.
"The Liver Chip," Technology Review, pp. 64-67, Mar. 2003.
Abola, Enrique et al., "Automation Of X-Ray Crystallography," Nature Structural Biology, Structural Genomics Supplement, pp. 973-977, Nov. 2000.
Andersen, Gregers Rom et al., "A Spreadsheet Approach To Automated Protein Crystallization," Journal of Applied Crystallography, vol. 29, pp. 236-240, 1996.
Anderson, Rolfe C. et al., "Microfluidic Biochemical Analysis System," Transducers '97, 1997 International Conference on Solid-State Sensors and Actuators, Chicago, Illnois, pp. 477-480, Jun. 16-19, 1997.
Angell, James B. et al., "Silicon Micromechanical Devices," Scientific American, pp. cover, 44-55, Apr. 1983.
Armani, Deniz et al., "Re-Configurable Fluid Circuits By PDMS Elastomer Micromachining," IEEE Int. Conf. Micro Electro Mech. Syst. Tech. Digest, vol. 12, pp. 222-227, 1999.
Ballantyne, J. P. et al., "Selective Area Metallization By Electron-Beam Controlled Direct Metallic Deposition," J. Vac. Sci. Technol., vol. 10, No. 6, pp. 1094-1097, Nov. 1973.
Belgrader, Phillip et al., "Rapid Pathogen Detection Using a Microchip PCR Array Instrument," Clinical Chemistry, vol. 44, No. 10, pp. 2191-2194, 1998.
Benard, W. L. et al., "A Titanium-Nickel Shape-Memory Alloy Actuated Micropump," Transducers '97, 1997 International Conference on Solid-State Sensors and Actuators, Chicago, Illinois, pp. 361-364, Jun. 16-19, 1997.
Berry, Michael B., "Protein Crystallization: Theory And Practice," Excerpts from Doctoral Thesis, 36 pages, Sep. 17, 1995.
Black, Harvey, "Tiny Technology Promises Tremendous Profits," The Scientist, vol. 15, No. 21, 4 pages, Oct. 29, 2001.
Bloomstein, T. M. et al., "Laser-Chemical Three-Dimensional Writing For Microelectromechanics And Application To Standard-Cell Microfluidics," J. Vac. Sci. Technol. B, vol. 10, No. 6, pp. 2671-2674, Nov. 1992.
Bousse, Luc et al., "Electrokinetically Controlled Microfluidic Analysis Systems," Annu. Rev. Biophys. Biomol. Struct., vol. 29, pp. 155-181, 2000.
Brechtel, R. et al., "Control Of The Electroosmotic Flow By Metal-Salt-Containing Buffers," Journal of Chromatography A, vol. 716, pp. 97-105, 1995.
Brush, Michael, "Automated Laboratories," The Scientist, vol. 13, No. 4, 10 pages, Feb. 15, 1999.
Bryzek, Janusz et al., "Micromachines On The March", IEEE Spectrum, vol. 31, No. 5, pp. 20-31, May 1994.
Buchaillot, Lionel et al., "Silicon Nitride Thin Films Young's Modulus Determination By An Optical Non Destructive Method," Jpn. J. Appl. Phys., vol. 36, Part 2, No. 6B, pp. L794-L797, Jun. 15, 1997.
Burbaum, Jonathan J. et al., "New Technologies For High-Throughput Screening," Current Opinion in Chemical Biology, vol. 1, pp. 72-78, 1997.
Calkins, Kathryn, "Mycometrix: Rubber Chips," BioCentury, 2 pages, Oct. 16, 2000.
Carter, Charles W. Jr. et al., "Protein Crystallization Using Incomplete Factorial Experiments," Journal of Biological Chemistry, vol. 254, No. 23, pp. 12219-12223, Dec. 10, 1979.
Carter, Charles W. Jr. et al., "Statistical Design Of Experiments For Protein Crystal Growth And The Use Of A Precrystallization Assay," Journal of Crystal Growth, vol. 90, pp. 60-73, 1998.
Change, Jun Keun et al., "Functional Integration of Serial Dilution And Capillary Electrophoresis On A PDMS Microchip," Biotechnology and Bioprocess Engineering, vol. 8, No. 4, pp. 233-239, 2003.

Chayen, Naomi E., "A Novel Technique To Control The Rate Of Vapour Diffusion, Giving Larger Protein Crystals," Journal of Applied Crystallography, vol. 30, pp. 198-202, 1997.
Chayen, Naomi E. et al., "An Automated System For Micro-Batch Protein Crystallization And Screening," J. Appl. Cryst., vol. 23, pp. 297-302, 1990.
Chayen, Naomi E., "Comparative Studies Of Protein Crystallization By Vapour-Diffusion And Microbatch Techniques," Acta Cryst., vol. D54, pp. 8-15, 1998.
Chayen, Naomi E. et al., "Microbatch Crystallization Under Oil—A New Technique Allowing Many Small-Volume Crystallization Trials," Journal of Crystal Growth, vol. 122, pp. 176-180, 1992.
Chayen, Naomi E. et al., "New Developments Of The IMPAX Small-Volume Automated Crystallization System," Acta Cryst., vol. D50, pp. 456-458, 1994.
Chayen, Naomi E., "Protein Crystallization For Genomics: Throughput Versus Output," Journal of Structural and Functional Genomics, vol. 4, pp. 115-120, 2003.
Chayen, Naomi E., "The Role of Oil In Macromolecular Crystallisation," Structure, vol. 5, pp. 1269-1274, Oct. 15, 1997.
Chen, Chihchen et al., "Gray-Scale Photolithography Using Microfluidic Photomasks," PNAS, vol. 100, No. 4, pp. 1499-1504, Feb. 18, 2003.
Chiu, Daniel T. et al., "Patterned Deposition Of Cells And Proteins Onto Surfaces By Using Three-Dimensional Microfluidic Systems," PNAS, vol. 97, No. 6, pp. 2408-2413, Mar. 14, 2000.
Chou, Hou-Pu et al., "A Microfabricated Device For Sizing And Sorting DNA Molecules," Proc. Natl. Acad. Sci., vol. 96, pp. 11-13, Jan. 1999.
Chou, Hou-Pu et al., "A Microfabricated Rotary Pump," Biomedical Microdevices, vol. 3, No. 4, pp. 323-330, 2001.
Chou, Hou-Pu et al., "Integrated Elastomer Fluidic Lab-On-A-Chip-Surface Patterning And DNA Diagnostics," Proceedings of the Solid State Actuator and Sensor Workshop, Hilton Head, South Carolina, 4 pages, 2000.
Chou, Hou-Pu et al., "Multiple Disease Diagnostics On A Single Chip," Biophysics Lab, Caltech, pp. 1-4, Mar. 1, 2000.
Effenhauser, Carlo S. et al., "Integrated Capillary Electrophoresis On Flexible Silicone Microdevices: Analysis Of DNA Restriction Fragments And Detection Of Single DNA Molecules On Microchips," Analytical Chemistry, vol. 69, No. 17, pp. 3451-3457, Sep. 1, 1997.
D'Arcy, Allan et al., "The Advantages Of Using A Modified Microbatch Method For Rapid Screening Of Protein Crystallization Conditions," Acta Crystallographica, vol. D59, pp. 1-3, 2003.
Delamarche, Emmanuel et al., "Patterned Delivery Of Immunoglobulins To Surfaces Using Microfluidic Networks," Science, vol. 276, pp. 779-781, May 2, 1997.
Ducruix A. et al., "Crystallization Of Nucleic Acids And Proteins—A Practical Approach," IRL Press, pp. 2 cover pages and 73-98, 1992.
Duffy, David C. et al., "Patterning Electroluminescent Materials With Feature Sizes As Small As 5µm Using Elastomeric Membranes As Masks For Dry Lift-Off," Advanced Materials, vol. 11, No. 7, pp. 546-552, 1999.
Duffy, David C. et al., "Rapid Prototyping Of Microfluidic Switches in Poly(dimethyl siloxane) And Their Actuation By Electro-Osmotic Flow," Micromech. Microeng., vol. 9, pp. 211-217, 1999.
Duffy, David C. et al., "Rapid Prototyping Of Microfluidic Systems in Poly(dimethylsiloxane)," Analytical Chemistry, vol. 70, No. 23, pp. 4974-4984, Dec. 1, 1998.
Effenhauser, Carlo S. et al., "Integrated Chip-Based Capillary Electrophoresis," Electrophoresis, vol. 18, pp. 2203-2213, 1997.
Eisele, Jean-Luc, "Preparation Of Protein Cystallization Buffers With A Computer-Controlled Motorized Pipette—PIPEX," J. Appl. Cryst., vol. 26, pp. 92-96, 1993.
Eyal, Shulamit et al., "Velocity-Independent Microfluidic Flow Cytometry," Electrophoresis, vol. 23, pp. 2653-2657, 2002.
Fahrenberg, J. et al., "A Microvalve System Fabricated By Thermoplastic Molding," J. Micromech. Microeng., vol. 5, pp. 169-171, 1995.
Fenna, R. E., "Crystallization Of Human α-Lactalbumin," J. Mol. Biol., vol. 161, pp. 211-215, 1982.

Fettinger, J. C. et al., "Stacked Modules For Micro Flow Systems in Chemical Analysis: Concept And Studies Using An Enlarged Model," Sensors and Actuators B, vol. 17, pp. 19-25, 1993.

Fitzgerald, Deborah A., "Making Every Nanoliter Count," The Scientist, vol. 15, No. 21, 8 pages, Oct. 29, 2001.

Folch, A. et al., "Molding Of Deep Polydimethylsiloxane Microstructures For Microfluidics And Biological Applications," Journal of Biomechanical Engineering, vol. 121, pp. 28-34, Feb. 1999.

Fox, Kristin M. et al., "Crystalization of Old Yellow Enzyme Illustrates An Effective Strategy For Increasing Protein Crystal Size," J. Mol. Biol., vol. 234, pp. 502-507, 1993.

Fu, Anne Y. et al., "A Microfabricated Fluorescence-Activated Cell-Sorter," Nature Biotechnology, vol. 17, pp. 1109-1111, Nov. 1999.

Galambos, Paul et al., "Electrical And Fluidic Packaging Of Surface Micromachined Electro-Microfluidic Devices," 8 pages, no date.

Gao, Jun et al., "Integrated Microfluidic System Enabling Protein Digestion, Peptide Separation, And Protein Identification," Analytical Chemistry, vol. 73, No. 11, pp. 2648-2655, Jun. 1, 2001.

Garcia-Ruiz, J. M. et al., "Agarose As Crystallization Media For Proteins I: Transport Processes," Journal of Crystal Growth, vol. 232, pp. 165-172, 2001.

Garcia-Ruiz, J. M. et al., "Investigations On Protein Crystal Growth By The Gel Acupuncture Method," Acta Cryst., vol. D50, pp. 484-490, 1994.

Garno, Jayne C. et al., "Production Of Periodic Arrays Of Protein Nanostructures Using Particle Lithography," Langmuir, vol. 18, No. 21, pp. 8186-8192, 2002.

Gass, V. et al., "Integrated Flow-Regulated Silicon Micropump," Sensors and Actuators A, vol. 43, pp. 335-338, 1994.

Gerlach, Torsten, "Pumping Gases By A Silicon Micro Pump With Dynamic Passive Valves," Transducers '97, 1997 International Conference on Solid-State Sensors and Actuators, Chicago, Illinois, pp. 357-360, Jun. 16-19, 1997.

Goll, C. et al., "Microvalves With Bistable Buckled Polymer Diaphragms," J. Micromech. Microeng., vol. 6, pp. 77-79, 1996.

Gravesen, Peter et al., "Microfluidics-A Review," J. Micromech. Microeng., vol. 3, pp. 168-192, 1993.

Greene, Chana, "Characterizing The Properties Of PDMS," pp. 1-11, Summer 2000.

Grover, William H. et al., "Monolithic Membrane Valves And Diaphragm Pumps For Practical Large-Scale Integration into Glass Microfluidic Devices," Sensors and Actuators B, vol. 89, pp. 315-323, 2003.

Guérin, L. J. et al., "Simple And Low Cost Fabrication Of Embedded Micro-Channels By Using A New Thick-Film Photoplastic," Transducers '97, 1997 International Conference on Solid-State Sensors and Actuators, Chicago, Illinois, pp. 1419-1422, Jun. 18-19, 1997.

Hansen, Carl. L. et al., "A Robust And Scalable Microfluidic Metering Method That Allows Protein Crystal Growth By Free Interface Diffusion," PNAS, vol. 99, No. 26, pp. 16531-16536, Dec. 24, 2002.

Hansen, Carl. L. et al., "Systematic Investigation Of Protein-Phase Behavior With A Microfluidic Formulator," PNAS Early Edition, 6 pages, 2004.

Harrison, D. Jed et al., "Micromachining A Miniaturized Capillary Electrophoresis-Based Chemical Analysis System On A Chip," Science, vol. 261, pp. 895-897, Aug. 13, 1993.

Hicks, Jennifer, "Genetics And Drug Discovery Dominate Microarray Reasearch," R&D Magazine, pp. 28-33, Feb. 1999.

Hofmann, Oliver et al., "Modular Approach to Fabrication Of Three-Dimensional Microchannel Systems In PDMS—Application To Sheath Flow Microchips," Lab on a Chip, vol. 1, pp. 108-114, 2001.

Hong, Jong Wook et al., "A Nanoliter-Scale Nucleic Acid Processor With Parallel Architecture," Nature Biotechnology, vol. 22, No. 4, pp. 1-5, Apr. 2004.

Horn, Howard, "Lab Chips Sector: Microtechnologies Are Changing Healthcare And More," Life Sciences, pp. 19-21, Mar. 20, 2001.

Hornbeck, Larry J. et al., "Bistable Deformable Mirror Device," Spatial Light Modulators and Applications 1988 Technical Digest Series, Summaries of papers presented at the Spatial Light Modulators and Applications Topical Meeting, Optical Society of America, vol. 8, Postconference Edition, A215, pp. 107-110, Jun. 15-17, 1988.

Hosokawa, Kazuo et al., "A Microfluidic Device For Mixing Of Capillary-Drive Liquids," IEEJ Trans. SM, vol. 123, No. 1, pp. 23-24, 2003.

Hosokawa, Kazuo et al., "Handling Of Picoliter Liquid Samples In A Poly(dimethylsiloxane)-Based Microfluidic Device," Analytical Chemistry, vol. 71, No. 20, pp. 4781-4785, Oct. 15, 1999.

Ikuta, Koji et al., "Three Dimensional Micro Integrated Fluid Systems (MIFS) Fabricated By Stereo Lithography," IEEE, pp. 1-6, 1994.

Jacobson, Stephen C. et al., "High-Speed Separations On A Microchip," Analytical Chemistry, vol. 66, No. 7, pp. 1114-1118, Apr. 1, 1994.

Jacobson, Stephen C. et al., "Microfluidic Devices For Electrokinetically Driven Parallel And Serial Mixing," Analytical Chemistry, vol. 71, No. 20, pp. 4455-4459, Oct. 15, 1999.

Jerman, Hal, "Electrically-Activated, Normally-Closed Diaphragm Valves," Transducers '91, 1991 International Conference on Solid-State Sensors and Actuators, pp. cover, 1045-1048, 1991.

Jo Byung-Ho et al., "Fabrication Of Three-Dimensional Microfluidic Systems By Stacking Molded Polydimethylsiloxane (PDMS) Layers" SPIE, vol. 3877, pp. 222-229, Sep. 1999.

Jo, Byung-Ho et al., "Three-Dimensional Micro-Channel Fabrication In Polydimethylsiloxane (PDMS) Elastomer," Journal of Microelectromechanical Systems, vol. 9, No. 1, pp. 76-81, Mar. 2000.

Juárez-Martinez, G. et al., "High-Throughput Screens For Postgenomics: Studies Of Protein Crystallization Using Microsystems Technology," Analytical Chemistry, vol. 74, No. 14, pp. 3505-3510, Jul. 15, 2002.

Jung, D. R. et al., "Chemical And Physical Interactions At Metal/Self-Assembled Organic Monolayer Interfaces," pp. 1-54, 1994.

Kagan, C. R., "Organic-Inorganic Hybrid Materials As Semiconducting Channels In Thin-Film Field-Effect Transistors," Science, vol. 286, pp. 945-947, Oct. 29, 1999.

Kamholz, Andrew Evan et al., "Quantitative Analysis Of Molecular Interaction In A Microfluidic Channel: The T-Sensor," Analytical Chemistry, vol. 71, No. 23, pp. 5340-5347, Dec. 1, 1999.

Kapur, Ravi et al., "Fabrication And Selective Surface Modification Of 3-Dimensionally Textured Biomedical Polymers From Etched Silicon Substrates," Journal of Biomedical Materials Research, vol. 33, p. 205-216, 1996.

Kenis, Paul J. A. et al., "Microfabrication Inside Capillaries Using Multiphase Laminar Flow Patterning," Science, vol. 285, pp. 83-85, Jul. 2, 1999.

Khoo, Melvin et al., "A Novel Micromachined Magnetic Membrane Microfluid Pump," pp. 1-4, no date.

Kim, Enoch et al., "Micromolding In Capillaries: Applications In Materials Science," J. Am. Chem. Soc., vol. 118, No. 24, pp. 5722-5731, 1996.

Kim, Enoch et al., "Polymer Microstructures Formed By Moulding In Capillaries," Nature, vol. 376, pp. 581-584, Aug. 17, 1995.

Kirk-Othmer, "Concise Encyclopedia of Chemical Technology," John Wiley & Sons, 5 pages, no date.

Kopp, Martin U. et al., "Chemical Amplification: Continuous-Flow PCR On A Chip," Science, vol. 280, pp. 1046-1048, May 15, 1998.

Kuhn, Lawrence et al., "Silicon Charge Electrode Array For Ink Jet Printing," IEEE Transactions on Electron Devices, vol. ED-25, No. 10, pp. 1257-1260, Oct. 1978.

Kuhn, Peter et al., "The Genesis Of High-Throughput Structure-Based Drug Discovery Using Protein Crystallography," Current Opinion in Chemical Biology, vol. 6, pp. 704-710, 2002.

Kumar, Amit et al., "Features Of Gold Having Micrometer To Centimeter Dimensions Can Be Formed Through A Combination Of Stamping With An Elastomeric Stamp And An Alkanethiol 'Ink' Followed By Chemical Etching," Appl. Phys. Lett., vol. 63, No. 14, pp. 2002-2004, Oct. 4, 1993.

Kumar, Amit et al., "Patterning Self-Assembled Monolayers: Applications In Materials Science," Langmuir, vol. 10, pp. 1498-1511, 1994.

Kwong, Peter D. et al., "Probability Analysis Of Variational Crystallization And Its Application To gp120, The Exterior Envelope Glycoprotein Of Type 1 Human Immunodeficiency Virus (HIV-1)," Journal of Biological Chemistry, vol. 274, No. 7, pp. 4115-4123, Feb. 12, 1999.

Kwong, Peter D. et al., "Structure Of An HIV gp 120 Envelope Glycoprotein In Complex With The CD4 Receptor And A Neutralizing Human Antibody," Nature, vol. 393, pp. 648-659, Jun. 18, 1998.

Lagally, Eric T. et al., "Fully Integrated PCR-Capillary Electrophoresis Microsystem For DNA Analysis," Lab On A Chip, vol. 1, pp. 102-107, 2001.

Lagally, Eric T. et al., "Monolithic Integrated Microfluidic DNA Amplification And Capillary Electrophoresis Analysis System," Sensors and Actuators B, vol. 63, pp. 138-146, 2000.

Lagally, E. T. et al., "Single-Molecule DNA Amplification And Analysis In An Integrated Microfluidic Device," Analytical Chemistry, vol. 73, No. 3, pp. 565-570, Feb. 1, 2001.

Lammerink, T. S. J. et al., "Modular Concept For Fluid Handling Systems," IEEE, pp. 389-394, 1996.

Li, Paul C. H. et al., "Transport, Manipulation, And Reaction Of Biological Cells On-Chip Using Electrokinetic Effects," Analytical Chemistry, vol. 69, No. 8, pp. 1564-1568, Apr. 15, 1997.

Licklider, Larry et al., "A Micromachined Chip-Based Electrospray Source For Mass Spectrometry," Analytical Chemistry, vol. 72, No. 2, pp. 367-375, Jan. 15, 2000.

Lin, L. Y. et al., "Free-Space Micromachined Optical Switches For Optical Networking," IEEE Journal of Selected Topics in Quantum Electronics, vol. 5, No. 1, pp. 4-9, Jan. 1999.

Lin, H. et al., "Convective-Diffusive Transport in Protein Crystal Growth," Journal of Crystal Growth, vol. 151, pp. 153-162, 1995.

Liu, Jian et al., "A Nanoliter Rotary Device For Polymerase Chain Reaction," Electrophoresis, vol. 23, pp. 1531-1536, 2002.

López-Jaramillo, F. J. et al., "Crystallization And Cryocrystallography Inside X-ray Capillaries," Journal of Applied Crystallography, vol. 34, pp. 365-370, 2001.

Lötters, J C et al., "The Mechanical Properties Of The Rubber Elastic Polymer Polydimethylsiloxane For Sensor Applications," J. Micromech. Microeng., vol. 7, pp. 145-147, 1997.

Lucy, Charles A. et al., "Characterization Of The Cationic Surfactant Induced Reversal Of Electroosmotic Flow In Capillary Electrophoresis," Anal. Chem., vol. 68, pp. 300-305, 1996.

Luft, Joseph R. et al., "A Method To Produce Microseed Stock For Use In The Crystallization Of Biological Macromolecules," Acta Cryst., vol. D55, pp. 988-993, 1999.

Luft, Joseph R. et al., "Kinetic Aspects Of Macromolecular Crystallization," Methods In Enzymology, vol. 276, pp. 110-131, 1997.

Luft, Joseph R. et al., "Macromolecular Crystallization In A High Throughput Laboratory—The Search Phase," Journal of Crystal Growth, vol. 232, pp. 591-595, 2001.

Luft, Joseph R. et al., "Microbatch Macromolecular Crystallization In Micropipettes," Journal of Crystal Growth, vol. 196, pp. 450-455, 1999.

Maluf, N., "An Introduction To Microelectromechanical Systems Engineering," Artech House Publishers, Boston London, pp. 42-45, Dec. 1999.

Manz, A. et al., "Micromaching Of Monocrystalline Silicon And Glass For Chemical Analysis Systems," Trends in Analytical Chemistry, vol. 10, No. 5, pp. 144-149, 1991.

Marshall, Sid, "Fundamental Changes Ahead For Lab Instrumentation," R&D Magazine, 5 pages, Feb. 1999.

Marsili, Ray, "Lab-On-A-Chip Poised To Revolutionize Sample Prep," R&D Magazine, 5 pages, Feb. 1999.

McDonald, J. Cooper et al., "Fabrication Of Microfluidic Systems in Poly(dimethylsiloxane)," Electrophoresis, vol. 21, pp. 27-40, 2000.

McDonald, J. Cooper et al., "Poly(dimethylsiloxane) As A Material For Fabricating Microfluidic Devices," Accounts of Chemical Research, vol. 35, No. 7, pp. 491-499, 2002.

McPherson, Alexander, "Crystallization Of Macromolecules: General Principles," Methods in Enzymology, vol. 114, pp. 112-120, 1985.

McPherson, Alexander, "Crystallization Of Proteins By Variation Of pH Or Temperature," Methods in Enzymology, vol. 114, pp. 125-127, 1985.

McPherson, Alexander et al., "Use Of Polyethylene Glycol In The Crystallization Of Macromolecules," Methods in Enzymology, vol. 114, pp. 120-125, 1985.

Miller, Teresa Y. et al., "A Comparison Between Protein Crystals Grown With Vapor Diffusion Methods In Microgravity And Protein Crystals Using A Gel Liquid—Liquid Diffusion Ground-Based Method," Journal of Crystal Growth, vol. 122, pp. 306-309, 1992.

Morris, Daniel W. et al., "Automation Of Protein Crystallization Trials: Use Of A Robot To Deliver Reagents To A Novel Multi-Chamber Vapor Diffusion Plate," BioTechniques, vol. 7, No. 5, pp. 522-527, 1989.

Muller, Richard S. et al., "Surface-Micromachined Microoptical Elements And Systems," Proceedings of the IEEE, vol. 86, No. 8, pp. 1705-1720, Aug. 1998.

Nerad, B. A. et al., "Ground-Based Experiments On The Minimization Of Convention During The Growth Of Crystals From Solution," Journal of Crystal Growth, vol. 75, pp. 591-608, 1986.

Ng, Jessamine M. K. et al., "Components For Integrated Poly(Dimethylsiloxane) Microfluidic Systems," Electrophoresis, vol. 23, pp. 3461-3473, 2002.

Nollert, Peter et al., "Crystallization Of Membrane Proteins *in Cubo*," Methods in Enzymology, vol 343, pp. 183-199, 2002.

Oldfield, T. J. et al., "A Flexible Approach To Automated Protein Crystallization," J. Appl. Cryst., vol. 24, pp. 255-260, 1991.

Oleschuk, Richard D. et al., "Analytical Microdevices For Mass Spectrometry," Trends In Analytical Chemistry, vol. 19, No. 6., pp. 379-388, 2000.

Olsson, Anders et al., "Simulation Studies Of Diffuser And Nozzle Elements For Valve-Less Micropumps," Transducers '97, 1997 International Conference on Solid-State Sensors and Actuators, Chicago, Illinois, pp. 1039-1042, Jun. 16-19, 1997.

Pethig, Ronald et al., "Applications Of Dielectrophoresis In Biotechnology," Tibtech, vol. 15, pp. 426-432, Oct. 1997.

Qin, Dong et al., "Elastomeric Light Valves," Adv. Mater., vol. 9, No. 5, pp. 407-410, 1997.

Qin, Dong et al., "Photolithography With Transparent Reflective Photomasks," J. Vac. Sci. Technol. B, vol. 16, No. 1, pp. 98-103, Jan. 1998.

Quake, Stephen R. et al., "From Micro- To Nanofabrication With Soft Materials," Science, vol. 290, pp. 1536-1540, Nov. 24, 2000.

Rapp, R. et al., "LIGA Micropump For Gases And Liquids," Sensors and Actuators A, vol. 40, pp. 57-61, Jan. 1994.

Reshetnyak, I. I., "Characteristics Of The Influence Of Ultrasound On The Crystallization Kinetics In Small-Volume Solutions," Sov. Phys. Acoust., vol. 21, No. 1, pp. 61-63, Jul. 1975.

Roylance, Lynn Michelle et al., "A Batch-Fabricated Silicon Accelerometer," IEEE Transactions on Electron Devices, vol. ED-26, No. 12, pp. 1911-1917, Dec. 1979.

Rubin, Byron et al., "Minimal Intervention Robotic Protein Crystallization," Journal of Crystal Growth, vol. 110, pp. 156-163, 1991.

Rummel, Gabriele et al., "Lipidic Cubic Phases: New Matrices For The Three-Dimensional Crystallization Of Membrane Proteins," Journal of Structural Biology, vol. 121, pp. 82-91, 1998.

Sadaoui, Nouredine et al., "TAOS: An Automatic System For Protein Crystallization," Journal of Applied Crystallography, vol. 27, pp. 622-626, 1994.

Salemme, F. R., "A Free Interface Diffusion Technique For The Crystallization Of Proteins For X-Ray Crystallography," Archives of Biochemistry and Biophysics, vol. 151, pp. 533-539, 1972.

Sandia National Laboratories, "Electro Microfluidic Dual In-Line Package (EMDIP)," 2 pages, no date.

Sanjoh, Akira, et al., "Spatiotemporal Protein Crystal Growth Studies Using Microfluidic Silicon Devices," Journal of Crystal Growth, vol. 196, pp. 691-702, 1999.

Santarsiero, B. D. et al., "An Approach to Rapid Protein Crystallization Using Nanodroplets," Journal of Applied Crystallography, vol. 35, pp. 278-281, 2002.

Sasserath, J. et al., "Rapid Prototyping And Development Of Microfluidic And BioMEMS Devices," IVD Technology, 12 pages, Jun. 2002.

Schasfoort, Richard B. M. et al., "Field-Effect Flow Control For Microfabricated Fluidic Networks," Science, vol. 286, pp. 942-945, Oct. 29, 1999.

Schueller, Olivier J. A. et al., "Fabrication Of Glassy Carbon Microstructures By Soft Lithography," Sensors and Actuators A, vol. 72, pp. 126-139, 1999.

Shoji, Shuichi, "Fluids For Sensor Systems," Topics in Current Chemistry, vol. 194, pp. 163-188, 1998.

Shoji, Shuichi et al., "Smallest Dead Volume Microvalves For Integrated Chemical Analyzing Systems," Transducers '91, 1991 International Conference on Solid-State Sensors and Actuators, San Francisco, California, pp. cover, 1052-1055, 1991.

Smits, J. G., "Piezoelectric Micropump With Three Valves Working Peristaltically," Sensors and Actuators, vol. A21-A23, pp. 203-206, 1990.

Snook, Christopher F. et al., "Use Of A Crystallization Robot To Set Up Sitting-Drop Vapor-Diffusion Crystallization And in situ Crystallization Screens," Journal of Applied Crystallography, vol. 33, pp. 344-349, 2000.

Sohn, L. L. et al., "Capacitance Cytometry: Measuring Biological Cells One By One," PNAS, vol. 97, No. 20, pp. 10687-10690, Sep. 26, 2000.

Soriano, Thierry M. B. et al., "ASTEC: An Automated System For Sitting-Drop Protein Crystallization," Journal of Applied Crystallography, vol. 26, pp. 558-562, 1993.

Stevens, Raymond C., "High-Throughput Protein Crystallization," Current Opinion in Structural Biology, vol. 10, pp. 558-563, 2000.

Stevens, Raymond C., "The Cost And Value Of Three-Dimensional Protein Structure," Drug Discovery World, pp. 35-48, Summer 2003.

Thomas, B. R. et al., "Distribution Coefficients Of Protein Impurities In Ferritin And Lysozyme Crystals Self-Purification In Microgravity," Journal of Crystal Growth, vol. 211, pp. 149-156, 2000.

Thompson, L. F. et al., "Introduction To Microlithography," 185th Meeting of the American Chemical Society, Seattle, WA, pp. 2 cover pages, 1-13, Mar. 20-25, 1983.

Thorsen, Todd et al., "Dynamic Pattern Formation In A Vesicle-Generating Microfluidic Device," Physical Review Letters, vol. 86, No. 18, pp. 4163-4166, Apr. 30, 2001.

Thorsen, Todd et al., "Microfluidic Large-Scale Integration," Science, vol. 298, No. 5593, pp. 580-584, Oct. 18, 2002.

Todd, Paul et al., "Application Of Osmotic Dewatering To The Controlled Crystallization Of Biological Macromolecules And Organic Compounds," Journal of Crystal Growth, vol. 110, pp. 283-292, 1991.

Tufte, O. N. et al., "Silicon Diffused-Element Piezoresistive Diaphragms," Journal of Applied Physics, vol. 33, No. 11, pp. 3322-3327, Nov. 1962.

Ullmann's Encyclopedia of Industrial Chemistry, Sections 6 to 6.3, Topic: Carbon Black, Sixth Edition, 7 pages, 1999.

Unger, Marc A. et al., "Monolithic Microfabricated Valves And Pumps By Multilayer Soft Lithography," Science, vol. 288, pp. 113-116, Apr. 7, 2000.

Van De Pol, F. C. M. et al., "A Thermo-Pneumatic Actuation Principle For A Microminiature Pump And Other Micromechanical Devices," Sensors and Actuators, vol 17, Nos. 1-2, pp. 139-143, May 3, 1989.

Van Be Pol, F. C. M. et al., "Micro Liquid Handling Devices—A Review," Micro Systems Technologies, vol. 90, pp. 799-805, 1990.

Van Den Berg, A. et al., "Micro Total Analysis Systems," Proceedings of the µTAS '94 Workshop, University of Twente, The Netherlands, 17 pages, Nov. 21-22, 1994.

Van Der Woerd, Mark et al., "Lab-On-A-Chip based Protein Crystallization," National Aeronautics and Space Administration and Caliper, pp. 1-27, Oct. 25, 2001.

Van Der Woerd, Mark et al., "The Promise Of Macromolecular Crystallization In Microfluidic Chips," Journal of Structural Biology, vol. 142, pp. 180-187, 2003.

Velev, Orlin D., "On-Chip Manipulation Of Free Droplets," Nature, vol. 426, pp. 515-516, Dec. 4, 2003.

Verpoorte, Elisabeth M. J. et al., "Three-Dimensional Micro Flow Manifolds For Miniaturized Chemical Analysis Systems," J. Micromech. Microeng., vol. 7, pp. 246-256, 1994.

Vieider, Christian et al., "A Pneumatically Actuated Micro Valve With A Silicon Rubber Membrane For Integration With Fluid Handling Systems," Transducers '95, 8th International Conference on Solid-State Sensors and Actuators and Eurosensors IX, Stockholm, Sweden, pp. 284-286, Jun. 25-29, 1995.

Vogelstein, Bert et al., "Digital PCR," Proc. Natl. Acad. Sci. USA, vol. 96, pp. 9236-9241, Aug. 1999.

Ward, Keith B. et al., "Automatic Preparation Of Protein Crystals Using Laboratory Robotics And Automated Visual Inspection," Journal of Crystal Growth, vol. 90, pp. 325-339, 1988.

Washizu, Masao et al., "Molecular Dielectrophoresis Of Biopolymers," IEEE Transactions on Industry Applications, vol. 30, No. 4, pp. 835-843, Jul. 1994.

Weber, Patricia C. et al., "Applications Of Calorimetric Methods To Drug Discovery And The Study of Protein Interactions," Current Opinion In Structural Biology, vol. 13, pp. 115-121, 2003.

Weselak, Mark et al., "Robotics For Automated Crystal Formation And Analysis," Methods in Enzymology, pp. 1-13, 2002.

Whelen, A. Christian et al., "The Role Of Nucleic Acid Amplification And Detection in The Clinical Microbiology Laboratory," Annu. Rev. Microbiol:, vol. 50, pp. 349-373, 1996.

Whitesides, George M. et al., "Flexible For Microfluidics," Physics Today, pp. 42-48, Jun. 2001.

Whitesides, George M. et al., "Soft Lithography in Biology And Biochemistry," Annu. Rev. Biomed. Eng., vol. 3, pp. 335-373, 2001.

Wiencek, J. M., "New Strategies For Protein Crystal Growth," Annu. Rev. Biomed. Eng., vol. 1, pp. 505-534, 1999.

Wilbur, James L. et al., "Lithographic Molding: A Convenient Route To Structures With Sub-Micrometer Dimensions," Adv. Mater., vol. 7, No. 7, pp. 649-652, 1995.

Wu, Hongkai et al., "Fabrication Of Complex Three-Dimensional Microchannel Systems In PDMS," J. Am. Chem. Soc., vol. 125, No. 2, pp. 554-559, 2003.

Xia, Younan et al., "Complex Optical Surfaces Formed By Replica Molding Against Elastomeric Masters," Science, vol. 273, pp. 347-349, Jul. 19, 1996.

Xia, Younan et al., "Micromolding Of Polymers In Capillaries: Applications In Microfabrication," Chem. Mater., vol. 8, No. 7, pp. 1559-1566, 1996.

Xia, Younan et al., "Reduction In The Size Of Patterned SAMs Generated By Microcontact Printing With Mechanical Compression Of The Stamp," Adv. Mater., vol. 7, No. 5, pp. 471-473, 1995.

Xia, Younan et al., "Soft Lithography," Angew. Chem. Int. Ed., vol. 37, pp. 551-575, 1998.

Xu, Bing et al., "Making Negative Poisson's Ratio Microstructures By Soft Lithography," Adv. Mater., vol. 11, No. 14, pp. 1186-1189, 1999.

Yang, Xing et al.; "A Low Power MEMS Silicone/Parylene Valve," Solid-State Sensor and Actuator Workshop, Hilton Head Island, South Carolina, 4 pages, Jun. 7-11, 1998.

Yang, Xing et al., "A MEMS Thermopneumatic Silicone Membrane Valve," IEEE 10th Annual International Workshop of Micro Electro Mechanical Systems, Nagoya, Japan, pp. cover, 114-118, Jan. 26-30, 1997.

Yazdi, Navid et al., "Micromachined Inertial Sensors," Proceedings of IEEE, vol. 86, No. 8, pp. 1640-1656, Aug. 1998.

Yeh, Joanne I., "A Manual Nanoscale Method For Protein Crystallization," Acta Crystallographica, vol. D59, pp. 1408-1413, 2003.

Young, A. M. et al., "Contoured Elastic-Membrane Microvalves For Microfluidic Network Integration," Journal of Biomechanical Engineering, vol. 121, pp. 2-6, Feb. 1999.

Zampighi, G. et al., "Structural Organization Of (Na++K+)-ATPase In Purified Membranes," Journal of Cell Biology, vol. 98, pp. 1851-1864, May 1984.

Zengerle, R. et al., "A Micro Membrane Pump With Electrostatic Actuation," Micro Electro Mechanical Systems '92, Travemünde, Germany, pp. 19-24, Feb. 4-7, 1992.

Zengerle, R. et al., "Performance Simulation Of Microminiaturized Membrane Pumps," 7th International Conference on Solid-State Sensors and Actuators, Yokohama, Japan, pp. 2 cover pages, 106-109, Jun. 7-10, 1993.

Zhao, Zhan, et al., "An Integrated Biochip Design And Fabrication," Proceedings of SPIE, vol. 4936, pp. 321-326, 2002.

Zheng, Bo'et al., "A Droplet-Based, Composite PDMS/Glass Capillary Microfluidic System For Evaluating Protein Crystallization Conditions By Microbatch And Vapor-Diffusion Methods With On-Chip X-Ray Diffraction," Angew. Chem., pp. 1-4, 2004.

Affholter, Joseph et al., "Engineering A Revolution," Chemistry in Britain, pp. 48-51, Apr. 1999.

Ahn, Chong H. et al., "Fluid Micropumps Based On Rotary Magnetic Actuators," Proceedings of 1995 IEEE Micro Electro Mechanical Systems Workshop (MEMS '95), Amsterdam, Netherlands, pp. 408-412, Jan. 29-Feb. 2, 1995.

Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Andersson et al., "Consecutive Microcontact Printing—Ligands For Asymmetric Catalysis in Silicon Channel," Sensors & Actuators B, vol. 3997, pp. 1-7, 2001.

Arnold, Frances H., "Design By Directed Evolution," Accounts of Chemical Research, vol. 31, No. 3, pp. 125-131, 1998.

Ashkin, A. et al., "Optical Trapping And Manipulation Of Single Cells Using Infrared Laser Beams," Nature, vol. 330, No. 24, pp. 769-771, Dec. 31, 1987.

Ashkin, A. et al., "Optical Trapping And Manipulation Of Viruses And Bacteria," Science, vol. 235, pp. 1517-1520, Mar. 20, 1987.

Buican, Tudor N. et al., "Automated Single-cell Manipulation And Sorting By Light Trapping," Applied Optics, vol. 26, No. 24, pp. 5311-5316, Dec. 15, 1987.

Hanes, Jozef, et al., "In Vitro Selection And Evolution Of Functional Proteins By Using Ribosome Display," Proc. Natl. Acad. Sci. USA, vol. 94, pp. 4937-4942, May 1997.

Hoffmuller, Ulrich et al., "In Vitro Evolution And Selection Of Proteins: Ribosome Display For Larger Libraries," Angew. Chem. Int. Ed., vol. 37, No. 23, pp. 3241-3243, Kamentsky, Louis A. et al., "Spectrophotometer: New Instrument For Ultrarapid Cell Analysis," Science, vol. 150, pp. 630-631, Oct. 29, 1965.

Phillips, George N. Jr., "Crystallization In Capillary Tubes," Methods In Enzymology, vol. 114, pp. 128-131, 1985.

Phillips, W.C. and Rayment, I. "A systematic method for aligning double focusing mittors," Methods in Enzymology, 1985, vol. 114 (Wyckoff, Hirs Timasheff, eds.), 316-329, Academic Press.

Roberts, Richard W. et al., "RNA-Peptide Fusions For The In Vitro Selection Of Peptides And Proteins," Proc. Natl. Acad. Sci. USA, vol. 94, pp. 12297-12302, Nov. 1997.

Sklar, Larry A. et al., Simple Handling For Kinetics And Molecular Assembly In Flow Cytometry, SPIE, vol. 3256, pp. 144-153, 1998.

Tawfik, Dan S. et at., "Man-Made Cell-Like Compartments For Molecular Evolution," Nature Biotechnology, vol. 16, pp. 652-656, Jul. 1998.

Webster's II Dictionary, p. 421, 1984.

Wu, Shuyun et al., "MEMS Flow Sensors For Nano-Fluidic Applications," Sensors and Actuators A, vol. 89, pp. 152-158, 2001.

Darlington, J., Proc. Nat. Acad. Sci. USA, vol. 69, No. 5, pp. 1239-1243, May 1972.

De Lucas et al., Journal of Structural Biology, vol. 142, Issue 1, Apr. 2003, pp. 188-206.

Hansen, Carl et al., "Crystallography in Drug Discovery," Feb. 20, 2004, Chapter 11, pp. 238-245.

Tsutsumi et al., Applied Energy vol. 67, Issues 1-2, Sep. 2000, pp. 195-219.

* cited by examiner

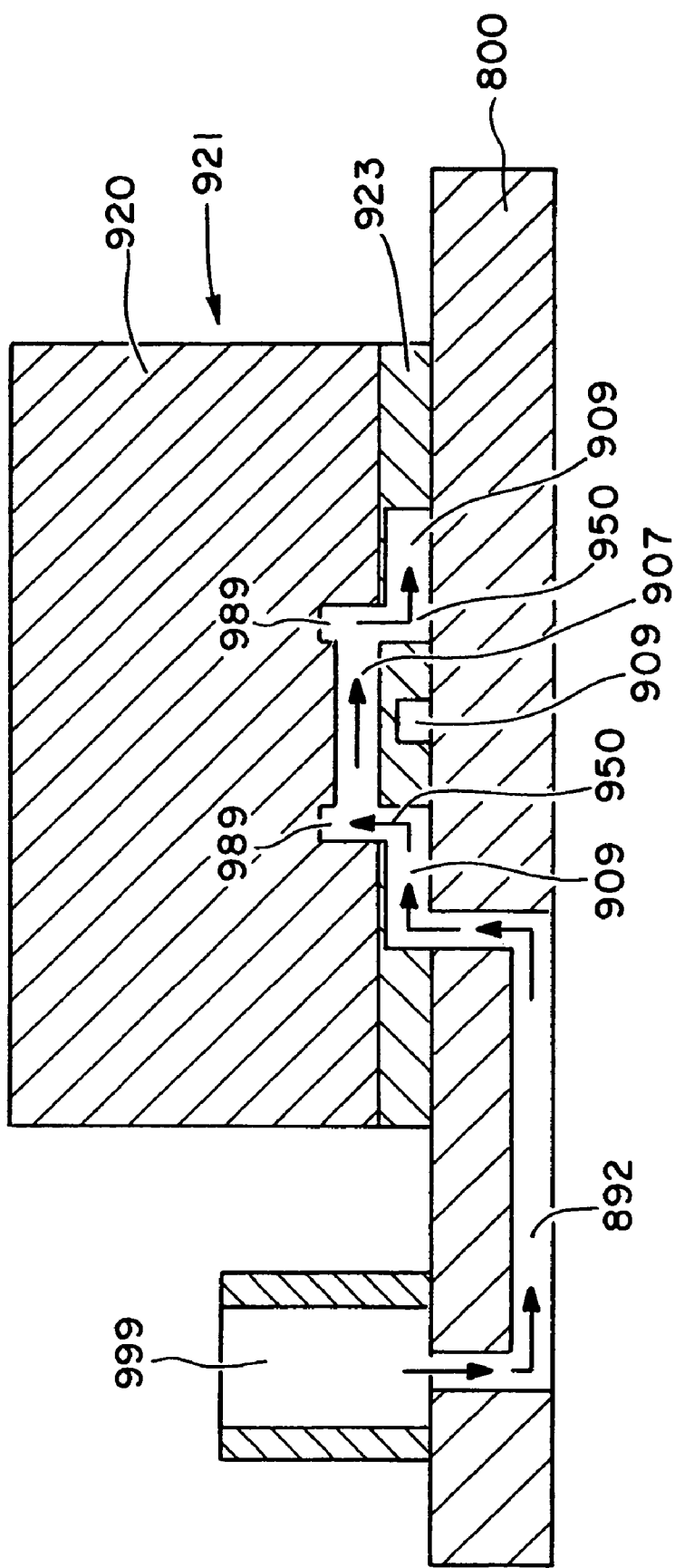

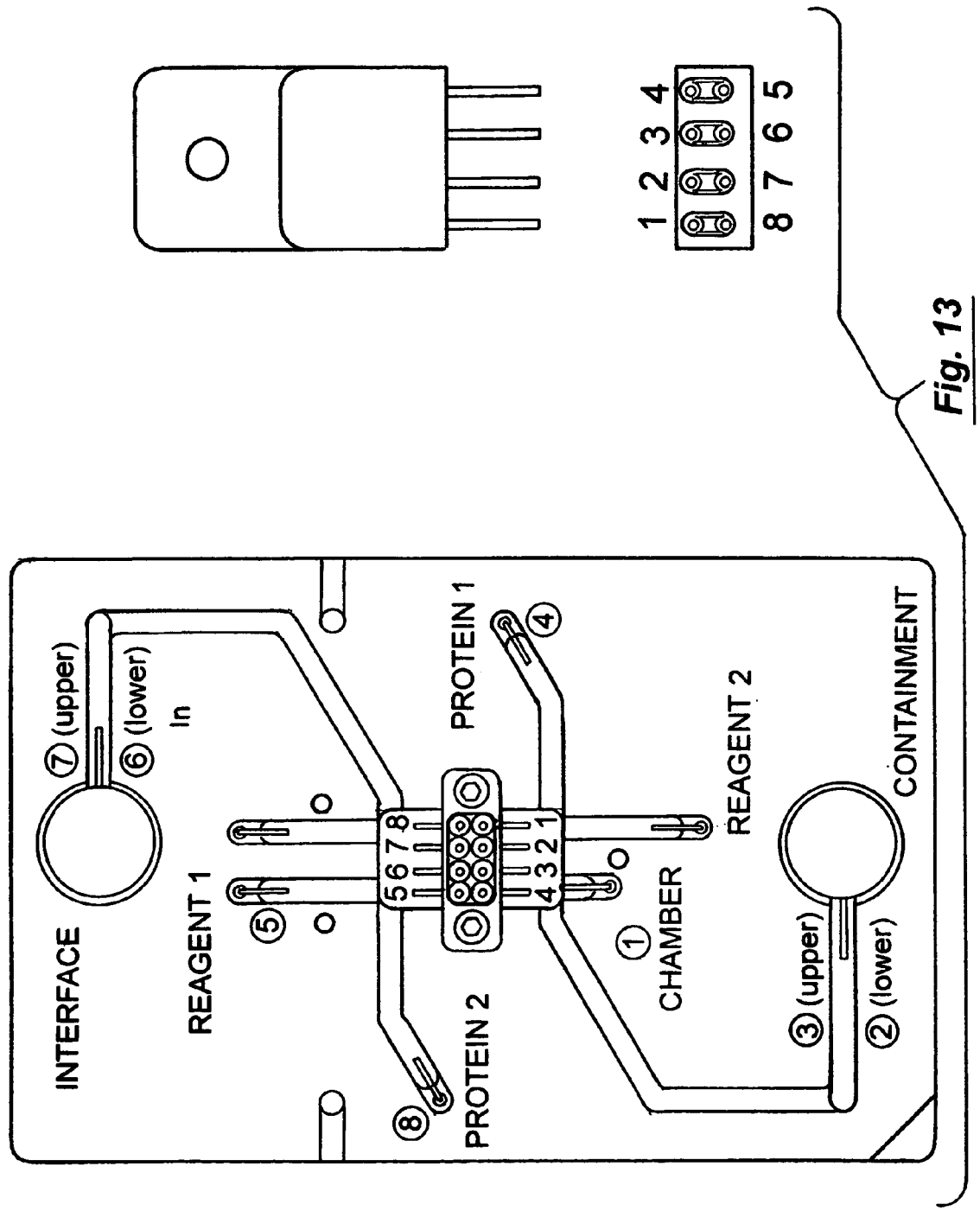

CRYSTAL FORMING DEVICES AND SYSTEMS AND METHODS FOR USING THE SAME

PRIORITY CLAIM

This application claims the benefit of priority under 35 U.S.C. §119(e) from the following co-owned and co-pending U.S. Provisional Patent Applications:

60/558,316, filed Mar. 30, 2004, by Unger, entitled Microfluidic Devices and Systems and Methods for Using the Same;

60/557,715, filed Mar. 29, 2004, by Unger, entitled Microfluidic Devices and Systems and Methods for Using the Same; and 60/539,283, filed Jan. 25, 2004, by Unger et al., entitled Microfluidic Devices and Systems and Methods for Using the Same;

each of which is herein incorporated by reference in their entirety for all purposes and the specific purposes disclosed herein.

CROSS-REFERENCES TO PATENTS AND PATENT APPLICATIONS

The invention is related to the subject matter disclosed in U.S. patent application Ser. No. 09/796,666, filed Feb. 28, 2001, entitled Microfabricated Elastomeric Valve and Pump Systems by Unger, et al. ("Unger"), now U.S. Pat. No. 6,408, 878; U.S. patent application Ser. No. 09/887,997, by Hansen, et al. ("Hansen"), filed June Apr. 5, 2002, which published as U.S. 2003.9961687 A1; and U.S. patent application Ser. No. 10/160,906, filed May 30, 2002 by Delucas, et al. ("Delucas"), which published as U.S. Patent Publication No. 2002/0164812 A1 on Nov. 2, 2002, which is a continuation of U.S. patent application Ser. No. 09/543,326, filed on Apr. 5, 2000, now abandoned, which claims priority to U.S. Provisional Patent Application No. 60/128,012, filed on Apr. 6, 1999, the disclosure of each being herein incorporated by reference for all purposes.

The invention is further related to U.S. patent application Ser. No. 10/997,714, filed Nov. 24, 2004, by Facer et. al, entitled Devices and Methods for Holding Microfluidic Devices, which claims priority to U.S. Provisional Application 60/525,245, filed Nov. 26, 2003, by Facer, et. al, the complete disclosures of which are incorporated herein by reference for all purposes.

The invention is further related to U.S. patent application Ser. No. 10/827,917, filed Apr. 19, 2004, by Nassef et. al, entitled Crystal Growth Devices and Systems, and Methods for Using Same, which claims priority to U.S. Provisional Application 60/509,098, filed Oct. 5, 2003, by Nassef et. al, to 60/466,305, filed Apr. 28, 2003, by Nassef et. al, and to 60/463,778, filed Apr. 17, 2003, by Nassef et. al, the complete disclosures of which are incorporated herein by reference for all purposes.

FIELD OF THE INVENTION

This invention relates to the fields of microfluidics, lab-on-a-chip, and Polymerase Chain Reactions ("PCR"), biochemical analysis, protein crystallization and screening for protein crystallization conditions, microfabrication, laboratory robotics, and automated biological screening and analysis, among other fields.

BACKGROUND OF THE INVENTION

Crystallization is an important technique to the biological and chemical arts. Specifically, a high-quality crystal of a target compound can be analyzed by x-ray diffraction techniques to produce an accurate three-dimensional structure of the target. This three-dimensional structure information can then be utilized to predict functionality and behavior of the target.

In theory, the crystallization process is simple. A target compound in pure form is dissolved in solvent. The chemical environment of the dissolved target material is then altered such that the target is less soluble and reverts to the solid phase in crystalline form. This change in chemical environment is typically accomplished by introducing a crystallizing agent that makes the target material less soluble, although changes in temperature and pressure can also influence solubility of the target material.

In practice however, forming a high quality crystal is generally difficult and sometimes impossible, requiring much trial and error and patience on the part of the researcher. Specifically, the highly complex structure of even simple biological compounds means that they are not amenable to forming a highly ordered crystalline structure. Therefore, a researcher must be patient and methodical, experimenting with a large number of conditions for crystallization, altering parameters such as sample concentration, solvent type, countersolvent type, temperature, and duration in order to obtain a high quality crystal, if in fact a crystal can be obtained at all.

Accordingly, there is a need in the art for methods and structures for performing high throughput screening of crystallization of target materials.

Microfluidic devices are defined as devices having one or more fluidic pathways, often called channels, microchannels, trenches, or recesses, having a cross-sectional dimension below 1000 µm, and which offer benefits such as increased throughput and reduction of reaction volumes. Interfacing microfluidic devices to macrosale systems, such as robotic liquid dispensing systems, has been challenging, often resulting in a loss of the number of reactions that can be carried out in parallel in a single microfluidic device. As a non-limiting example, Delucas discloses, among other things, using a microfluidic device to conduct nanoliter scale protein crystallization screening reactions in a parallel array format.

Unger discloses, among other things, microfluidic devices having an elastomeric block with a deflectable membrane. In one embodiment disclosed, which is depicted in FIGS. 1A and 1B, first elastomeric layer 1, having bottom surface 8 with microfabricated recess 2 formed therein, is bonded to top surface 7 of second elastomeric layer 3 having microfabricated recess 4 formed therein, to form an elastomeric block 5 having a first channel 6 formed from the recess 2 of the first elastomeric layer 1 being closed off by top surface 7 of second elastomeric layer 3, and where recess 4 of the second elastomeric layer is overlapped by first channel 6 formed, deflectable membrane 8 is formed by a portion of second elastomeric layer 3 separating first channel 6 from recess 4 of second elastomeric layer 3. Elastomeric block 5 may then be attached to substrate 9 so that recess 4 of second elastomeric layer 3 forms second channel 10 with a top surface of substrate 9. Fluid flow through second channel 10 may be controlled by actuating deflectable membrane 8 to deflect into and out of second channel 10. Deflectable membrane 8 may be actuated by increasing or decreasing the fluid pressure in first channel 6 to cause deflectable membrane 8 to deflect into or out of second channel 10, respectively. Alternatively, by increasing or decreasing the fluid pressure in second channel 10, deflectable membrane 8 can be deflected into or out of first channel 6, respectively.

FIG. 1C depicts the use of the device just described wherein liquid is introduced into second channel 10 through via 11, which was made by coring a fluid path from the top of the elastomeric block through first elastomeric layer 1 part of second elastomeric layer 3 into second channel 10. The fluid filling second channel 10 could then be partitioned by applying fluid pressure, such as gas pressure, through second via 13, which was made by coring through first elastomeric layer 1 into first channel 6 so that when the pressure was increased in first channel 6, deflectable membrane 8 deflected down into second channel 10 to contact the surface of substrate 9. Particular devices of Unger provide for high-density, reliable microfluidic devices in which the movement of fluid therein could be evoked and/or regulated by actuating the deflectable membrane to cause the membrane to function as part of a valve or pump.

An ideal application for microfluidic devices is screening for conditions that will cause a protein to form a crystal large enough for structural analysis. Protein crystallization is an important step in determining the structure of such proteins. Typically, reactions were set up by manually pipetting a solution containing a protein and a solution containing a protein crystallization reagent to cause the protein to form a crystal large enough to place in line with an X-ray source to perform X-ray diffraction studies. Determining the right conditions that will form a large enough crystal is often determined by seemingly countless trial and error experiments. Consequently, precious protein isolates are exceedingly limited in supply and therefore need to be judiciously used while screening for the right crystallization conditions. As a way to spare protein consumption during condition screening, efforts were made to reduce the volume of protein crystallization assays while increasing the number of experiments performed in parallel during the screen. Delucas discloses, among other things, methods and devices for carrying out nanoliter scale (nanoscale) protein crystallization experiments. In one embodiment disclosed, a microfluidic device is used to carryout nanoscale protein crystallization experiments in wells formed in a substrate.

Hansen discloses, among other things, microfluidic devices for carrying out protein crystallization reactions. Some of the embodiments disclosed in Hansen employ Unger's elastomeric block having deflectable membranes therein to regulate fluid flow. For example, a microfluidic device having a first chamber containing a solution of a protein is in fluid communication with a second chamber containing a solution containing a crystallizing agent that when contacted with the protein in the first chamber, may induce that protein to form crystals. In one example of many, the fluid communication between each chamber is through one or more channels. A valve situated between each of the chambers and in communication with the channel can be actuated to regulate the diffusion between the two chambers. The first chamber is in communication with a first inlet for introducing the solution containing the protein into the first chamber, and the second chamber agent is in communication with a second inlet for introducing the crystallization agent into that chamber.

Hansen discloses, among other things, a carrier for holding the microfluidic device of Hansen. An example of the Hansen carrier is shown in FIG. 2 where microfluidic structure 11000, which has several inlets and inlet rows such as well row 11012*a* and well row 11012*b*, sample inlet 11012*c* and containment valve control inlet 11012*d* and interface valve control inlet 11012*e*, is placed inside a frame base 11002 in receiving area 1106 having view window 1103 therein. Top frame 11014, which has pressure cavities 11026 and 11024 is placed upon frame base 11002 with microfluidic structure 11000 sandwiched between so that each pressure cavities seals against well rows 11012*a* and 11012*b* to form pressure chambers on top of each well row. In use, each well in well rows 11012*a* and 11012*b* are typically filled with different reagents for crystallizing proteins and sample inlet 11012*c* is loaded with a sample solution containing a protein to be crystallized. Containment valve control inlet 11012*d* and interface valve control inlet 11012*e* are typically filled with a liquid, such as an oil or water, to hydraulically actuate the valves in the microfluidic device. Pneumatic lines are inserted into control inlets 11012*d* and 11012*e* to apply pressurized gas in fluidic communication with the liquid contained within each control inlet channel within the microfluidic device, which in turn deflect membrane valve at certain intersections between the channels of the first elastomeric layer and the second elastomeric layer, as shown in FIG. 1.

Likewise, sample solution can be driven into a channel and on into chambers inside the microfluidic device by similarly applying gas pressure to the sample inlet 11012*c* to cause the sample solution to develop hydraulic pressure to move it through the channel into the chambers. Reagents loaded into wells of well row 11012*a* and 11012*b* can also be driven into their corresponding channels and on into chambers inside the microfluidic device by applying gas pressure to each of the pressure cavities. Once each of sample and reagent chambers within the microfluidic device have been filled, containment valves may be then closed by actuating deflectable membranes in communication with the inlet channel preceding the chamber to keep the sample and reagents inside their corresponding chambers. Meanwhile, an interface valves between each of the sample/reagent chamber pairs is kept closed to keep the reagent from diffusing into the sample and the sample from diffusing into the reagent chambers. After the filling of all chambers is complete, free interface diffusion can begin by opening the interface valves, while keeping the containment valves closed.

Protein crystallization experiments performed using the devices disclosed in Hansen may take several days to perform. As mentioned, the containment valves must be kept closed at all time to prevent sample or reagents from moving out of the chambers, potentially cross-contaminating each other. Accordingly, a source of pneumatic pressure to create a constant source of hydraulic pressure need be maintained to keep the containment valves closed. This can be done by having an "umbilical cord" connecting the carrier connected to a source of gas pressure such as a regulated gas supply. However, such umbilical cords may limit a user's ability to move a carrier about a laboratory, for example, into a refrigerator or incubator to achieve temperature control. Thus, there is a need for a system that would liberate a microfluidic device, such as those described by Hansen or Unger, from the apparent need for an umbilical cord to maintain valve actuation.

Schulte, et al. ("Schulte"), US Patent Publication No. 2003-0034306 A1, published on Feb. 20, 2003, entitled Well-Plate Microfluidics, which is hereby incorporated by reference for all purposes, discloses microfluidic devices, however, there are numerous and substantial differences between the invention disclosed herein and the devices of Schulte.

SUMMARY OF THE INVENTION

The present invention provides microfluidic devices and methods for their use. The invention further provides apparatus and systems for using the microfluidic devices of the invention, analyze reactions carried out in the microfluidic devices, and systems to generate, store, organize, and analyze data generated from using the microfluidic devices. The invention further provides methods of using and making microfluidic systems and devices which, in some embodiments, are useful for crystal formation.

The invention provides apparatus for operating a microfluidic device. In one embodiment, the apparatus includes a platen having a platen face with one or more fluid ports therein. The fluid ports spatially correspond to one or more wells on a surface of the microfluidic device. A platform for holding the microfluidic device relative to the platen is included, and a platen actuator for urging the platen against the microfluidic device so that at least one of the fluid ports of the platen is urged against one of the wells to form a pressure chamber comprising the well and the port, so that when pressurized fluid is introduced or removed into or from the pressure chamber through one of the ports, fluid pressure is changed therein.

In other embodiments, the apparatus includes a robotic platen actuator; the platen actuator is under electronic control by a controller; the controller is a computer or under computer control; the computer is following a program; the program was customized by a user of the apparatus; the microfluidic device includes first and second chambers in fluid communication with each other through a channel and a valve disposed along the channel which when opened or closed controls fluid communication between the first and second chambers, and wherein the valve is under the control of an automated valve actuating device when the microfluidic device is coupled to the platen; the automated valve actuating device is further under computer control; the valve is opened and closed using the automated valve actuating device; the valve comprises a deflectable membrane; and the platen actuator is adapted for delivering a pressurized fluid to the at least one fluid pressure port using a pressure between about one pound per square inch (1 psi) and about thirty-five pounds per square inch (35 psi).

The present invention further provides for microfluidic systems. One such system includes a microfluidic device having a plurality of chambers, with the microfluidic device coupled to a carrier and at least some of the plurality of chambers coupled to a plurality of inlets in the carrier. The system includes an interface plate adapted to engage at least one of the inlets in the carrier, a fluid source coupled to the interface plate and adapted to provide pressurized fluid to at least one of the inlets in the carrier, and a controller coupled to the fluid source and to the interface plate for directing fluid from the fluid source to the carrier.

In other embodiments, the microfluidic device further comprises a plurality of valve lines, and the fluid is directed into at least some of the valve lines by the controller; the controller is further adapted to open and close at least some of the valve lines; the carrier further comprises a plurality of wells, and wherein at least some of the wells are coupled to corresponding inlets of the plurality of inlets, the corresponding inlets being adapted to receive a fluid for analysis in the microfluidic device; the controller is adapted to apply a pressure through the interface plate to at least some of the plurality of wells in order to drive the fluid therein into at least some of the plurality of chambers; the interface plate comprises two or more separate interface plates each adapted to engage at least one inlet in the carrier; the carrier comprises an accumulator chamber having an accumulator port, and wherein the interface plate comprises a port that is in fluid communication with the accumulator chamber; the accumulator chamber further comprises a valve for controlling fluid movement into the accumulator chamber through the accumulator port, the valve being in fluid communication with the accumulator port; the valve permits fluid flow into the accumulator chamber through the accumulator port while restricting fluid flow out of the accumulator chamber through the accumulator port; the valve permits fluid flow out of the accumulator when the valve is actuated; the valve is actuated mechanically; the valve is a check valve; the interface plate comprises a valve actuator which is adapted to engage the valve when the interface plate and carrier are coupled; the accumulator chamber further comprises a liquid; the accumulator chamber further comprises a gas, or a gas and a liquid; the gas is pressurized relative to a gas pressure outside of the accumulator chamber; the interface plate further comprises a sealing gasket; the accumulator is adapted to maintain a pressure above a desired pressure level in order to a maintain a valve in the microfluidic device in a closed state; and the closed valve lasts for at least two (2) days.

The present invention further provides methods for conducting a step in a protein crystallization condition screening. In one embodiment, the method includes providing a microfluidic device and performing one of the steps from the group consisting of: robotically filling a well in the microfluidic device with a reagent, robotically moving the microfluidic device from a robotic liquid dispensing station to a different location, robotically placing the microfluidic device into the apparatus; removing the microfluidic device from the apparatus, robotically placing the microfluidic device into an optical inspection station, and optically interrogating the microfluidic device using an automated imaging system. Robotically means movement of the microfluidic device caused by a mechanical device under control of a computer or electronic controller.

The invention provides methods for crystallizing a protein. In one embodiment the method includes providing a microfluidic device having a first chamber having a dimension between 1000 μm and 1 μm, a second chamber having a dimension between 1000 μm and 1 μm, and a channel having a dimension between 1000 μm and 1 μm. The first and second chambers are in fluid communication with each other through the channel. A valve is disposed along the channel which, when actuated to open or close, controls fluid communication between the first and second chambers. The method includes introducing a crystallization reagent into the first chamber, introducing the protein in a solution into the second chamber, opening the valve so that the solution containing the protein in the second chamber becomes in fluid communication with the crystallization reagent in the first chamber, and closing the valve after a period of time to interrupt fluid communication between the first and second chambers.

In some embodiments, the method includes wherein the valve is under the control of an automated valve actuating device; the automated valve actuating device is further under computer control; the valve is opened and closed two or more times; the microfluidic device is a multilayer microfluidic device; the multilayer microfluidic device comprises at least one elastomeric layer and the valve is comprises a deflectable membrane; the two layers of the multilayer microfluidic device comprise an elastomeric material and may be bonded together to form an elastomeric block; the two or more layers of the multilayer microfluidic device comprise a first channel in a first layer, and a second channel in a second layer, wherein a portion of the first channel and a portion of the second channel overlap at an overlap region; the first and second channels are in fluid communication through a via located at the overlap region; the overlap region further comprises a deflectable membrane deflectable into either of the first or second channel to control fluid movement along the first or second channel; and the deflectable membrane is integral to either of the first or second layer.

The invention provides, in one aspect, for a microfluidic device, comprising: a first elastomeric layer having a recess with a width dimension between 0.1 µm and 1000 µm, a second elastomeric layer having a recess with a width dimension between 0.1 µm and 1000 µm, and a top surface, wherein the first elastomeric layer is bonded to the top surface of the second elastomeric layer to form an elastomeric block having a deflectable portion therein, the elastomeric block having a bottom surface defining a surface area, and the elastomeric block having a height, a substrate having a recess therein and a first surface, the substrate having a port in the first surface of the substrate, the port being in fluid communication with the recess of the substrate, wherein the elastomeric block is attached to the substrate to form the microfluidic device without the elastomeric block occluding the port.

In some embodiments, the port is a well having an opening in the first surface of the substrate, the elastomeric block not occluding the well opening when attached to the substrate, the substrate further comprises a second surface different than the first surface of the substrate, and wherein the elastomeric block is attached to the second surface of the substrate, the first surface is a top surface of the substrate and the second surface is a bottom surface of the substrate, the elastomeric block is attached to the first surface of the substrate without the elastomeric block occluding the port, the port is a well, the well has a wall having a height that extends above the first surface of the substrate where the elastomeric block is attached to the substrate, the well wall height is coextensive with the elastomeric block height, the well wall height is less than the elastomeric block height, the well wall height is greater that the elastomeric block height, the recess is a plurality of recesses and the port is a plurality of ports, wherein each port is in fluid communication with at least one of the plurality of recesses of the substrate, at least one of the plurality of ports is a well, the well defines a volume between 0.1 µl and 400 µl, the well defines a volume between 0.1 µl and 250 µl, the well defines a volume between 0.1 µl and 100 µl, the well defines a volume between 0.1 µl and 10 µl, at least one recess of the plurality of recesses of the substrate has a at least one region having a cross-sectional dimension between 0.1 µm and 1000 µm, at least one of the plurality of recesses of the substrate has a at least one region having a cross-sectional dimension between 0.1 µm and 500 µm, the recesses of the substrate has a at least one region having a cross-sectional dimension between 0.1 µm and 100 µm, at least one of the plurality of recesses of the substrate has a cross-sectional dimension between 0.1 µm and 10 µm, and/or where the substrate comprises a polymer, the substrate comprises a polymer is selected from the group consisting of polymethylmethacrylate, polystyrene, polypropylene, polyester, fluoropolymers, polytetrafluoroethylene, polycarbonate, polysilicon, and polydimethylsiloxane, the substrate comprises glass or quartz, the substrate further comprises a sealing layer attached to the substrate for sealing the recesses to form a channel from the recess, the sealing layer comprises a film, the film is attached by an adhesive, the film is an adhesive film having adhesive thereon prior to attachment of the film to the substrate, the elastomeric block further comprises a via, the via provides fluid communication between the recess in the substrate and the recess in the first elastomeric layer, the via was formed by coring the elastomeric block, the via was formed by drilling the elastomeric block, the via was formed by ablation, the ablation was achieved using a laser beam, the laser beam was generated by an excimer laser, the via was formed by etching one of the first or second elastomeric layers, the via is formed one of the first or second elastomeric layers prior to forming the elastomeric block, the recess in the elastomeric layer overlaps the recesses of the second elastomeric layer, wherein the deflectable portion of the elastomeric block is formed from the second elastomeric layer where the recess of the second elastomeric layer is overlapped by the recess of the first elastomeric layer to form a deflectable membrane separating the recesses of the first elastomeric layer from the recess of the second elastomeric layer, the recess of the substrate and the via and the recess in the first elastomeric layer contain a fluid, the fluid, when at a pressure different than a pressure of a second fluid in the recess of the second layer, actuates the deflectable membrane causing the deflectable membrane to deflect into one of the recess of first elastomeric layer or the recesses of the second elastomeric layer, the via is formed by a process using a robotic device movable in x and y dimensions, the robotic device comprises an x,y movable stage, at least one of the first and second elastomeric layers comprises an elastomeric material having a Young's modulus between 1000 Pa and 1,000,000 Pa, at least one of the first and second elastomeric layers comprises an elastomeric material having a Young's modulus between 10,000 Pa and 1,000,000 Pa, at least one of the first and second elastomeric layers comprises an elastomeric material having a Young's modulus between 100,000 Pa and 1,000,000 Pa, at least one of the first and second elastomeric layers comprises an elastomeric material having a Young's modulus between 360,000 Pa and 870,000 Pa, at least one of the elastomeric layers comprises polydimethylsiloxane, at least one of the elastomeric layers comprises a polymer made from a two-part polymer forming material, at least one of the elastomeric layers has been plasma etched, the elastomeric block contacts the substrate, the elastomeric block is bonded to the substrate, between the elastomeric block and the substrate further comprises a gasket, the elastomeric block is glued to the substrate, the port is in fluid communication with an accumulator chamber, the accumulator chamber has an accumulator port for introducing fluid into the accumulator chamber, the accumulator chamber further comprises a valve for controlling fluid movement into the accumulator chamber through the accumulator port, the valve being in fluid communication with the accumulator port, the valve permits fluid flow into the accumulator chamber through the accumulator port while restricting fluid flow out of the accumulator chamber through the accumulator port, the valve permits fluid flow out of the accumulator when the valve is actuated, the valve is actuated mechanically, the valve is a check valve, the accumulator further comprises a liquid, the accumulator chamber further comprises a gas, the accumulator further comprises a gas and a liquid, the gas is pressurized relative to a gas pressure outside of the accumulator chamber, the port is a plurality of ports, and the recess in the substrate is a plurality of recesses in the substrate, each of the plurality of ports being in fluid communication with at least one of the plurality of recesses, each of the plurality of ports are in fluidic communication with one of a plurality of wells, the wells each have an opening in the first surface, the elastomeric block not occluding the well opening when attached to the substrate, the well openings have a center point, and the plurality of wells is spatially arranged such that the center-to-center spacing of each well is that of the center-point spacing of a microtiter plate having a format selected from the group of a 96 well microtiter plate, a 384 well microtiter plate, a 864 well microtiter plate, a 1536 well microtiter plate, and a 6144 well microtiter plate, the well openings have a center point, and the plurality of wells is spatially arranged such that the center point-to-center point spacing is about 4.5 mm.

Another aspect of the invention provides for a microfluidic device comprising: a first layer having therein a first recess; a second layer having a second layer top surface and a second recess therein; a substrate layer having a top surface, wherein the first layer is bonded to the second layer such that a first channel is formed from the first recess and the second layer top surface, and the second layer is bonded to the substrate such that a second channel is formed from the second recess and the substrate top surface, and a portion of the first channel overlaps a portion of the second channel to form a channel overlap; and, a first channel-second channel via establishing fluid communication between the second channel and the first channel at the channel overlap, wherein the first channel-second channel via is formed after the first layer and the second layer are bonded together to form a microfluidic block.

In other aspects, the first channel-second channel via extends from the second channel and through and beyond the first channel; the first channel-second channel via is formed by laser ablation; at least one or at least two of the layers comprises an elastomer; the substrate comprises a polymer, glass, or quartz; the polymer is selected from the group consisting of polymethylmethacrylate, polystyrene, polypropylene, polycarbonate, polysilicon, and plastic; the second layer further comprises a third channel formed from a third recess in the second layer and the top surface of the substrate wherein a portion of the third channel and a second portion of the first channel overlap to form a second overlap and wherein the third channel and the second channel are in fluid communication through a first channel-third channel via located at the second overlap; the first channel-second channel via is formed after the first layer and second layer are bonded; the substrate further comprises a substrate recess, a portion of which is overlapped by a portion of the first channel to form a first channel-substrate channel overlap; a sealing layer having a top surface bonded to the substrate such that at least one of the substrate recesses forms a substrate channel; and a first channel-substrate channel via located at the first channel-substrate channel overlap, wherein the first channel and the substrate channel are in fluid communication through the first channel.

Another aspect of the invention provides for increasing the density of reactions within a microfluidic device by interconnecting channels located within different layers of the microfluidic device, wherein said interconnections are made using vias, preferably vias formed after two or more layers containing channels are bonded together, more preferably by forming the vias using a laser ablation tool.

The invention provides, in one aspect, for a carrier for holding a microfluidic device comprising: a housing, the housing defining a chamber therein and having a receiving portion for receiving the microfluidic device; a connection block for retaining the microfluidic device, wherein the connection block is attachable to the microfluidic device through one or more prongs, and the microfluidic device, when retained by the connection block, is insertable into the receiving portion of the housing.

Other embodiments include having the one or more prongs be two or more prongs, having at least one of the one or more prongs is a tube, having the receiver has at least one slot for guiding and retaining the microfluidic device when inserted into the receiving portion, having the receiver further comprises one or more pipette supports for guiding a pipette tip into the microfluidic device when inserted into the receiving portion, including one or more accumulators for providing fluid under pressure to the microfluidic device when inserted into the receiving portion, preferably where at least one accumulator further comprises a check valve, having the housing comprises a housing base and a housing cover, preferably where an accumulator is attached to the housing, and preferably where the housing cover and the housing base are sealed together by a gasket, including a humidity control material within the housing for providing humidity control, preferably where the humidity control material is selected from the group consisting of a sponge, a gel matrix, a desiccant, and a woven material, having the housing is preferably be made from a polymer, more preferably where the polymer is either polycarbonate or acrylic or polystyrene, preferably where the accumulator is in fluid communication with the connection block through one or more accumulator-connection block tubes, wherein the accumulator-connection block tubes are preferably flexible, having a first tube of the one or more tubes is in communication with the microfluidic device for controlling one or more first valves, preferably wherein a second tube of the one or more tubes is in communication with the microfluidic device for controlling one or more second valves, for example, but not limited to, wherein the first valves are interface valves and/or wherein the second valves are containment valves.

In another embodiment, the present invention provides a device for positioning protein crystal within an energy beam comprising a chip for holding the crystal therein, the chip being made from an elastomeric block having disposed therein a deflectable membrane. The device includes an adapter plate for connecting the chip to a post, the chip being connected to the adapter plate through one or more posts penetrating into the chip, and a goniometer, wherein the post is connected to the post for positioning the crystal within the beam. In other aspects, the adapter plate is movably translatable so as to further position the crystal within an axis perpendicular to the beam; and the goniometer is rotatable about an axis perpendicular and intersecting the beam, and the chip is rotated about the axis of the beam so as to expose different facets of the crystal to the beam.

BRIEF DESCRIPTION OF THE DRAWINGS

FIG. 9C is a cross sectional view of a via for use in some embodiments of microfluidic devices of the present invention;

FIG. 13 is a rear plan view of fluidic routing within a plate interface or platen according to an embodiment of the present invention;

DETAILED DESCRIPTION OF THE PREFERRED EMBODIMENTS

Figure 1A:
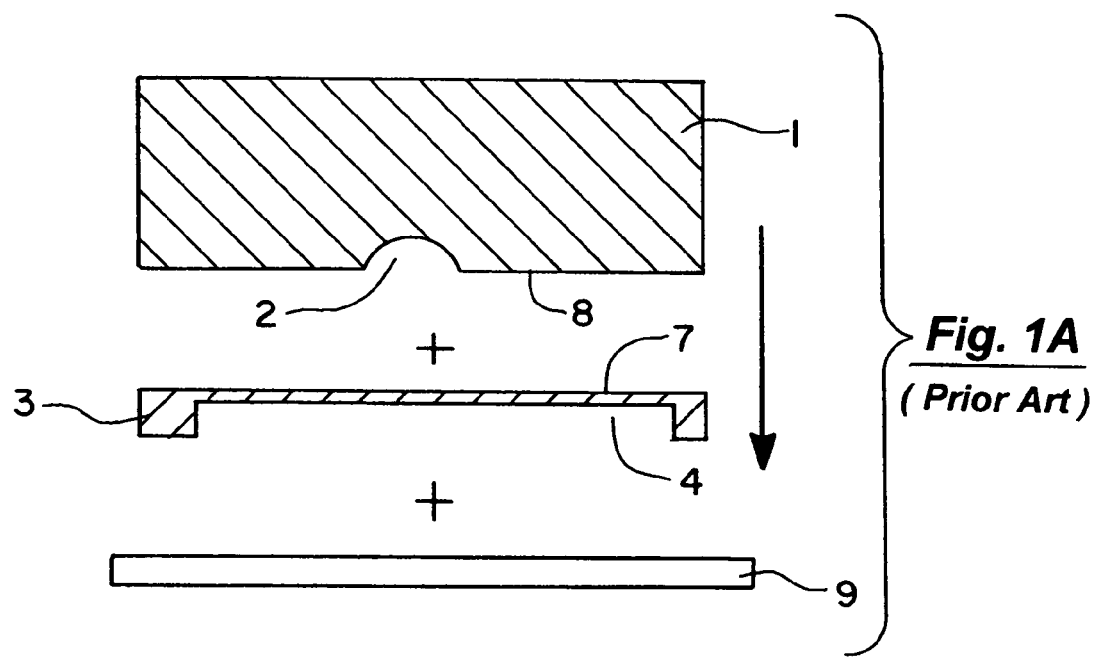
FIGS. 1A-1C are simplified cross-sections of prior art elastomeric blocks.
Figure 1B:
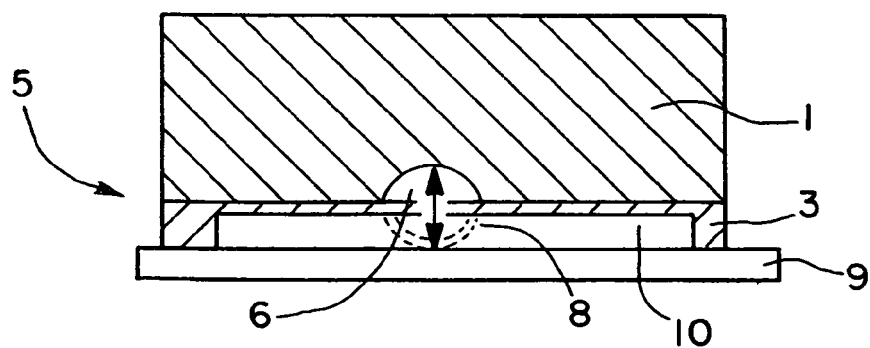
Figure 1C:
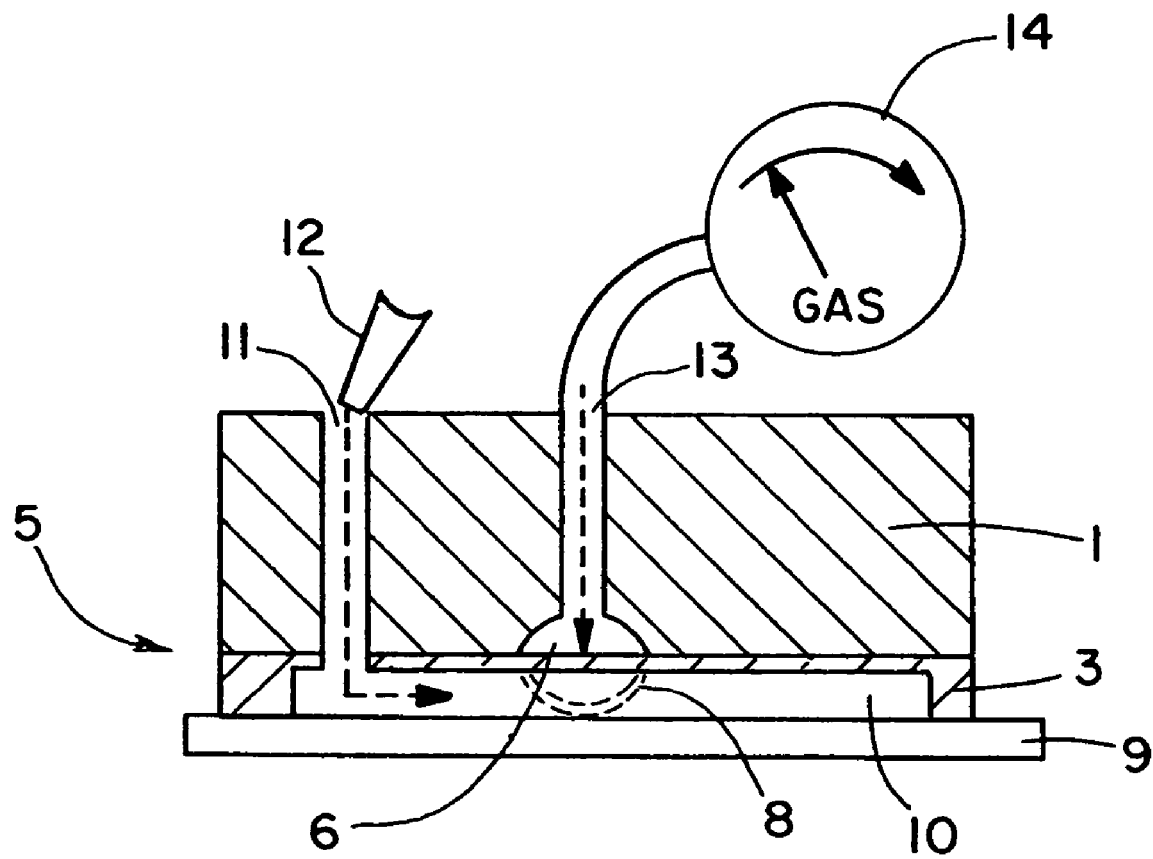
Figure 2:
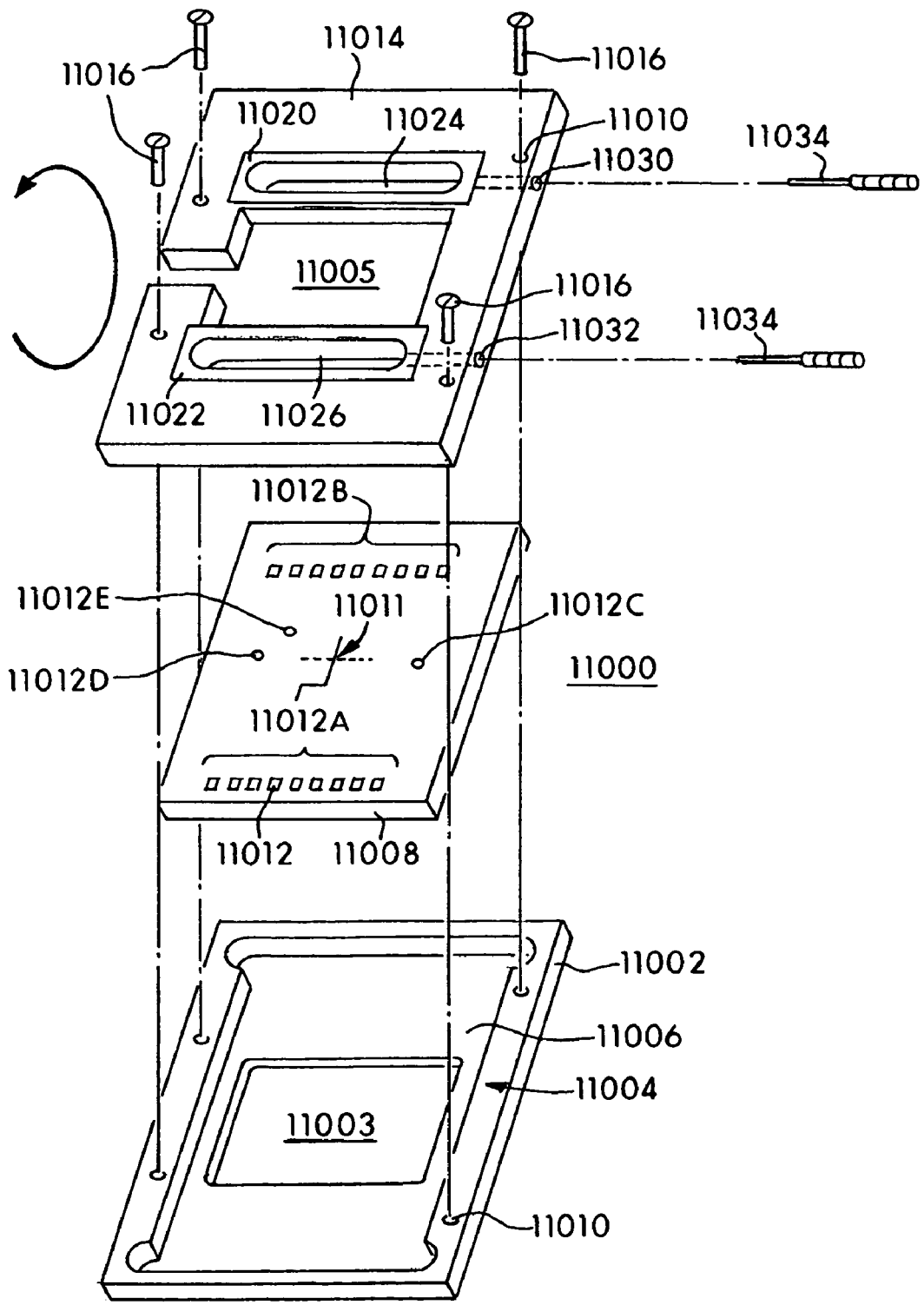
FIG. 2 is a an exploded view of a prior art carrier and microfluidic device.

Systems of the present invention will be particularly useful for metering small volumes of material in the context of performing crystallization of target material. A host of parameters can be varied during such crystallization screening. Such parameters include but are not limited to: 1) volume of crystallization trial, 2) ratio of target solution to crystallization solution, 3) target concentration, 4) cocrystallization of the target with a secondary small or macromolecule, 5) hydration, 6) incubation time, 7) temperature, 8) pressure, 9) contact surfaces, 10) modifications to target molecules, 11) gravity, and (12) chemical variability. Volumes of crystallization trials can be of any conceivable value, from the picoliter to milliliter range.

The length of time for crystallization experiments can range from minutes or hours to weeks or months. Most experiments on biological systems typically show results within 24 hours to 2 weeks. This regime of incubation time can be accommodated by the microfluidics devices in accordance with embodiments of the present invention.

The temperature of a crystallization experiment can have a great impact on success or failure rates. This is particularly true for biological samples, where temperatures of crystallization experiments can range from 0-42° C. Some of the most common crystallization temperatures are: 0, 1, 2, 4, 5, 8, 10, 12, 15, 18, 20, 22, 25, 30, 35, 37, and 42. Microfluidics devices in accordance with embodiments of the present invention can be stored at the temperatures listed, or alternatively may be placed into thermal contact with small temperature control structures such as resistive heaters or Peltier cooling structures. In addition, the small footprint and rapid setup time of embodiments in accordance with the present invention allow faster equilibration to desired target temperatures and storage in smaller incubators at a range of temperatures.

Embodiments of microfluidic structures in accordance with the present invention may be employed for applications other than crystallization screening. Examples of such applications include those described in PCT application PCT/US01/44869, filed Nov. 16, 2001 and entitled "Cell Assays and High Throughput Screening", hereby incorporated by reference for all purposes. Examples of microfluidic structures suitable for performing such applications include those described herein, as well as others described in U.S. patent application Ser. No. 10/118,466, entitled Nucleic Acid Amplification Utilizing Microfluidic Devices, filed Apr. 5, 2002, the complete disclosure of which is hereby incorporated by reference for all purposes.

An embodiment of a method of fabricating a microfluidic device in accordance with the present invention comprises etching a top surface of a glass substrate to produce a plurality of wells, molding an elastomer block such that a bottom surface bears a patterned recess, placing a bottom surface of the molded elastomer block into contact with the top surface of the glass substrate, such that the patterned recess is aligned with the wells to form a flow channel between the wells.

An embodiment of a method for forming crystals of a target material comprises priming a first chamber of an elastomeric microfluidic device with a first predetermined volume of a target material solution. A second chamber of an elastomer microfluidic device is primed with a second predetermined volume of a crystallizing agent. The first chamber is placed into fluidic contact with the second chamber to allow diffusion between the target material and the crystallizing agent, such that an environment of the target material is changed to cause formation of crystal.

In yet another aspect, chambers or metering cells may be formed in a first elastomer layer, said chambers or metering cells being in fluid communication through fluid channels, and a second layer having formed therein control channels, wherein deflectable membranes between the first and second layers are deflectable into the first layer to control fluid flow through the fluid channels. A substrate may be mated to the first and second layers to impart rigidity or provide for additional fluidic interconnections. The microfluidic devices then may be used in conjunction with carriers and/or systems for providing process control as further detailed herein.

The present invention provides for microfluidic devices and methods for their use. The invention further provides for apparatus for using the microfluidic devices of the invention, analyze reactions carried out in the microfluidic devices, and systems to generate, store, organize, and analyze data generated from using the microfluidic devices. Devices, systems and methods of the present invention will be particularly useful with various microfluidic devices, including without limitation the Topaz® series of devices available from Fluidigm, Corporation of South San Francisco, Calif. The present invention also will be useful for other microfabricated fluidic devices utilizing elastomer materials, including those described generally in U.S. patent application Ser. No. 09/826,583 filed Apr. 6, 2001 and entitled Microfabricated Elastomeric Valve and Pump Systems; Ser. No. 09/724,784, filed Nov. 28, 2000 and entitled Microfabricated Elastomeric Valve and Pump Systems; and Ser. No. 09/605,520, filed Jun. 27, 2000 and entitled Microfabricated Elastomeric Valve and Pump Systems. These patent applications are hereby incorporated by reference.

High throughput screening of crystallization of a target material, or purification of small samples of target material by recrystallization, is accomplished by simultaneously introducing a solution of the target material at known concentrations into a plurality of chambers of a microfabricated fluidic device. The microfabricated fluidic device is then manipulated to vary solution conditions in the chambers, thereby simultaneously providing a large number of crystallization environments. Control over changed solvent conditions may result from a variety of techniques, including but not limited to metering of volumes of a crystallizing agent into the chamber by volume exclusion, by entrapment of liquid volumes determined by the dimensions of the microfabricated structure, or by cross-channel injection into a matrix of junctions defined by intersecting orthogonal flow channels.

Crystals resulting from crystallization in accordance with embodiments of the present invention can be utilized for x-ray crystallography to determine three-dimensional molecular structure. Alternatively, where high throughput screening in accordance with embodiments of the present invention does not produce crystals of sufficient size for direct x-ray crystallography, the crystals can be utilized as seed crystals for further crystallization experiments. Promising screening results can also be utilized as a basis for further screening focusing on a narrower spectrum of crystallization conditions, in a manner analogous to the use of standardized sparse matrix techniques.

Systems and methods in accordance with embodiments of the present invention are particularly suited to crystallizing larger biological macromolecules or aggregates thereof, such as proteins, nucleic acids, viruses, and protein/ligand complexes. However, crystallization in accordance with the present invention is not limited to any particular type of target material. Further, while embodiments of the present invention discussed utilize diffusion of crystallizing agent in the liquid phase, vapor diffusion is another technique that has been employed to induce crystal formation.

Embodiments of microfluidic devices in accordance with the present invention may utilize on-chip reservoirs or wells. However, in a microfluidic device requiring the loading of a large number of solutions, the use of a corresponding large number of input tubes with separate pins for interfacing each well may be impractical given the relatively small dimensions of the fluidic device. In addition, the automated use of pipettes for dispensing small volumes of liquid is known, and thus it therefore may prove easiest to utilize such techniques to pipette solutions directly on to wells present on the face of a chip.

Capillary action may not be sufficient to draw solutions from on-chip wells into active regions of the chip, particularly where dead-ended chambers are to be primed with material. In such embodiments, one way of loading materials into the chip is through the use of external pressurization. Again however, the small dimensions of the device coupled with a large number of possible material sources may render impractical the application of pressure to individual wells through pins or tubing.

Figure 3:
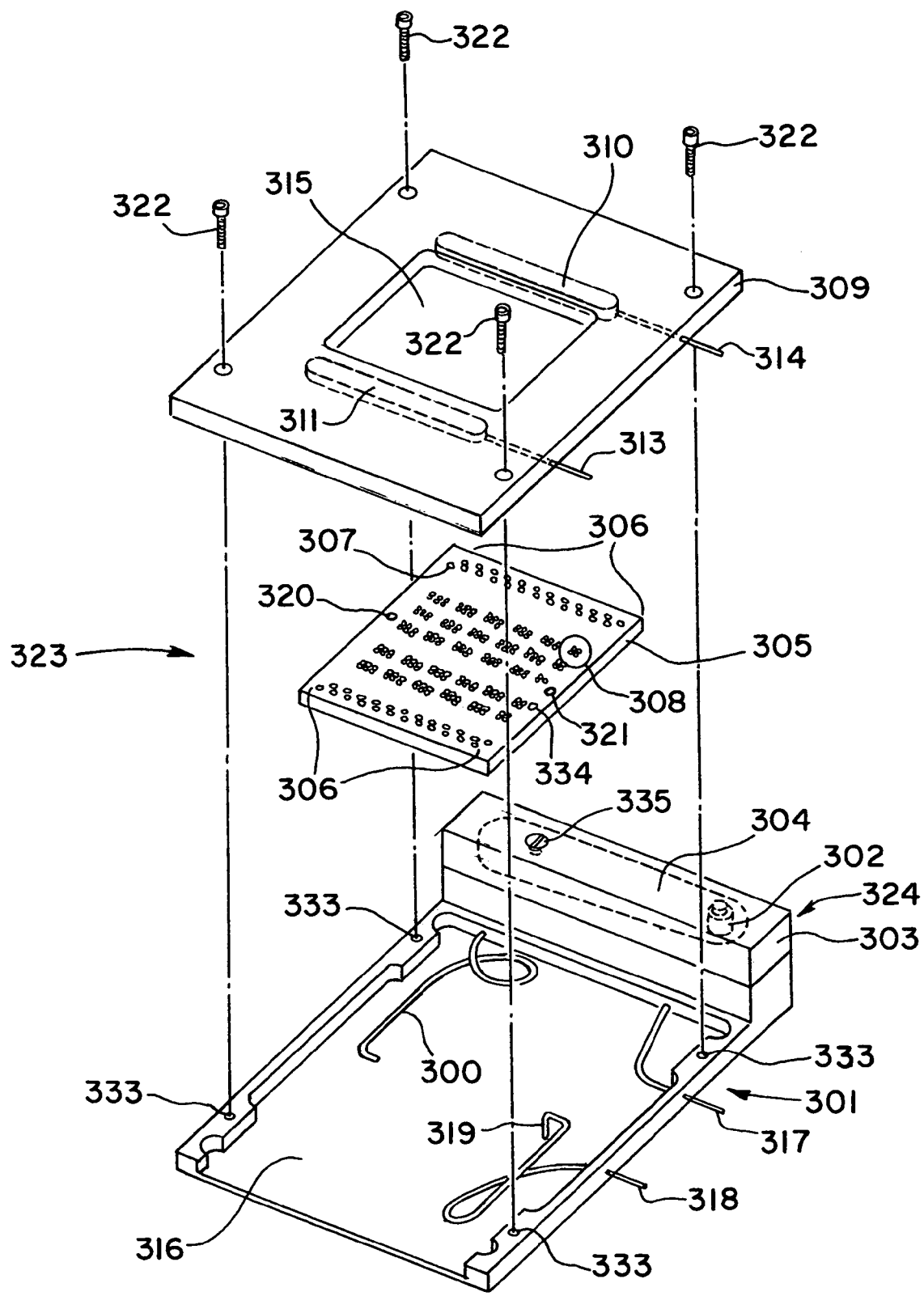
FIG. 3 is an exploded view of a carrier and microfluidic device according to an embodiment of the present invention.

Turning now to FIG. 3, a microfluidic device according to an embodiment of the present invention will be described having one or more integrated fluid pressure storage chambers or accumulators to provide a source of fluid pressure to one or more deflectable membranes within the microfluidic device. FIG. 3 depicts a preferred embodiment of a carrier 323 with an integrated pressure accumulator. Carrier 323 comprises a carrier base 301 which has a receiving area 300 for receiving and maintaining the position of a microfluidic device 305 inside carrier 323. Microfluidic device 305 may be a wide range of devices within the scope of the present invention, including Topaz® 1.96 and Topaz® 4.96 chips available from Fluidigm Corporation.

Microfluidic device 305 comprises one or more well rows 306 having one or more inlet wells 307 that are in fluid communication with channels inside microfluidic device 305, a containment valve inlet 320, an interface valve inlet 321, and a sample inlet 324. A carrier top 309 includes pressure cavities 310 and 311 which are positioned in contact with well rows 306 to form a common pressure chamber over each well 307 for each well row 306. Pressure chamber inlets 313 and 314 are used to supply gas pressure to each pressure chamber when formed with each pressure cavity contacting the surface of microfluidic device 305.

Carrier 323 further includes a pressure accumulator 324 which is preferably formed by attaching an accumulator top portion 303 to a portion of carrier base 301 forming an accumulator chamber 304 therein. Fluid, preferably gas, is introduced into accumulator chamber 304 through an accumulator inlet 317 which is in fluid communication with accumulator chamber 304. Preferably, an accumulator check valve 302 is placed in-line between accumulator inlet 317 and accumulator chamber 304 to maintain fluid pressure within accumulator chamber 304 even after the disconnection of a fluid pressure source (not shown) from accumulator inlet 317. Preferably, accumulator check valve 302 is housed in a "drywell" inside of accumulator chamber 304 when gas is used to pressurize accumulator chamber 304 while a portion of accumulator chamber 304 contains a liquid to create hydraulic pressure with the liquid contained therein. The liquid, under hydraulic pressure, can be in turn used to actuate a deflectable portion, such as a membrane, preferably a valve membrane, inside of microfluidic device 305 by supplying hydraulic pressure through an accumulator outlet 316 that is in fluid communication with accumulator chamber 304 and at least one channel within microfluidic device 305.

In the embodiment shown in FIG. 3, carrier top 309 is attached to carrier base 301 by one or more screws 309 being threaded into corresponding one or more screw holes 333 of carrier base 301 so that a compressive force is maintained between carrier top 309 and the top surface of microfluidic device 305 so that pressure cavities 310 and 311 form fluid tight seals around well rows 306. An interface pressure supply line inlet 318 connects to an interface pressure supply line 319 which is also inserted into interface valve inlet 321 of microfluidic device 305 to provide a source of pressurized fluid, preferably gas, or hydraulic pressure to a second channel within microfluidic device 305 to actuate at least one second deflectable portion, preferably a deflectable membrane of a second interface valve, within microfluidic device 305. One or more metering cells 308 within microfluidic device 305 are in fluid communication with well inlets 307 and a sample inlet 334. In some embodiments, a protein crystallization metering cell, such as one described in Hansen, is provided, wherein a first and a second chamber are in fluid communication through one or more interface channels therebetween, wherein the interface channels further comprise an interface valve for controlling diffusion or fluid movement between each chamber. Each chamber is further in fluid communication with an inlet for introducing a fluid into each chamber, the inlets being in fluid communication with the chambers through channels inside the microfluidic device.

One method of using carrier 323 according to the present invention will be described. With carrier top 309 off, wells 307 are filled with reagents. A sample solution is injected into sample inlet 334 using a micropipettor. The interface valve within each metering cell 308 is closed by applying pressure to interface valve inlet 321 through interface pressure supply line 319. The sample solution may be further moved inside of microfluidic device 305 by further applying pressure (e.g., in the form of gas pressure) into sample inlet 334 to push the sample solution into the sample reagent of metering cell 308. Hydraulic liquid, preferably water, more preferably oil, still more preferably Krytox(R) GL100(tm) oil, which is polyhexafluoropropylene oxide, or a blend of oils and other solvents, such as water, is introduced into interface valve inlet 320 and containment valve inlet 321, preferably by using a micropipettor. Containment line 300 and control line 319 are inserted into inlets 320 and 321, respectively, and carrier top 309 is affixed to carrier base 301 with microfluidic device 305 therebetween.

Figure 4:
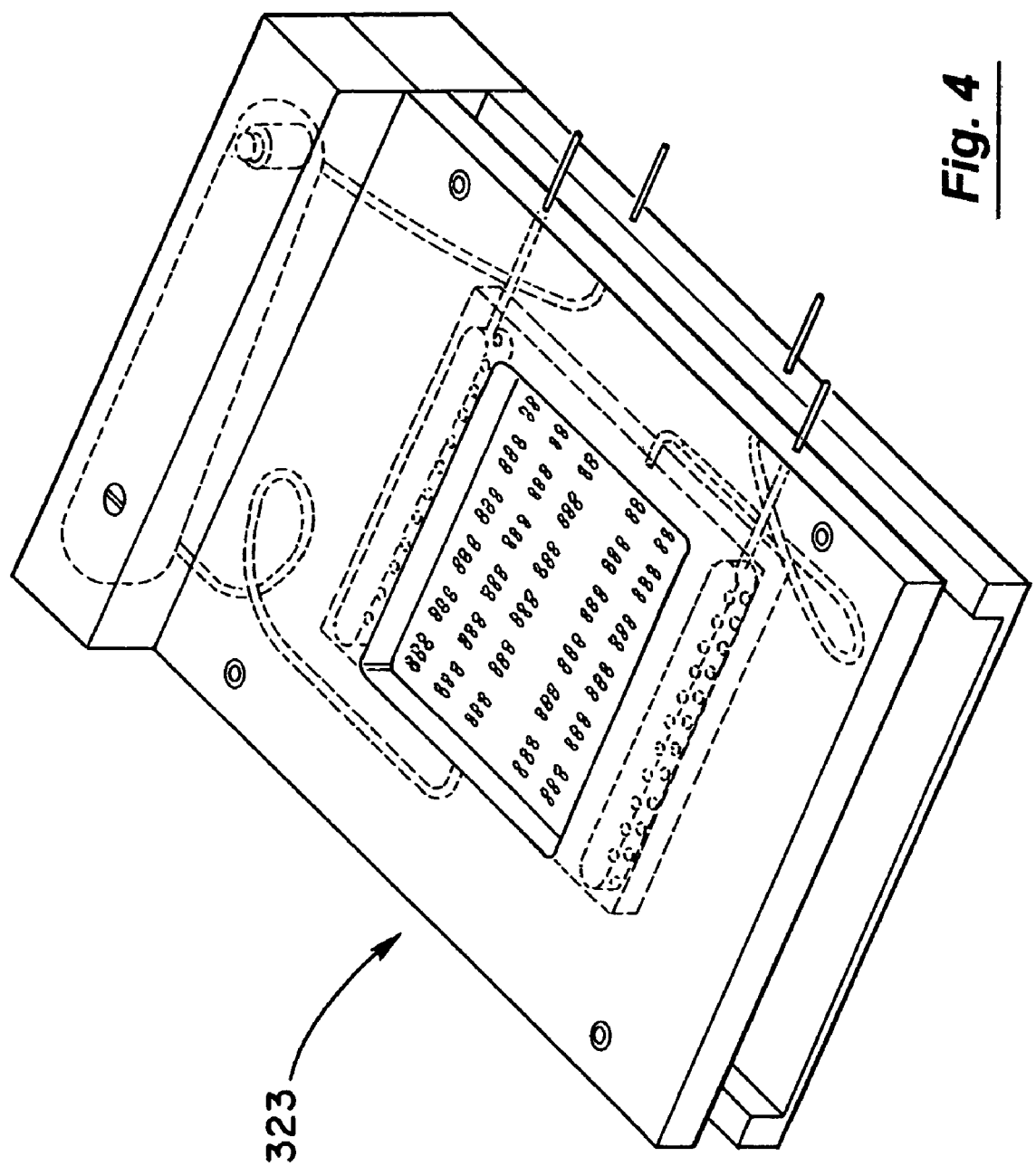
FIG. 4 depicts a perspective view of a carrier according to an embodiment of the present invention.
Figure 5:
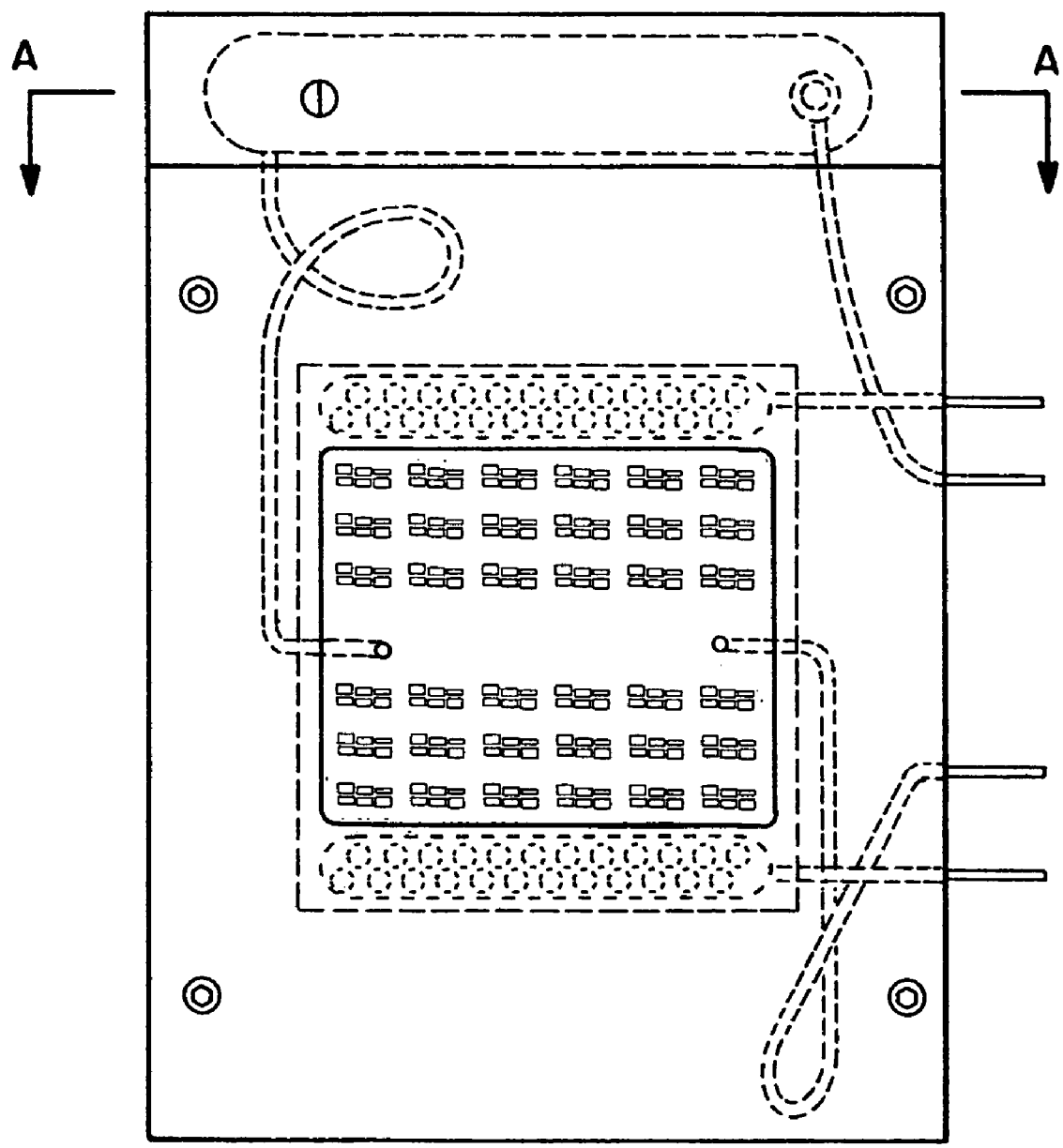
FIG. 5 depicts a plan view of the carrier shown in FIGS. 3 and 4.
Figure 6:
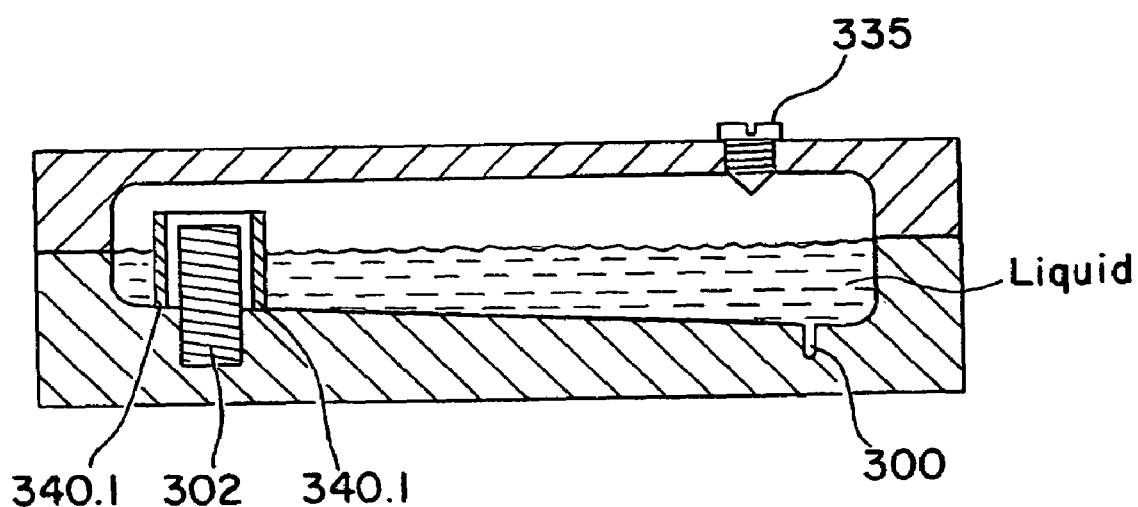
FIG. 6 depicts a cross-sectional view of the accumulator chamber of the carrier shown in FIGS. 3-5.

FIG. 4 depicts a perspective view of carrier 323 shown in FIG. 3. FIG. 5 depicts a plan view of the carrier shown in FIGS. 3 and 4. FIG. 6 depicts a cross-sectional view of accumulator chamber 304 inside accumulator 324 showing an angled chamber floor angled downward with respect to accumulator chamber cover 303 which permits liquid to drain towards line 300, and also shows access screw 335 which can be removed for adding or removing fluids, preferably liquids as shown partially occupying accumulator chamber 304. A side view of check valve 302 is shown situated inside of dry-well 340 defined by dry-well wall(s) 340.1.

Figure 7:
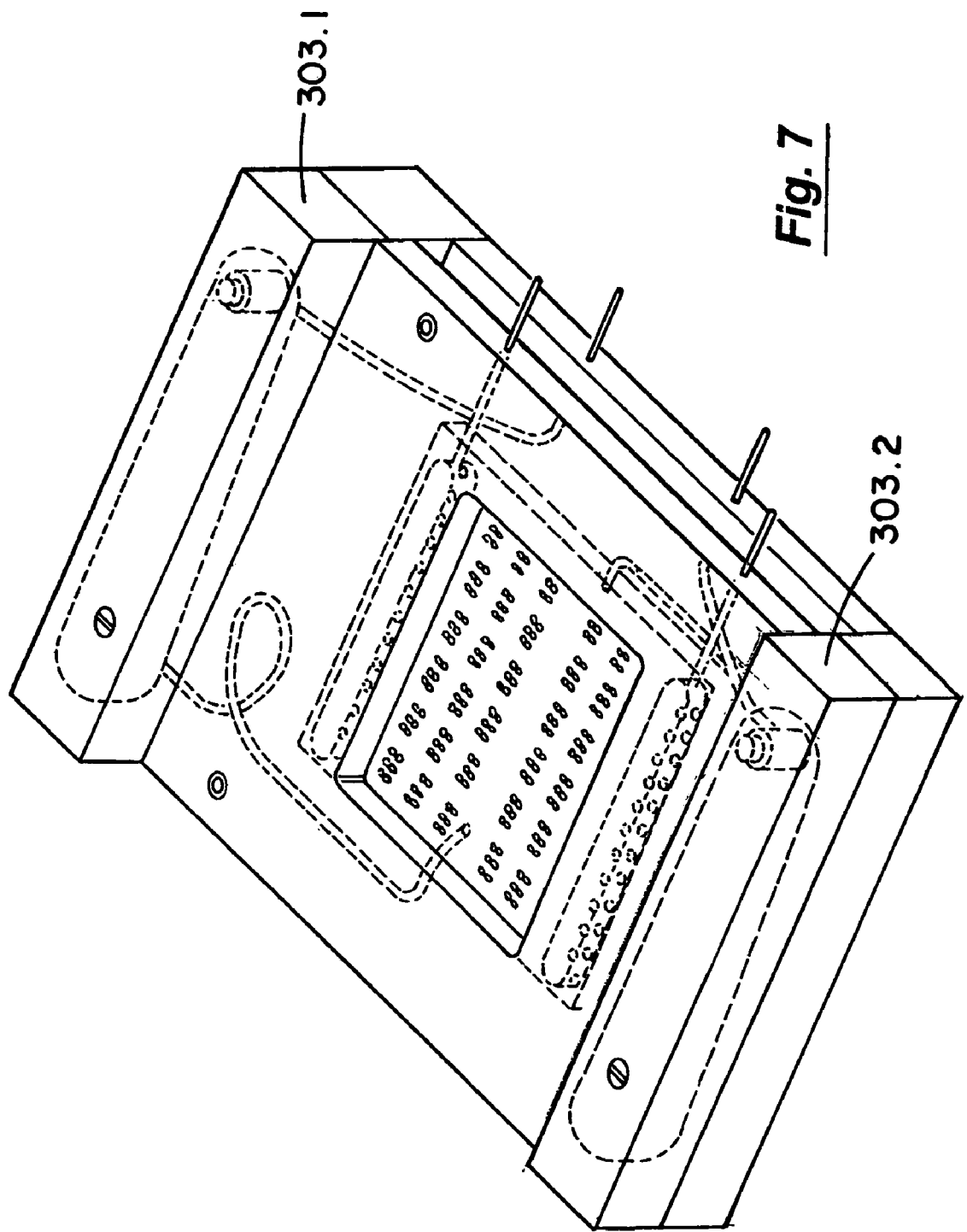
FIG. 7 is a perspective view of another carrier according to an embodiment of the present invention.

FIG. 7 depicts a carrier similar to the carrier shown in FIGS. 3-6, however, instead of a single accumulator being present, two separate accumulators 303.1 and 303.2 are integrated into the carrier. In a preferred use, the second accumulator is used to actuate, and maintain actuation of a second deflectable portion of the microfluidic device, preferably a second deflectable membrane valve. In a particularly preferred embodiment, the first accumulator is used to actuate interface valves within a metering cell, and the second accumulator is used to actuate containment valves within a metering cell, independent of each other. In yet other embodiments, a plurality of accumulators may also be included to provide for independent actuation of additional valve systems or to drive fluid through a microfluidic device.

Figure 8A:
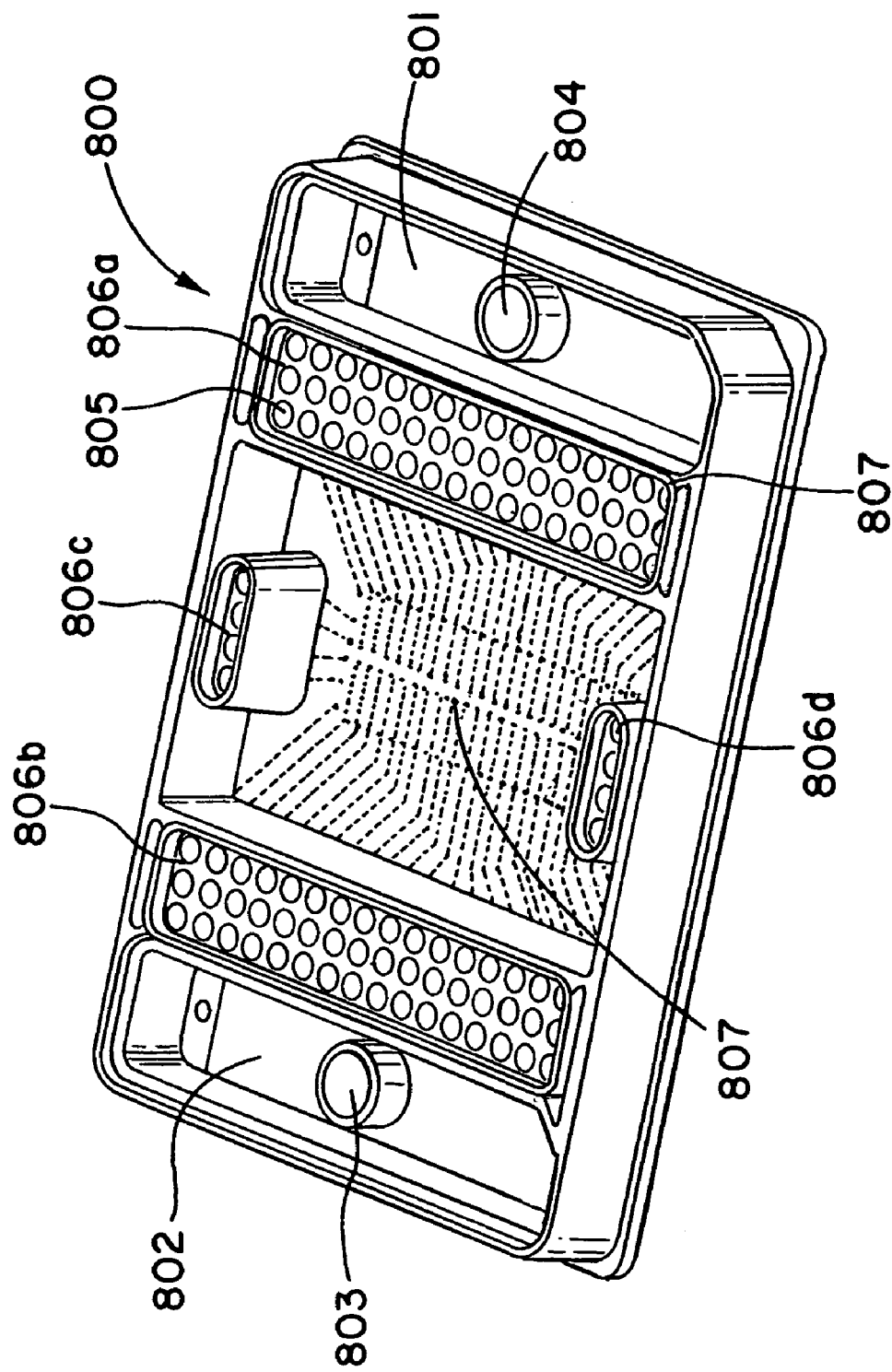
FIG. 8A depicts a substrate of a microfluidic device that has integrated pressure accumulator wells according to an embodiment of the present invention.
Figure 8B:
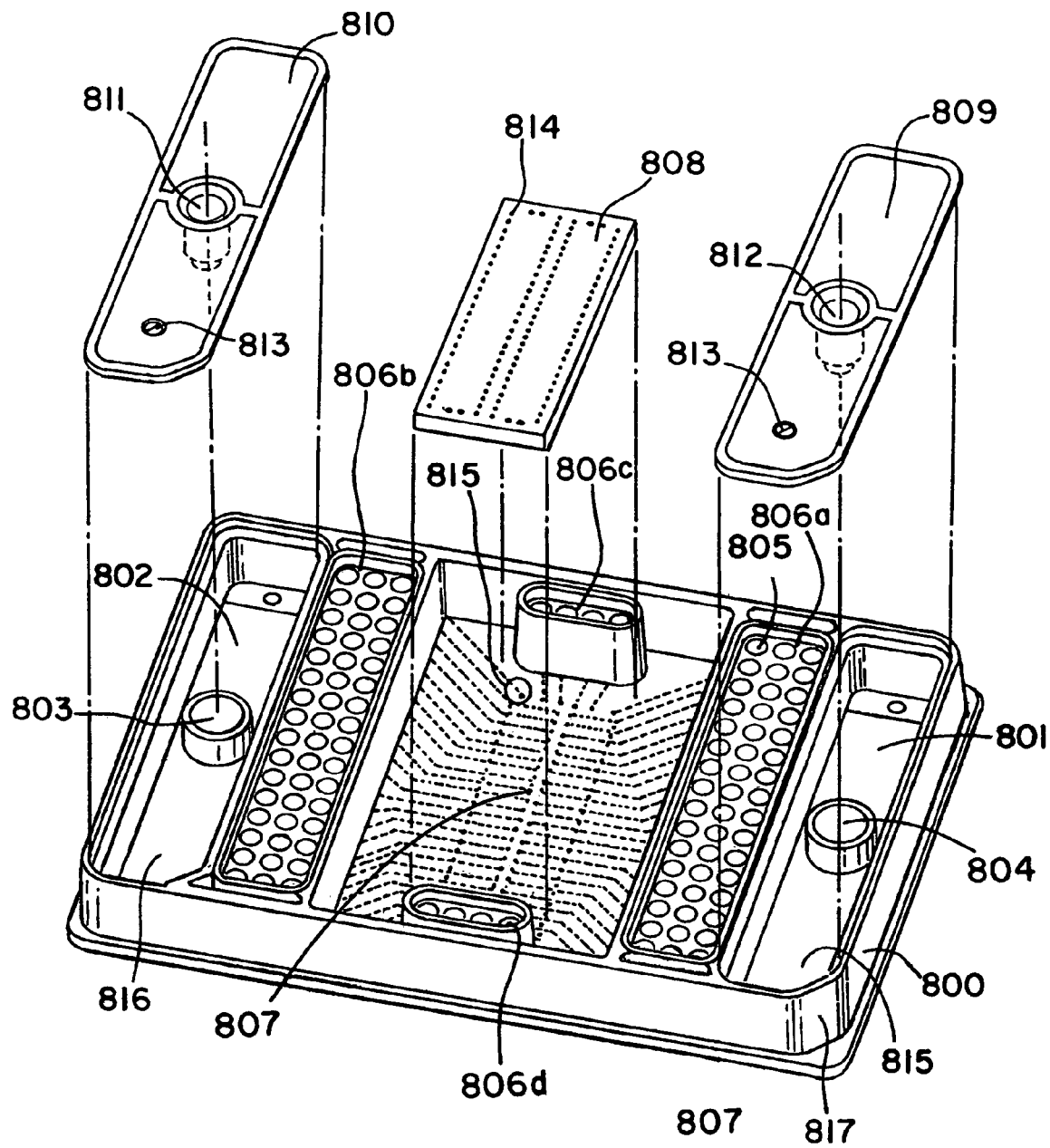
FIG. 8B depicts an exploded view of the microfluidic device shown in FIG. 8A, and further including an elastomeric block.

In an alternative embodiment of the present invention, FIG. 8A depicts a substrate 800 of a microfluidic device that has integrated pressure accumulator wells 801 and 802, each having therein a drywell 803, 804 for receiving a valve, preferably a check valve attached to a cover (see FIG. 8B). Substrate 800 further includes one or more well banks 806a, b, c, and d, each having one or more wells 805 located therein. Each of the wells 805 of substrate 800 have channels leading from well 805 to elastomeric block location 807 within substrate 800 for attaching an elastomeric block, preferably an elastomeric block formed from two or more layers of elastomeric material having microfabricated recesses or channels formed therein.

Figure 8C:
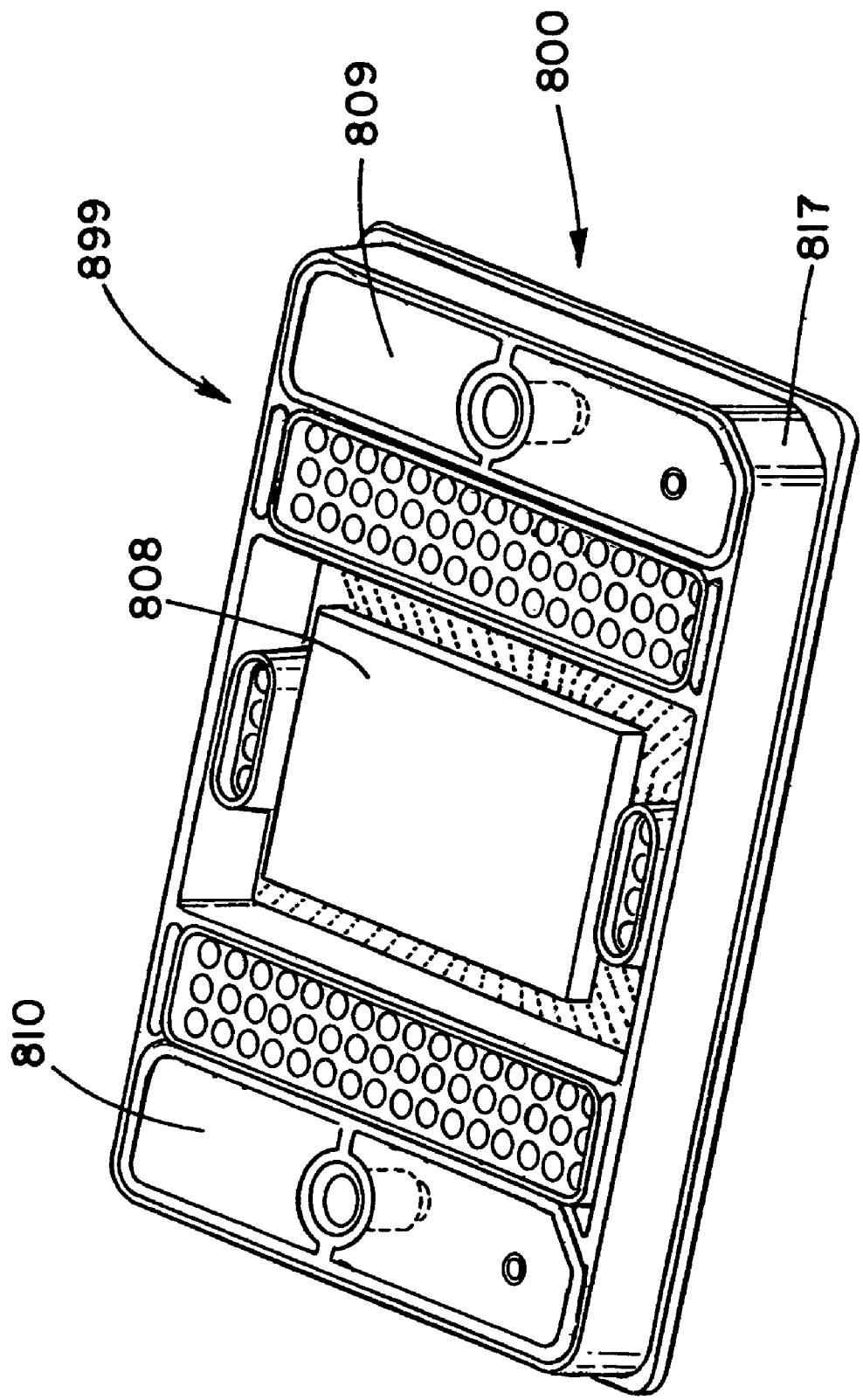
FIG. 8C is an overall view of the microfluidic device shown in FIG. 8B.

FIG. 8B depicts an exploded view of a complete microfluidic device 899 comprising the components shown in FIG. 8A, and further comprising an elastomeric block 808 which is attached, or more preferably bonded, and yet more preferably directly bonded, preferably without use of adhesives to the elastomeric block location 807 of substrate 800 to form the complete microfluidic device 899 (FIG. 8C). Within elastomeric block 808 are one or more channels in fluid communication with one or more vias 814, which in turn provide fluid communication between the channels within the elastomeric block and channels within the substrate which then lead to wells 805 within well rows 806a-d to provide for fluid communication between wells 805 of substrate 800 and the channels within elastomeric block 808. Accumulator well tops 809 and 810 are attached to accumulator wells 801 and 802 to form accumulator chambers 815 and 816. Accumulator well tops 809 and 810 include valves 812 and 811, respectively, which are preferably check valves for introducing and holding gas under pressure into accumulator chambers 815 and 816. Valves 811 and 812 are situated inside of drywells 802 and 804 to keep liquid, when present in accumulator chambers 815 and 816, from contacting valves 811 and 812. Valves 811 and 812 preferably may be mechanically opened by pressing a shave, pin or the like, within a preferred check valve to overcome the self closing force of the check valve to permit release of pressure from the accumulator chamber to reduce the pressure of the fluid contained within the accumulator chamber.

Figure 8D:
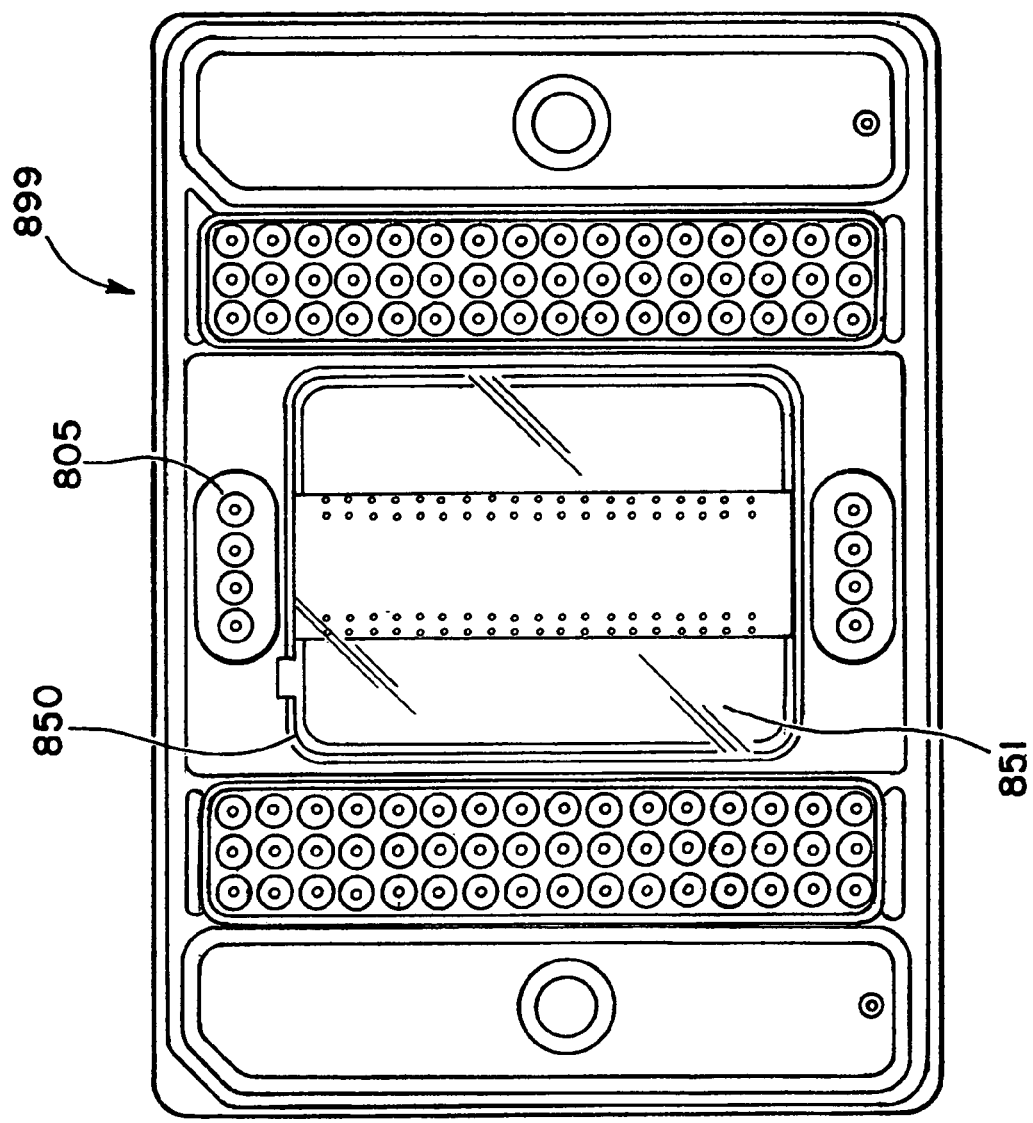
FIG. 8D is a plan view of the microfluidic device shown in FIG. 8B.

FIG. 8D depicts a plan view of microfluidic device 899 and wells 805, wherein a port is located adjacent the base of the well, preferably the bottom, or alternatively the side of well 805 for passage of fluid from the well into a channel formed in substrate 800, preferably on the side of substrate 800 opposite of well 805. In a particularly preferred embodiment, substrate 800 is molded with recesses therein, the recesses being made into channels by a sealing layer, preferably an adhesive film or a sealing layer.

Substrate 800 and its associated components may be fabricated from polymers, such as polypropylene, polyethylene, polycarbonate, high-density polyethylene, polytetrafluoroethylene PTFE or Teflon (R), glass, quartz, or a metal (for example, aluminum), transparent materials, polysilicon, or the like. Accumulator well tops 809 and 810 further may comprise access screws 812 which can be removed to introduce or remove gas or liquid from accumulator chambers 815 and 816. Preferably, valves 812 and 811 can be actuated to release fluid pressure otherwise held inside of accumulator chambers 815 and 816. Notch 817 is used to assist correct placement of the microfluidic device into other instrumentation, for example, instrumentation used to operate or analyze the microfluidic device or reactions carried out therein. FIG. 8D further depicts a hydration chamber 850 surrounding elastomeric block region 807, which can be covered with a hydration cover 851 to form a humidification chamber to facilitate the control of humidity around the elastomeric block. Humidity can be increased by adding volatile liquid, for example water, to humidity chamber 851, preferably by wetting a blotting material or sponge. Polyvinyl alcohol may preferably be used. Humidity control can be achieved by varying the ratio of polyvinyl alcohol and water, preferably used to wet a blotting material or sponge. Hydration can also be controlled by using a humidity control device such as a HUMIDIPAK™ humidification package which, for example, uses a water vapor permeable but liquid impermeable envelop to hold a salt solution having a salt concentration suitable for maintaining a desired humidity level. See U.S. Pat. No. 6,244,432 by Saari et al, which is herein incorporated by reference for all purposes including the specific purpose of humidity control devices and methods. Hydration cover 850 is preferably transparent so as to not hinder visualization of events within the elastomeric block during use. Likewise, the portion of substrate 800 beneath the elastomeric block region 807 is preferably transparent, but may also be opaque or reflective.

Figure 8E:
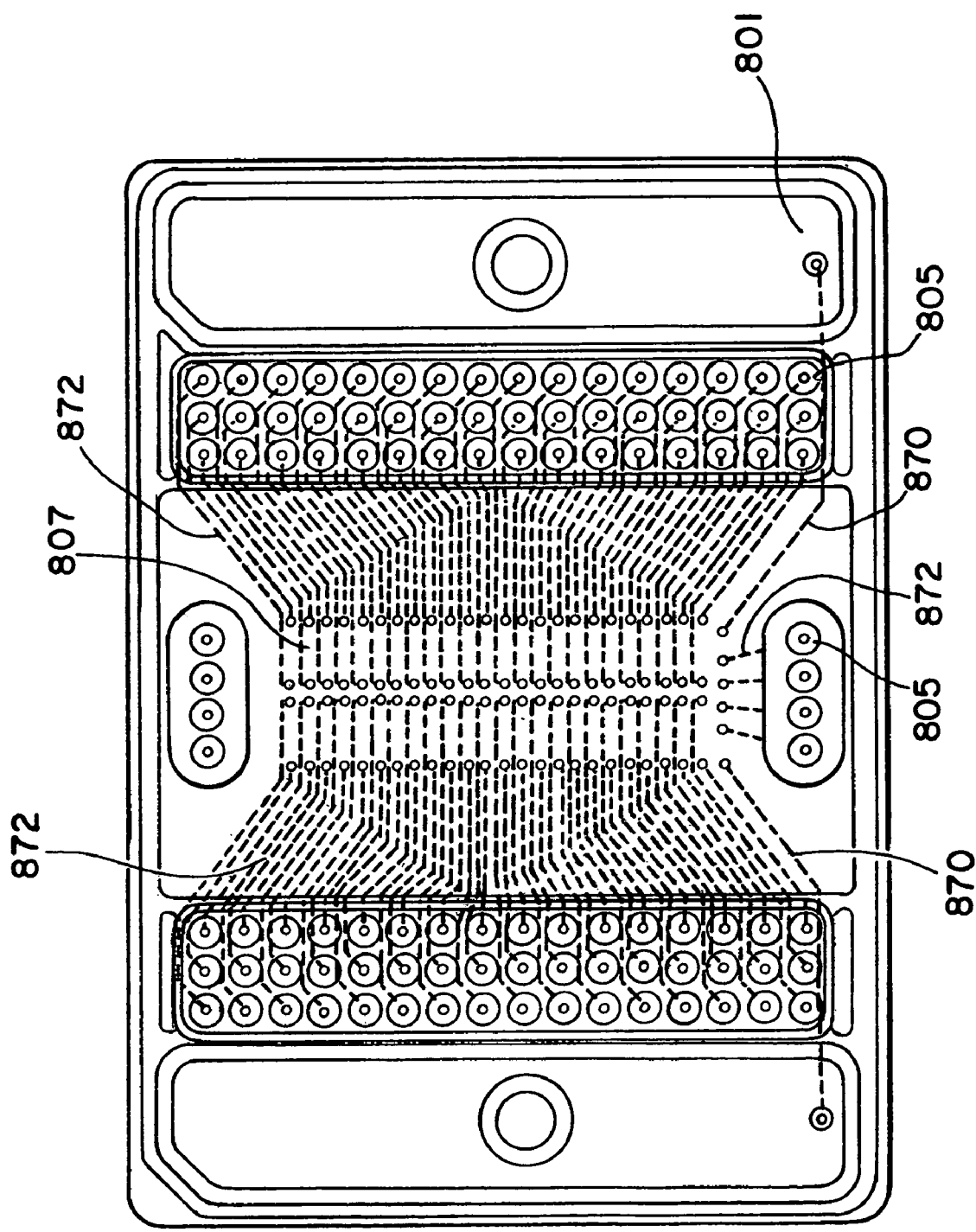
FIG. 8E depicts a plan view of the microfluidic device shown in FIG. 8B.

FIG. 8E depicts a plan view of substrate 800 with its channels formed therein providing fluid communication between wells 805 and elastomeric block 808 (not shown) which is attached to substrate 800 within elastomeric block region 807, through channels 872. Accumulator chambers 801 and 802 are in fluid communication with elastomeric block region 807 and ultimately, elastomeric block 808, through channels 870.

Figure 8F:
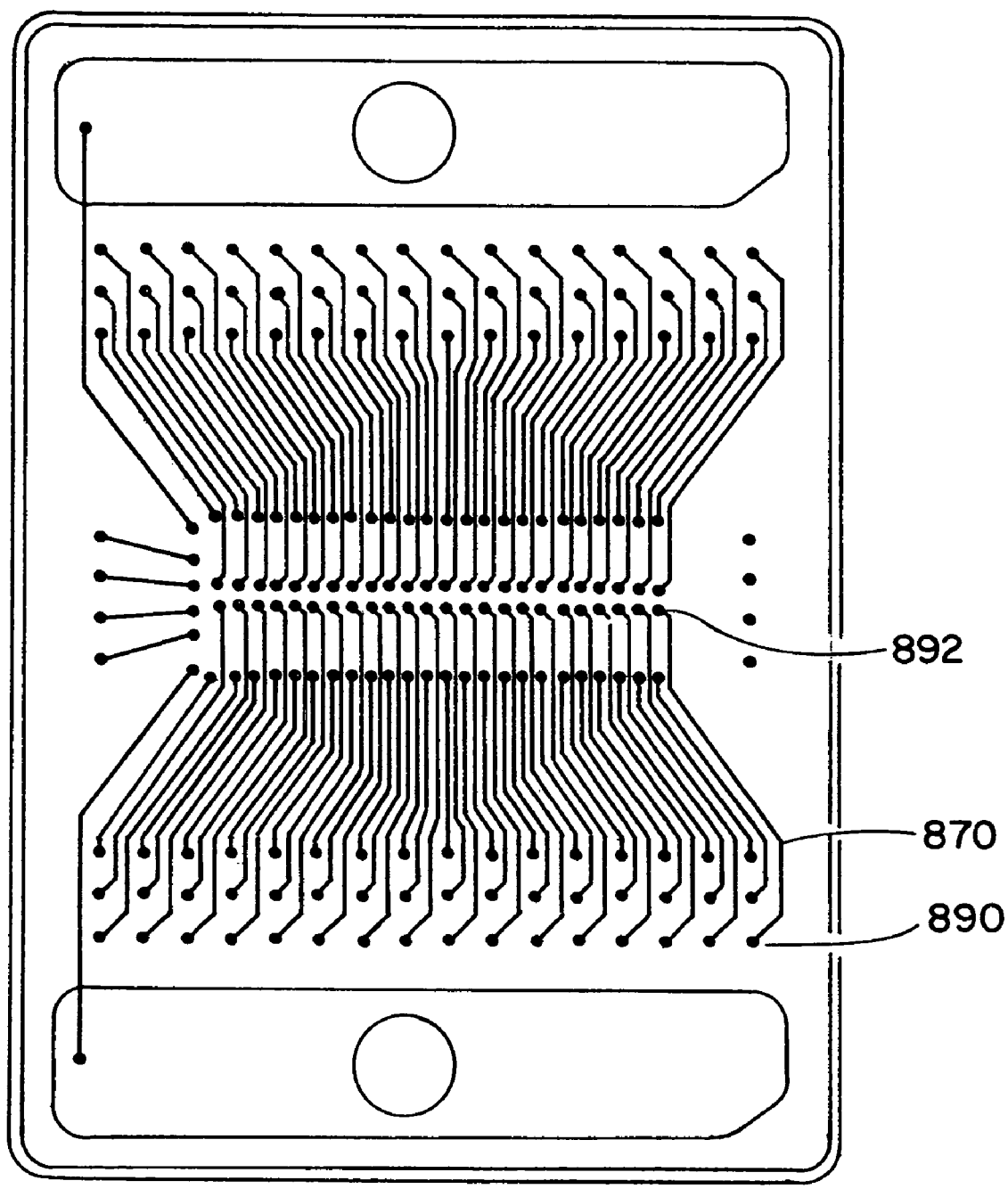
FIG. 8F depicts a bottom plan view of the microfluidic device shown in FIG. 8B.

FIG. 8F depicts a bottom plan view of substrate 800. In a particularly preferred embodiment, recesses are formed in the bottom of substrate 800 between a first port 890 which passes through substrate 800 to the opposite side where wells 805 are formed and a second port 892 which passes through substrate 800 in fluid communication with a via in elastomeric block 808 (not shown).

Figure 8G:
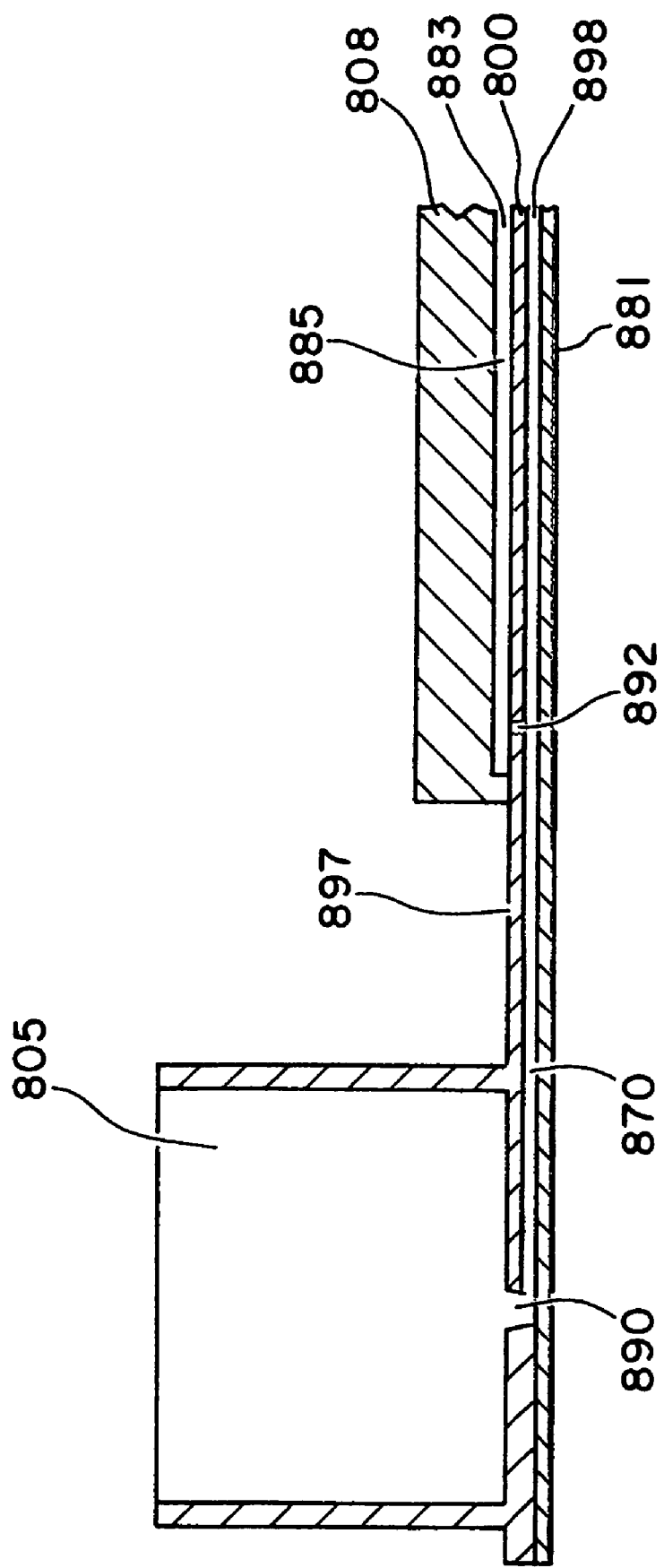
FIG. 8G depicts a cross-sectional view of the microfluidic device shown in FIG. 8B.

FIG. 8G depicts a cross-sectional view of substrate 800 with elastomeric block 808 situated in elastomeric block region 807 along with sealing layer 881 attached to the side of substrate 800 opposite of elastomeric block 808. Well 805 is in fluid communication with elastomeric block 808 through first port 890, channel 870, and second port 892 and into a recess of elastomeric layer 808, which is sealed by a top surface 897 of substrate 800 to form a channel 885. Sealing layer 881 forms channel 870 from recesses molded or machined into a bottom surface 898 substrate 800. Sealing layer 881 is preferably a transparent material, for example, polystyrene, polycarbonate, or polypropylene. In one embodiment, sealing layer 881 is flexible such as in adhesive tape, and may be attached to substrate 800 by bonding, such as with adhesive or heat sealing, or mechanically attached such as by compression. Preferably materials for sealing layer 881 are compliant to form fluidic seals with each recess to form a fluidic channel with minimal leakage. Sealing layer 881 may further be supported by an additional support layer that is rigid (not shown). In another embodiment, sealing layer 881 is rigid.

Figure 9A:
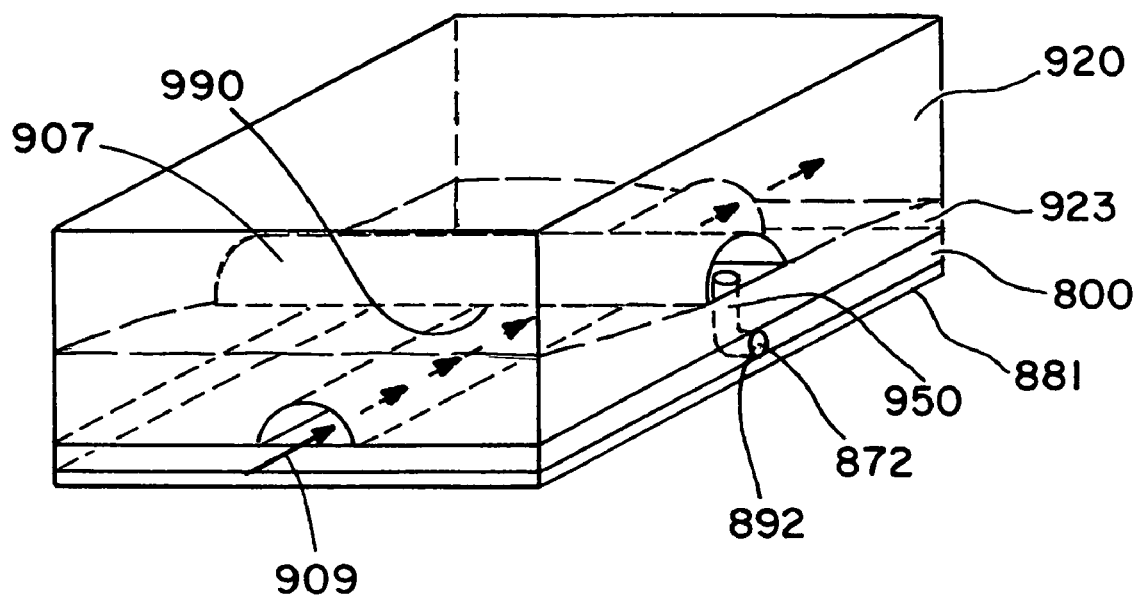
FIGS. 9A and 9B are close-up views of a fluidic interface according to an embodiment of the present invention.

FIG. 9A depicts a close-up detail of the fluidic interface between elastomeric block 808 and elastomeric block region 807 of substrate 800. As described in Unger and Hansen, elastomeric blocks may be formed from multiple layers of elastomeric material bonded together to form an elastomeric block. Preferably at least two of the layers of the elastomeric block have recesses. For example, a first elastomeric layer having recesses formed therein is bonded to a second elastomeric layer having recesses formed therein to form an elastomeric block having recesses formed therein. The recesses of the first elastomeric layer are wholly or partly closed off to form channels in the first elastomeric layer. The recesses formed in the second elastomeric layer are likewise wholly or partly closed off to form channels in the second elastomeric layer when the elastomeric layer is bonded to a substrate, thereby forming a microfluidic device having multiple layers with channels formed therein.

Figure 9B:
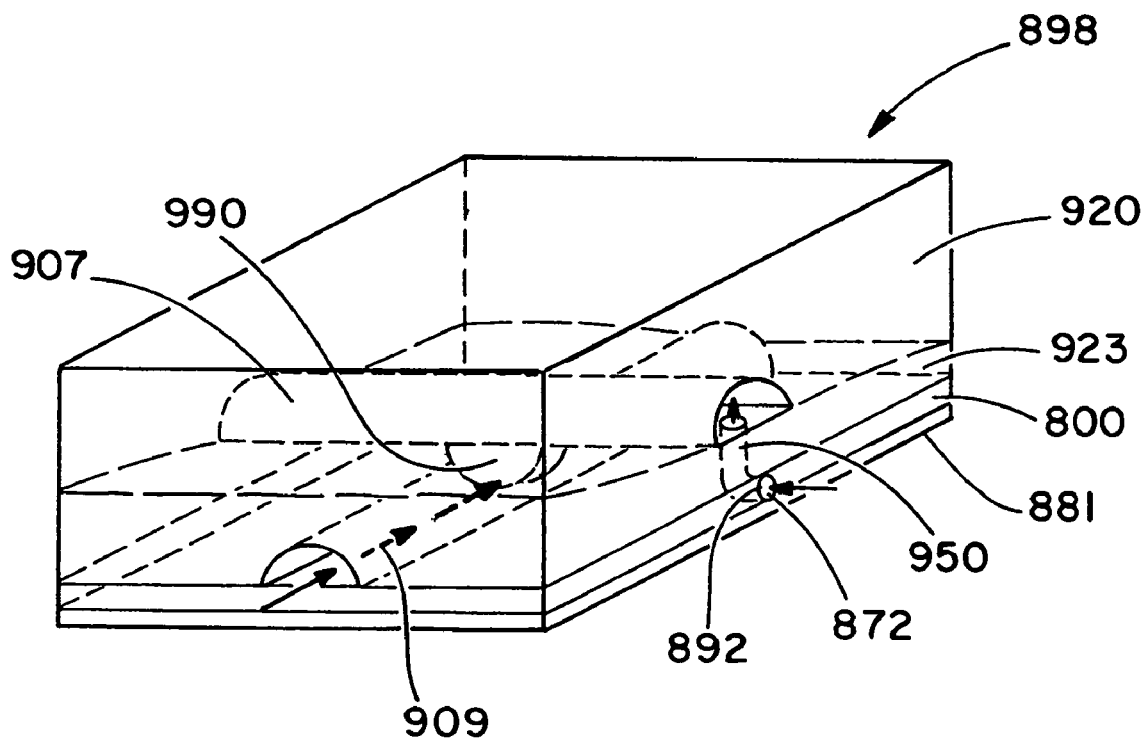

Turning to FIGS. 9A and 9B, a first elastomeric layer 920 having a bottom surface with first recesses 901 formed therein and second elastomeric layer 923 having a top surface and a bottom surface with second recesses 905 formed therein are bonded together to form elastomeric block having channel 907 (formed from first recess 901 and the top surface of second elastomeric layer 923. Substrate 800 is attached to the bottom surface of the second elastomeric layer 923 to form channel 909 from top surface 897 of substrate 800 and the bottom surface of second elastomeric layer 923. Port 892 may connect channel 872 of substrate 800 with channel 909 of the second elastomeric layer, which is partly formed by the top surface of substrate 800. Alternatively as shown in FIGS. 9A-9B, port 892 connects channel 872 of substrate 800 with channel 907 for first elastomeric layer 920 of elastomeric block 808 through a via 950. Via 950 is formed about normal to substrate surface 897, preferably formed in second elastomeric layer 923, prior to its bonding with elastomeric layer 920, and more preferably after the first and second elastomeric layers are bonded together. See co-pending and commonly assigned U.S. Provisional Patent Application Ser. No. 60/557,715 by Unger filed on Mar. 29, 2004, which is incorporated by reference for all purposes and the specific purpose of teaching via formation using automated laser ablation systems and methods. Exemplary methods for creating vias include microfabricating while forming second elastomeric layer 923, laser drilling, laser drilling with a $CO_2$ laser, laser drilling with an excimer laser, drilling mechanically, and coring, preferably wherein the drilling is performed by a robotic drill system, preferably one having an x,y automated stage.

FIG. 9B depicts the microfluidic device of FIG. 9A, wherein channel 907 of first elastomeric layer 920 overlaps channel 909 of second elastomeric layer 923 to form a deflectable portion within the elastomeric block, preferably an elastomeric membrane, preferably formed from a portion of second elastomeric layer 923. Fluid pressure is transmitted to channel 907 of first elastomeric layer 920 from a pressurized fluid source (not shown) through channel 872, port 892, and via 950 to cause elastomeric membrane 990 to deflect downward to control fluid flow or diffusion through channel 909 of second elastomeric layer 923.

FIG. 9C depicts a cross sectional view of another preferred use of a via in the microfluidic devices described herein. Microfluidic block 921 includes first layer 920 having first layer recess (or channel when bonded to a second layer) 907 formed therein and second layer 923 having second layer recesses (or channels when bonded to a substrate) 950 therein. Two second layer channels are in fluid communication through a first layer channel by way of two or more vias 950. Preferably, at least one via 950 is in further fluid communication with well 999 of substrate 800 through a substrate recess 892 (or channel if a sealing layer (not shown) is bonded to substrate 800). At least one second layer channel 909 is overlapped by a portion of first layer channel 907 without being in fluid communication. In the embodiment shown in FIG. 9C, a higher density of reaction and/or detection zones per unit area of microfluidic device may be achieved because a fluid channel in one layer can be routed over or under an intervening fluid channel within the same layer. Ablation debris chambers 989 are present to catch debris produced from laser ablating via 950. Debris chamber 989 may be cast into layer 920 by two-layer casting methods, wherein after a first layer of photoresist has been patterned and developed, a second layer of photoresist is overlaid over the first pattern, and a second pattern is formed upon the pattern of the first photoresist layer such that a regions of photoresist pattern may be of different heights. Multiple layers can be built up upon one another to create patterns of varying heights. Different photoresist materials may also be used so that, for example, the upper layer of photoresist is capable of reflowing when heated, while the lower layer is made of a photoresist that does not substantially reflow at the same heated temperature.

Figure 9D:
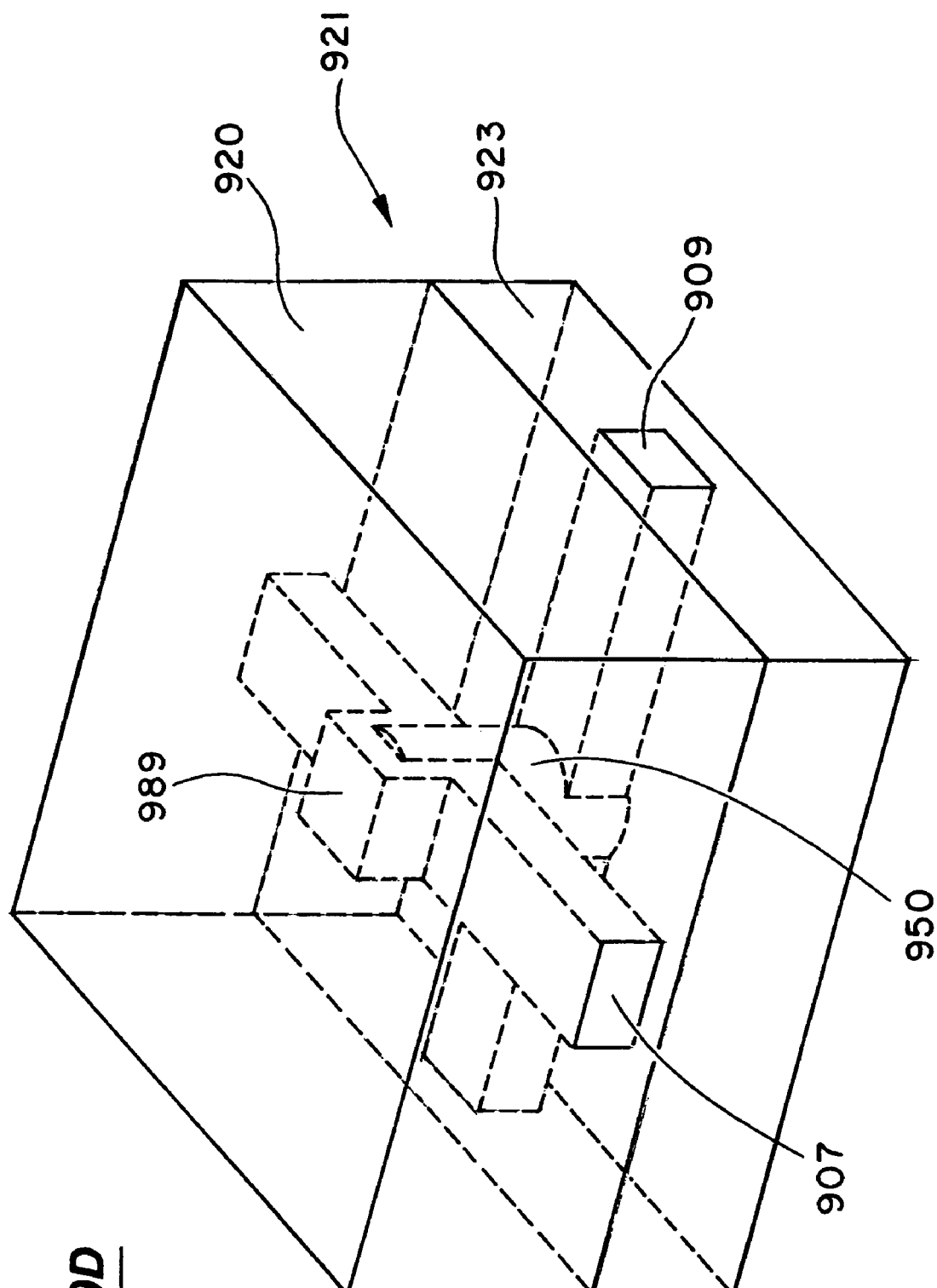
FIG. 9D is a blown up view of a via for use in some embodiments of microfluidic devices of the present invention.

FIG. 9D depicts a blown up view of a via 950 that interconnects channels from two different layers. Microfluidic block 921 is formed from first layer 920 having channel 907 therein, and second layer 923 having second channel 909 formed therein. Via 950 interconnects channels 907 and 909 together. Also shown is debris chamber 989 which was cast into layer 920 by a multi-height molding process as described above. When via 950 is formed by laser ablation, debris or material from one of the layers may reside in the upper portion of channel 907 where the via is formed. Providing a chamber for such debris or material to reside in after ablation helps to prevent closure or stenosis of channel 907 or 909.

The flow channels of the present invention may optionally be designed with different cross sectional sizes and shapes, offering different advantages, depending upon their desired application. For example, the cross sectional shape of the lower flow channel may have a curved upper surface, either along its entire length or in the region disposed under an upper cross channel). Such a curved upper surface facilitates valve sealing, as follows. Membrane thickness profiles and flow channel cross-sections contemplated by the present invention include rectangular, trapezoidal, circular, ellipsoidal, parabolic, hyperbolic, and polygonal, as well as sections of the above shapes. More complex cross-sectional shapes, such as an embodiment with protrusions or an embodiment having concavities in the flow channel, are also contemplated by the present invention.

In addition, while the invention is described primarily in conjunction with an embodiment wherein the walls and ceiling of the flow channel are formed from elastomer, and the floor of the channel is formed from an underlying substrate, the present invention is not limited to this particular orientation. Walls and floors of channels could also be formed in the underlying substrate, with only the ceiling of the flow channel constructed from elastomer. This elastomer flow channel ceiling would project downward into the channel in response to an applied actuation force, thereby controlling the flow of material through the flow channel. In general, monolithic elastomer structures are preferred for microfluidic applications. However, it may be useful to employ channels formed in the substrate where such an arrangement provides advantages. For instance, a substrate including optical waveguides could be constructed so that the optical waveguides direct light specifically to the side of a microfluidic channel.

Figure 10:
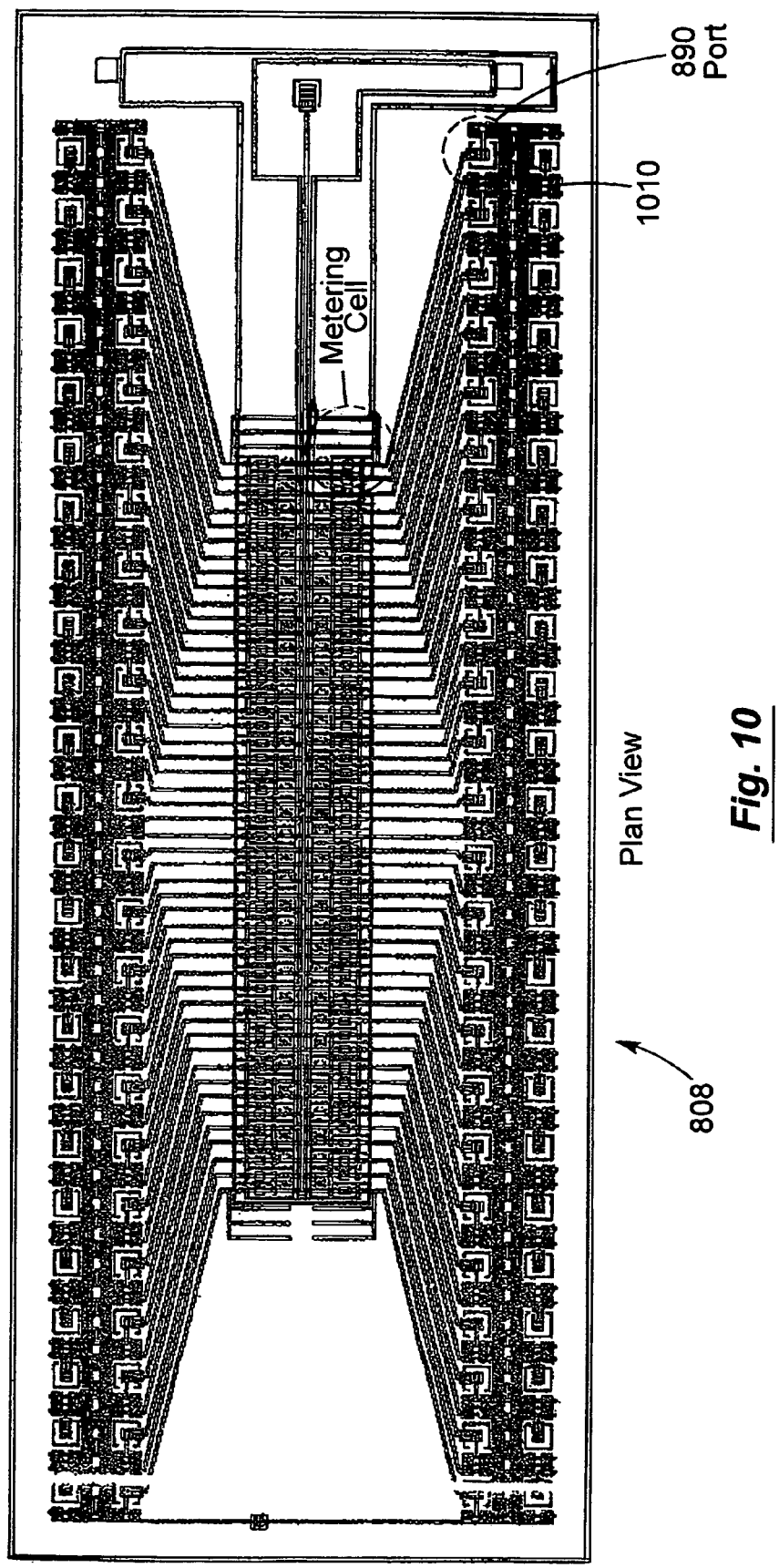
FIG. 10 is a plan view of one embodiment of a chip for use with the present invention.

FIG. 10 depicts a plan view of a preferred embodiment wherein ninety-six (96) separate metering cells are formed within an elastomeric block 808. In a preferred embodiment, hydration lines 1010 are provided adjacent each elastomeric block inlet which connects ports within substrate 800 (not shown) to channels within elastomeric block 808, to provide a source of solutions at a selected osmolarity to provide a source of hydration and/or osmo-regulation to portions of elastomeric block 808.

Figure 11A:
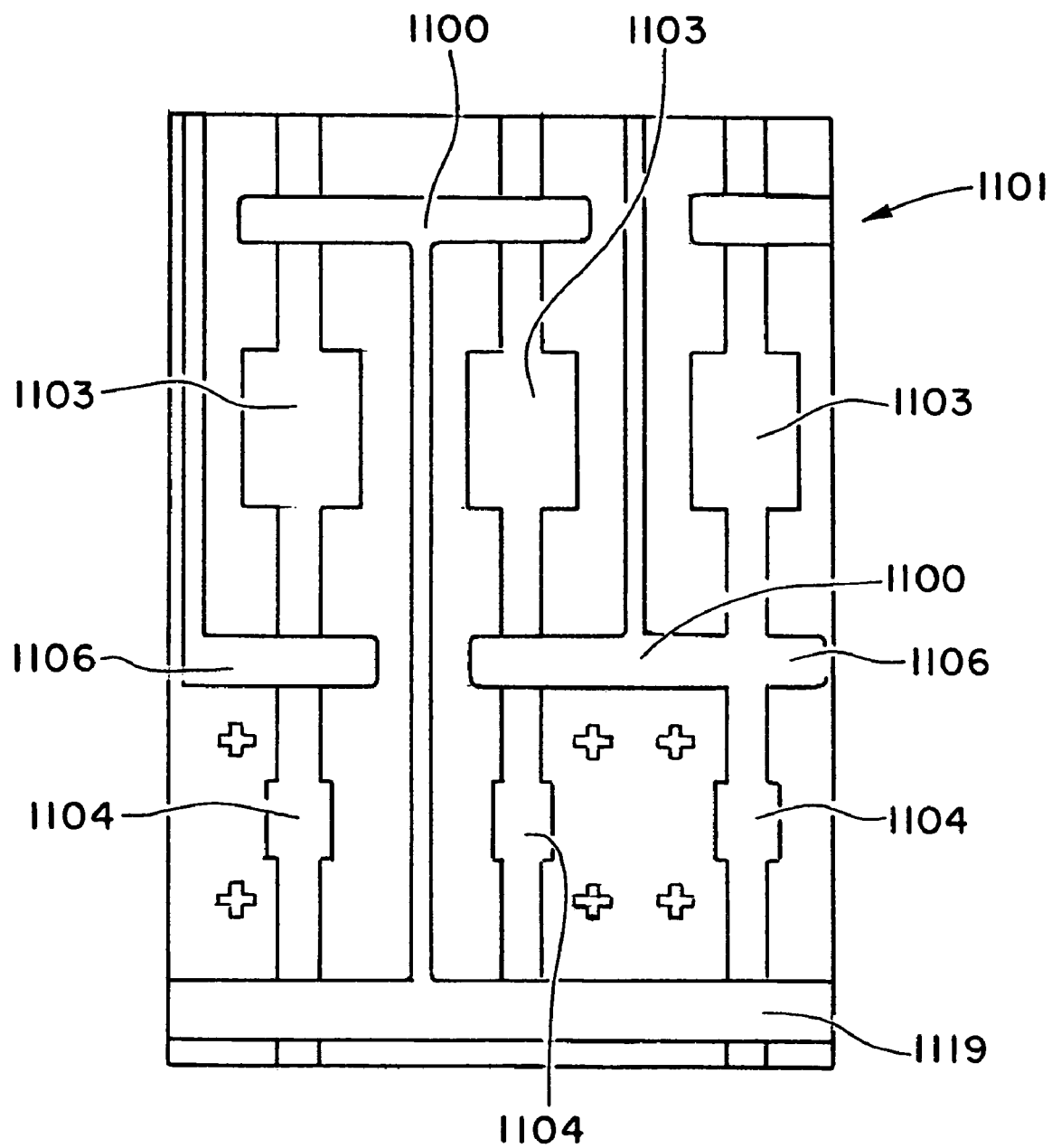
FIG. 11A-D are close up plan view of exemplary metering cells in various valve states according to embodiments of the present invention.

FIG. 11A depicts a close-up plan view of an exemplary metering cell used for protein crystallization wherein fluid flow in adjacent channels and chambers is controlled by deflectable membrane valves, preferably opposing "T" or tee shaped interdigitated valves 1100. In preferred embodiments, when a series of channels and reagent chambers are located in close proximity such that osmolarity differences between adjacent reagent chambers or channels may cause migration of fluid, typically in vapor form, through the elastomeric layers of the elastomeric block, using discontinuous valve lines serve to "osmotically" isolate reagent chambers when compared to linear valve lines 119 which have a shorter fluid distance between each chamber.

Figure 11B:
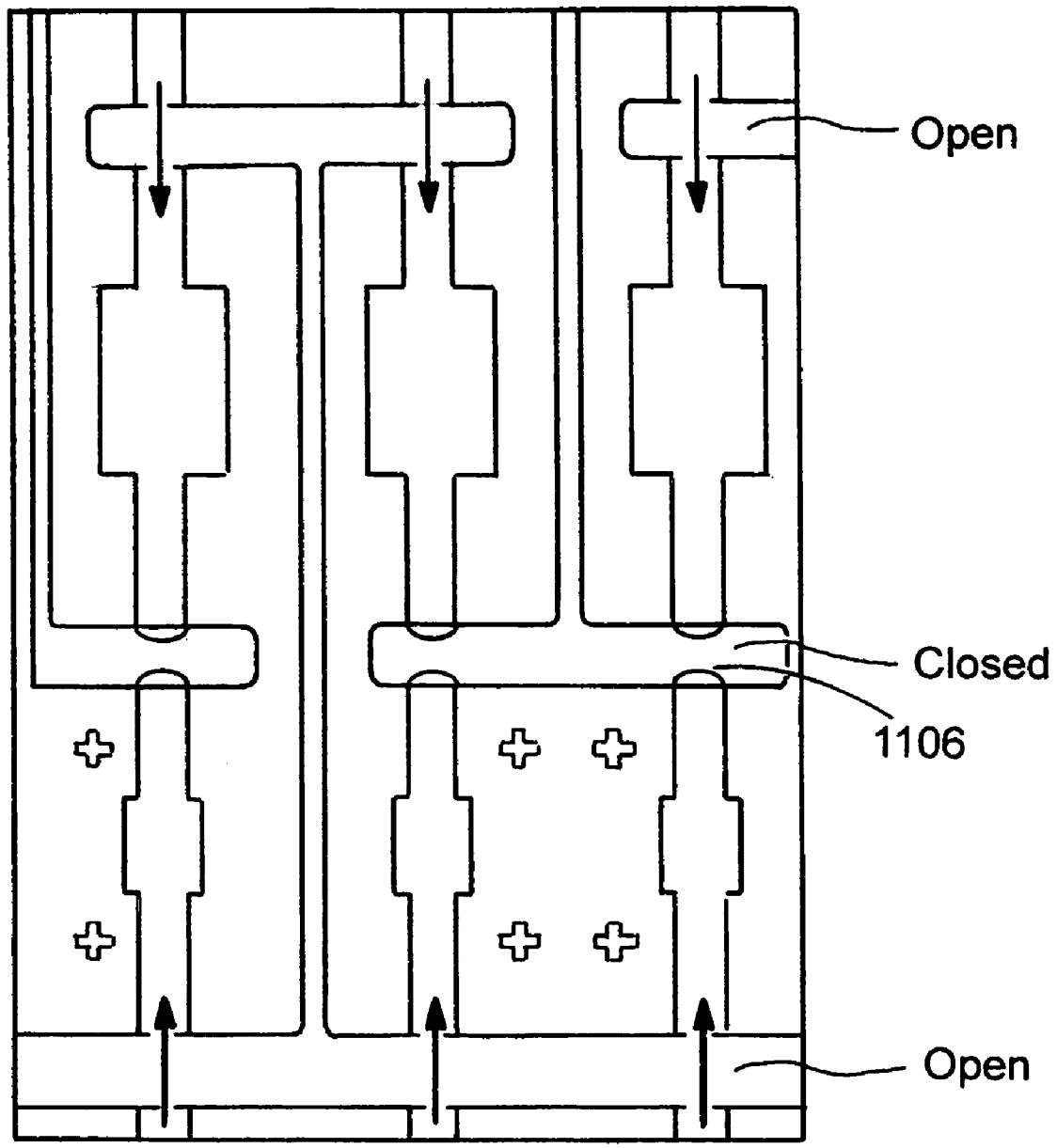
Figure 11C:
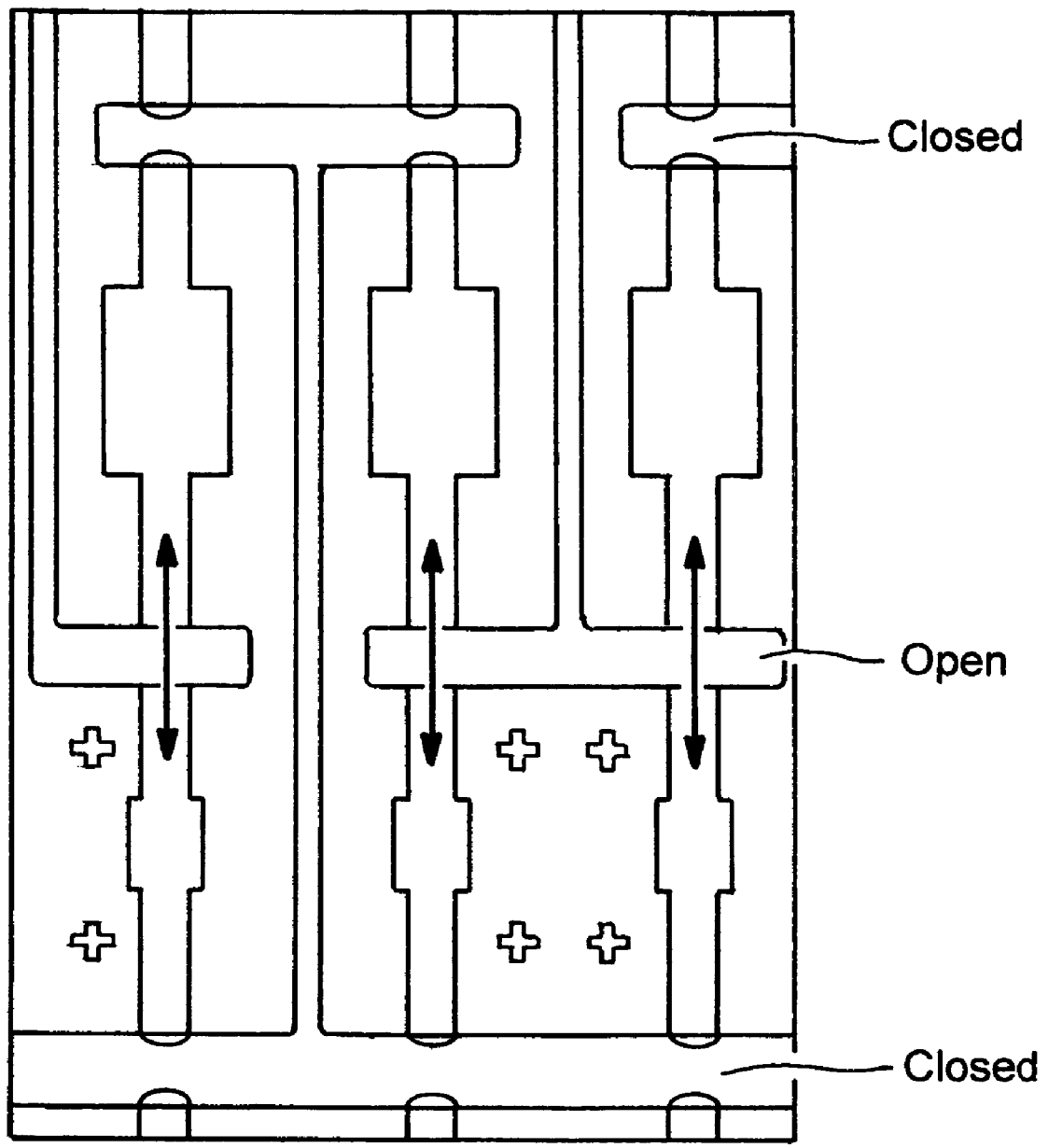
Figure 11D:
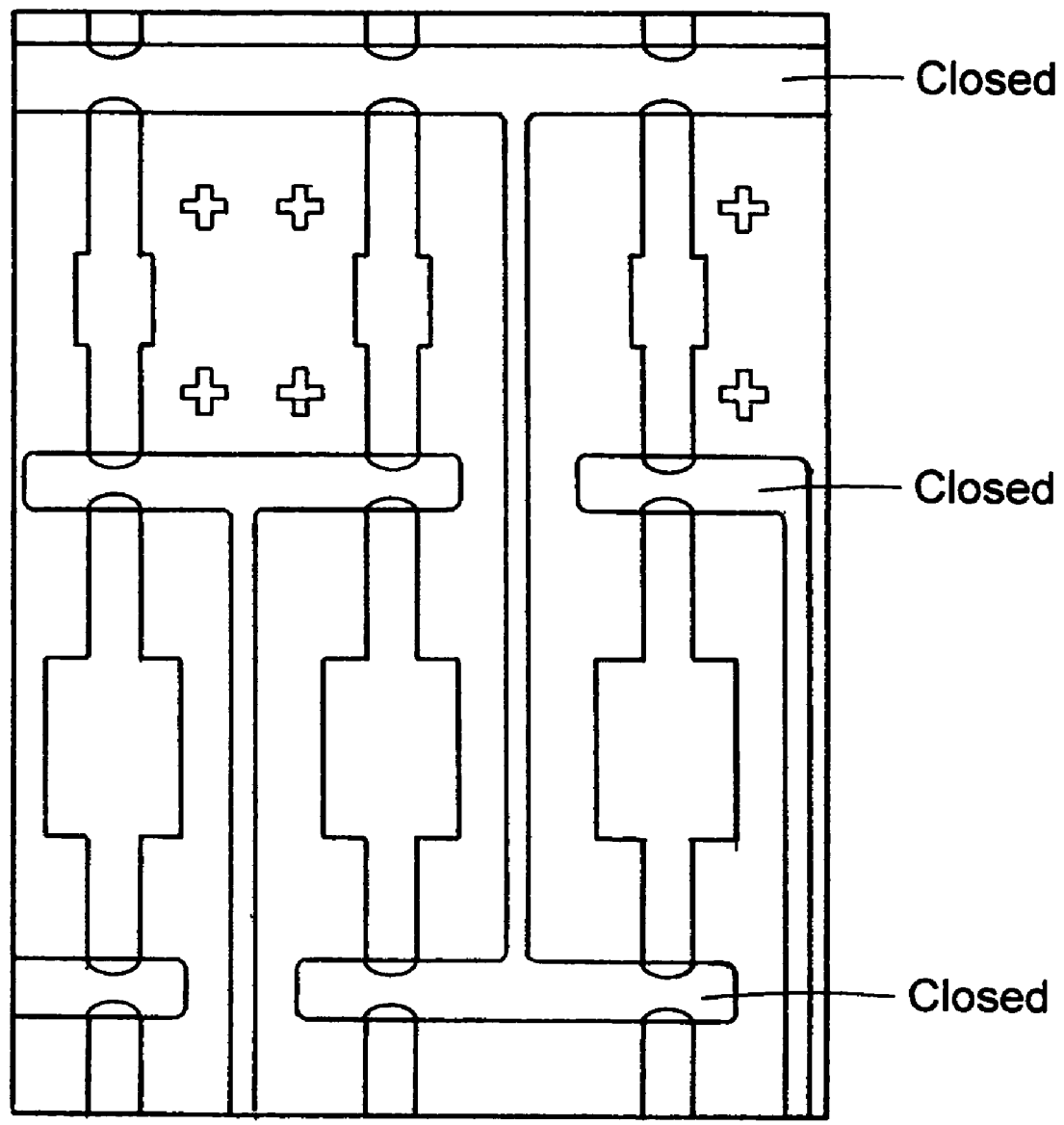

FIG. 11B depicts a valve state for a metering cell. Within metering cell 1101 show, reagent chambers 1103 and protein chamber 1104 are isolated from each other by the actuation of interface valves 1106 while reagent and protein solution are introduced into each respective chamber. Once filled, containment valves 1109 are closed, as shown in FIG. 11C and free interface diffusion is performed by opening interface valves 1106. As shown in FIG. 11D, diffusion may be interrupted by closing interface valve 1106 to permit, for example, dehydration to occur if the ambient humidity around or within elastomeric block 808 is reduced.

Figure 11E:
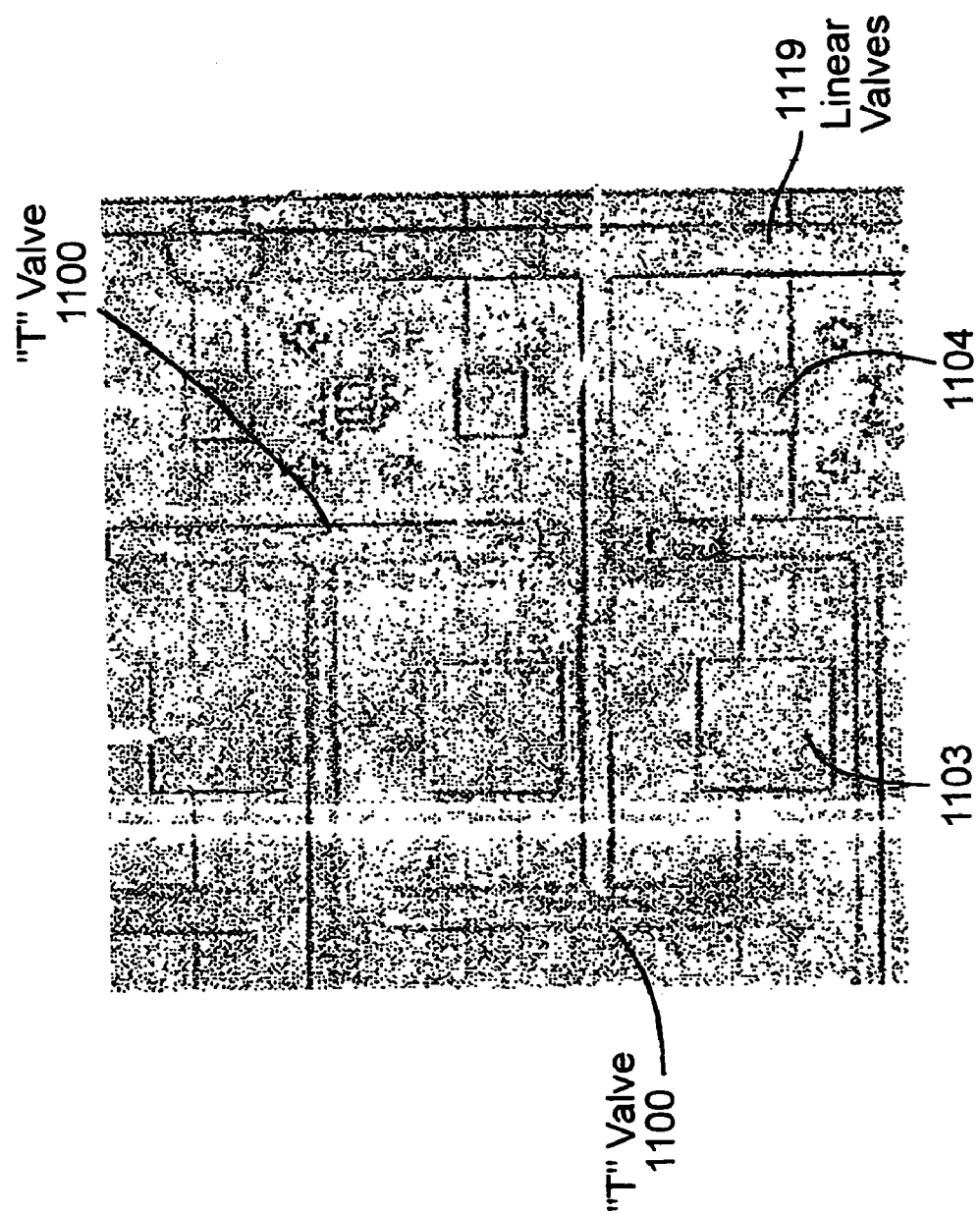
FIG. 11E is a photograph of an exemplary metering cell format.

FIG. 11E is a photograph of an exemplary metering cell format.

Figure 11F:
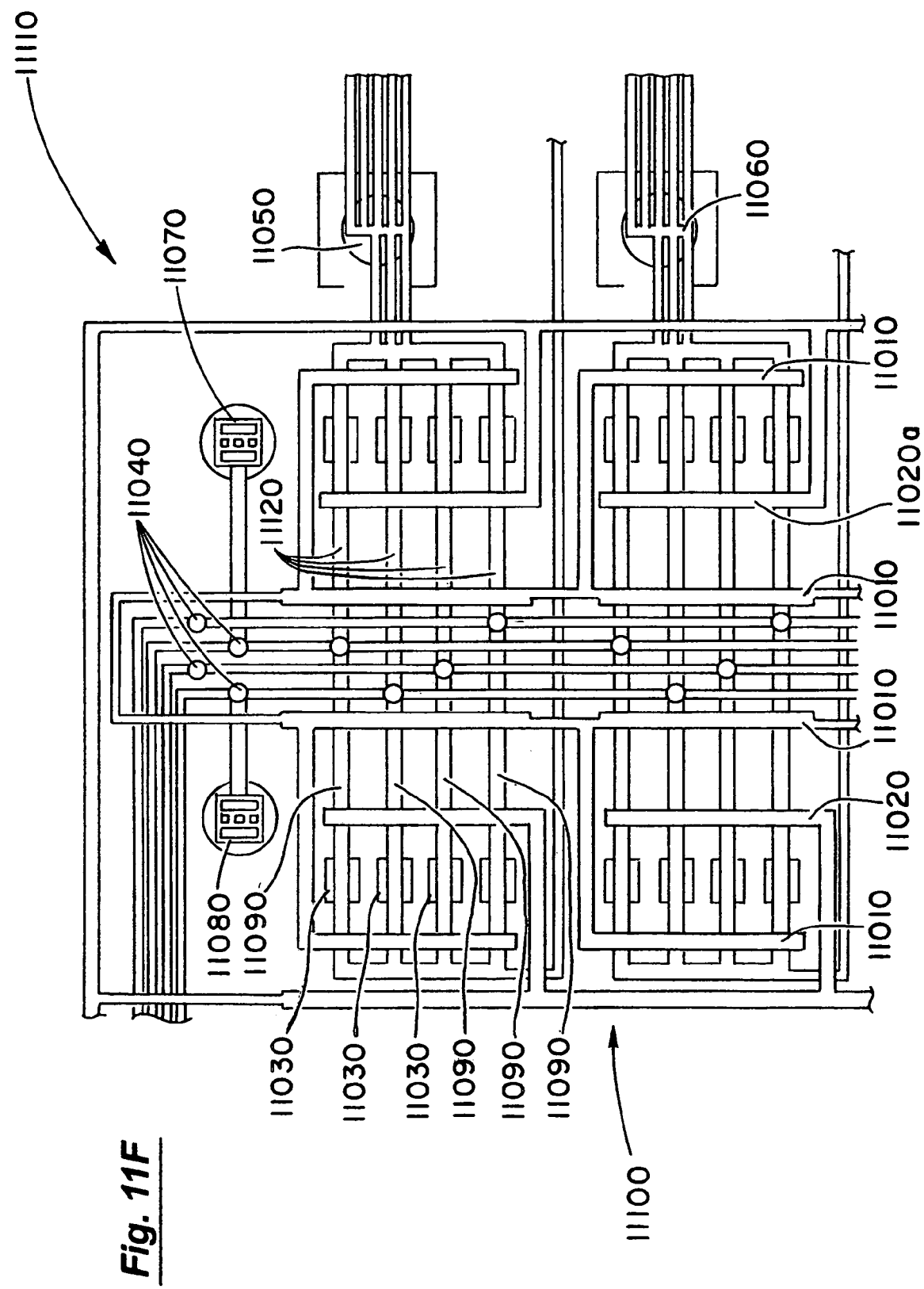
FIG. 11F depicts a high density formal for reacting a plurality of samples according to an embodiment of the present invention.

FIG. 11F depicts a high density format for reacting a plurality of samples with a plurality of reagents, for example, preferably four (4) samples with ninety-six (96) reagents; eight (8) samples with ninety-two (92) reagents, and so forth, including, but not limited to forty-eight (48) samples with forty-eight (48) reagents. Each reaction pair may be separately mixed or combined, such as by diffusion, the format utilizing fluid channel overpasses or underpasses to route other intervening fluid channels. FIG. 11F is a close up view of an example of a use of vias to increase the reaction/detection region density of a microfluidic chip. A close up view 11110 is provided of four sets of metering cells for carrying out reactions such as protein crystallization experiments. Metering cell 11100 comprises four sets of chambers in each set having a first chamber and a second chamber in fluid communication and separated by an interface valve 11020. With interface valve 11020 closed, reagents are introduced though ports such as port 11050 which is in fluid communication with a metering cell 11100 for filling reagent chambers 11030, and sample inlet ports 11080 and 11070, and two of which are not shown, such as protein samples, which are transported to sample chambers 11090 through channels which are interconnected through vias 11040, which allow for the samples to pass over the sample branch channels 11120. Widened channel paths, such as 11020a indicate where a deflectable membrane valve is present that is formed by the overlapping of a first layer channel and a second layer channel. Comparatively narrower channel segments represent, when overlapping other channels, regions where a deflectable membrane is not formed and therefore does not act as a valve. The architectures described herein this application may, as one of skill in the art would realize, be reversed in order. For example, a fluid layer may be formed inside of a thicker layer, and a thinner layer may be used as a control layer, and that each layer may possess both control and fluid channels therein and may be in fluid communication with one or more different layers through vias. Preferably, the devices described herein may be made of one or more elastomeric layers, preferably wherein two or more layers are bonded together. Layers may be bonded together, preferably by using complimentary chemistries in two or more layers which, when contacted, bond together, or more preferably, wherein one or more layers is treated with plasma, preferably Ar plasma, and more preferably, clean dry air plasmas etching prior to bonding, and preferably by bonding with an adhesive, preferably an adhesive comprising components similar or complimentary to the chemistry of one or more of the layers being bonded together. Adhesives may be applied by spin coating a layer surface, or by spin coating a layer of adhesive onto a surface and stamping a layer on such spun adhesive to apply adhesive to such layer prior to bonding the layer to another layer.

Figure 11G:
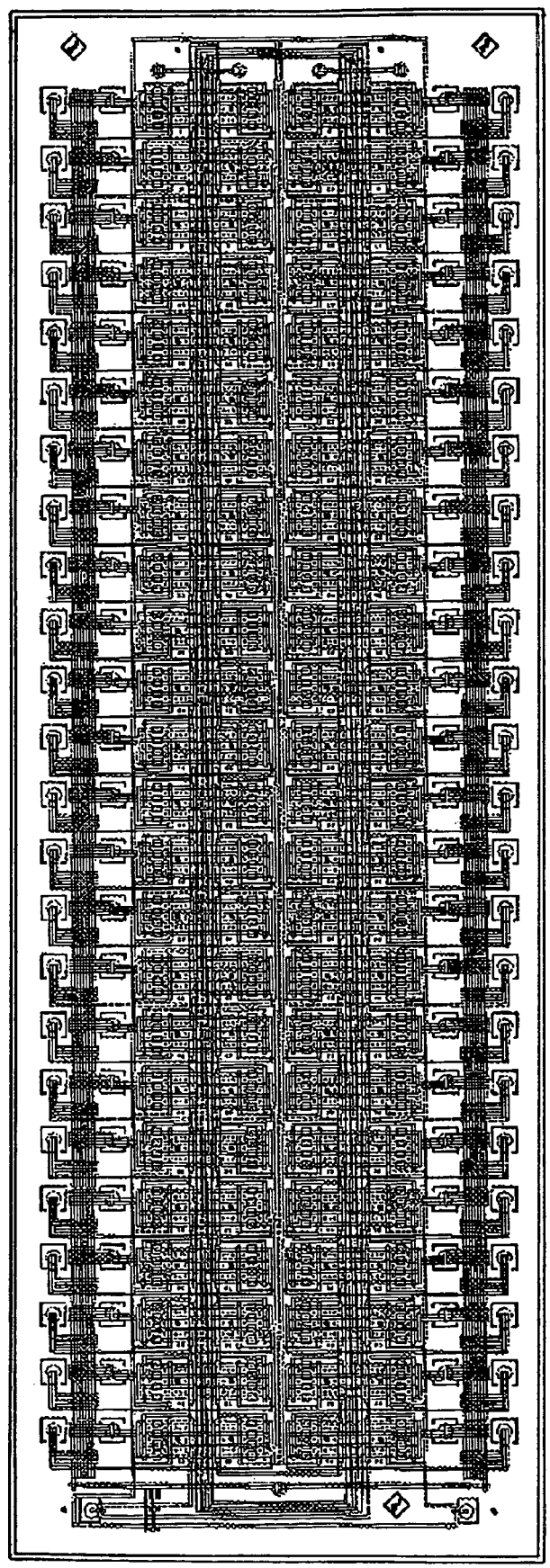
FIG. 11G is a plan view of one embodiment of a chip for use with the present invention.

FIG. 11G depicts a plan view of a preferred embodiment wherein four (4) sets of ninety-six (96) separate metering cells are forming in an elastomeric block.

The extremely small volumes capable of being delivered by pumps and valves in accordance with the present invention represent a substantial advantage. Specifically, the smallest known volumes of fluid capable of being manually metered is around 0.1 µl. The smallest known volumes capable of being metered by automated systems is about ten-times larger (1 µl). Utilizing pumps and valves in accordance with the present invention, volumes of liquid of 10 nl or smaller can routinely be metered and dispensed. The accurate metering of extremely small volumes of fluid enabled by the present invention would be extremely valuable in a large number of biological applications, including diagnostic tests and assays.

Equation 1 represents a highly simplified mathematical model of deflection of a rectangular, linear, elastic, isotropic plate of uniform thickness by an applied pressure:

$w=(BPb^4)/(Eh^3)$, where:
w=deflection of plate;
B=shape coefficient (dependent upon length vs. width and support of edges of plate);
P=applied pressure;
b=plate width
E=Young's modulus; and
h=plate thickness.

Thus even in this extremely simplified expression, deflection of an elastomeric membrane in response to a pressure will be a function of: the length, width, and thickness of the membrane, the flexibility of the membrane (Young's modulus), and the applied actuation force. Because each of these parameters will vary widely depending upon the actual dimensions and physical composition of a particular elastomeric device in accordance with the present invention, a wide range of membrane thicknesses and elasticity's, channel widths, and actuation forces are contemplated by the present invention.

It should be understood that the formula just presented is only an approximation, since in general the membrane does not have uniform thickness, the membrane thickness is not necessarily small compared to the length and width, and the deflection is not necessarily small compared to length, width, or thickness of the membrane. Nevertheless, the equation serves as a useful guide for adjusting variable parameters to achieve a desired response of deflection versus applied force.

Figure 12A:
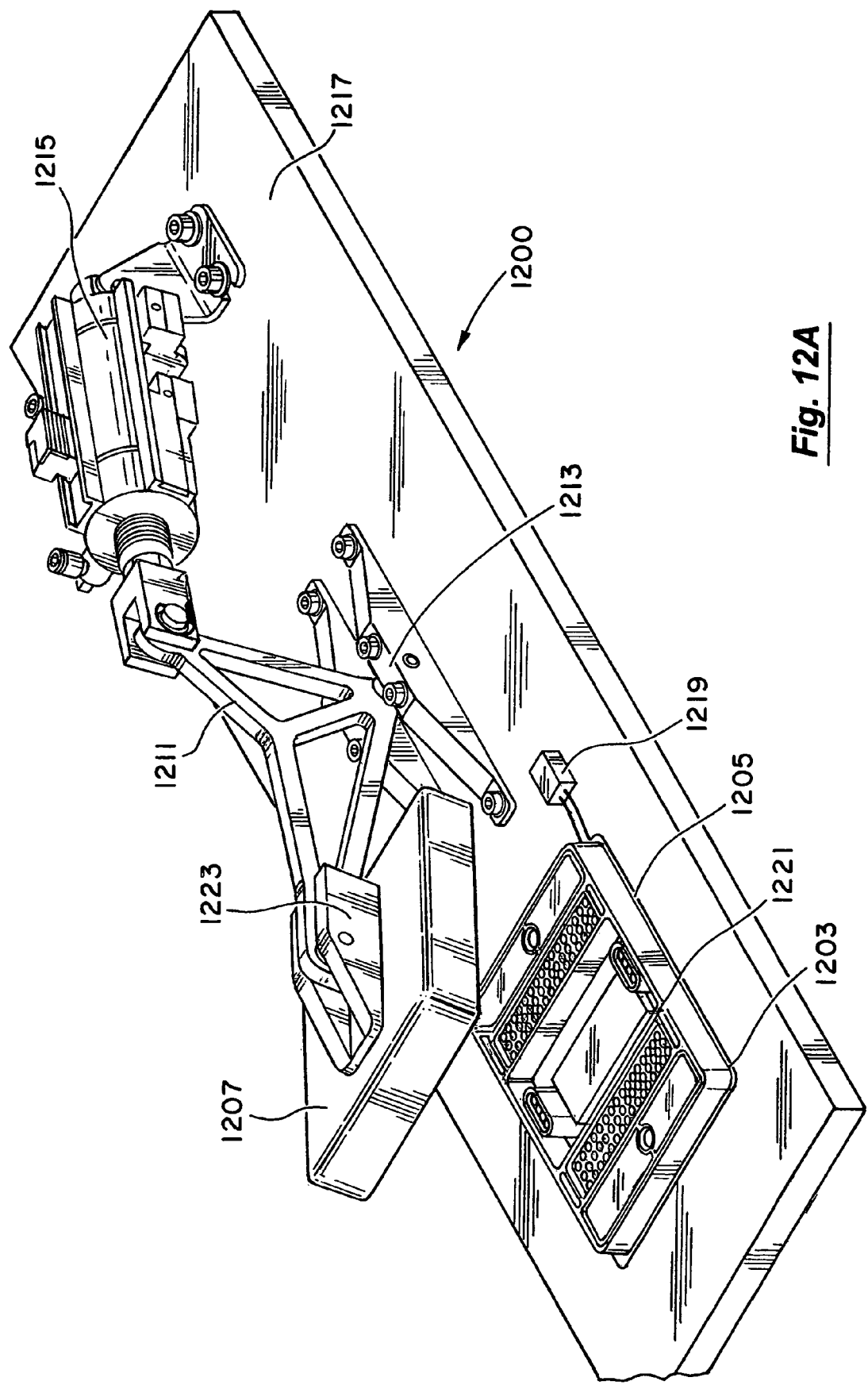
FIG. 12A is a perspective view of a station for actuating a microfluidic device according to an embodiment of the present invention.

The microfluidic devices of the present invention may be used as stand-alone devices, or preferably, may be used as part of a system as provided for by the present invention. FIG. 12A depicts a perspective view of a robotic station for actuating a microfluidic device. An automated pneumatic control and accumulator charging station 1200 includes a receiving bay 1203 for holding a microfluidic device 1205 of the present invention such as the type depicted in FIGS. 8A-G. A platen 1207 is adapted to contact an upper face 1209 of microfluidic device 1205. Platen 1207 has therein ports that align with microfluidic device 1205 to provide fluid pressure, preferably gas pressure, to wells and accumulators within microfluidic device 1205. In one embodiment, platen 1207 is urged against upper face 1221 of microfluidic device 1205 by movement of an arm 1211, which hinges upon a pivot 1213 and is motivated by a piston 1215 which is attached at one end to arm 1211 and at the other end to a platform 1217. Sensors along piston 1215 detect piston movement and relay information about piston position to a controller, preferably a controller under control of a computer (not shown) following a software script. A plate detector 1219 detects the presence of microfluidic device 1205 inside of receiving bay 1203, and preferably can detect proper orientation of microfluidic device 1205. This may occur, for example, by optically detecting the presence and orientation of microfluidic device 1205 by reflecting light off of the side of microfluidic device 1205. Platen 1207 may be lowered robotically, pneumatically, electrically, or the like. In some embodiments, platen 1207 is manually lowered to engage device 1205.

Figure 12B:
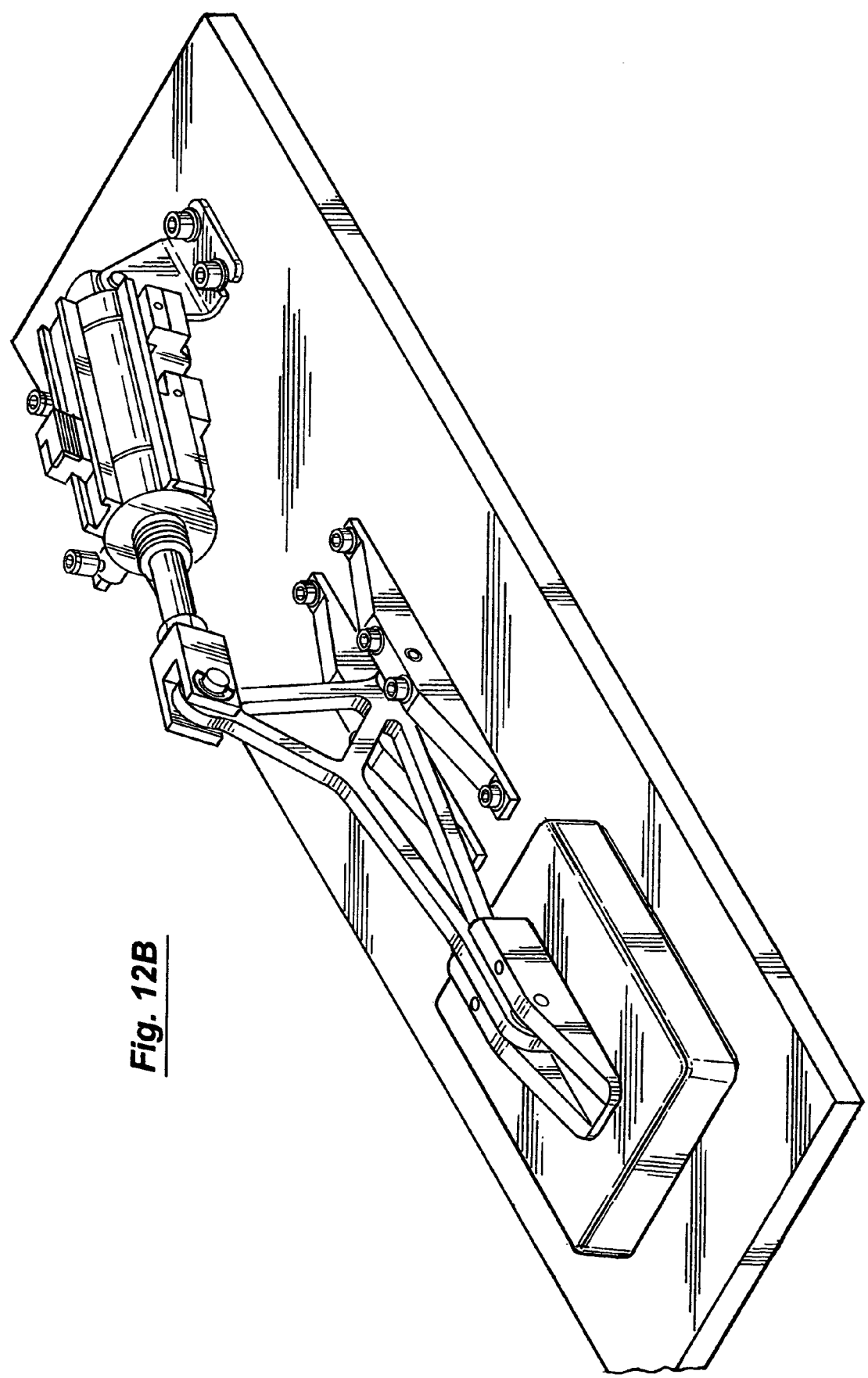
FIGS. 12B and 12D are perspective and side views, respectively, of the station of FIG. 12A with the platen in a down position.

FIG. 12B depicts charging station 1200 with platen 1207 in the down position urged against upper face 1221 of microfluidic device 1205, which is now covered by a shroud of platen 1207. In one embodiment, fluid lines leading to platen 1207 are located within arm 1211 and are connected to fluid pressure supplies, preferably automatic pneumatic pressure supplies under control of a controller. The pressure supplies provide controlled fluid pressure to ports within a platen face (not shown) of platen 1207, to supply controlled pressurized fluid to microfluidic device 1205. Fine positioning of platen 1207 is achieved, at least in-part, by employing a gimbal joint 1223 where platen 1207 attaches to arm 1211 so that platen 1207 may gimbal about an axis perpendicular to upper face 1221 of microfluidic device 1205.

Figure 12C:
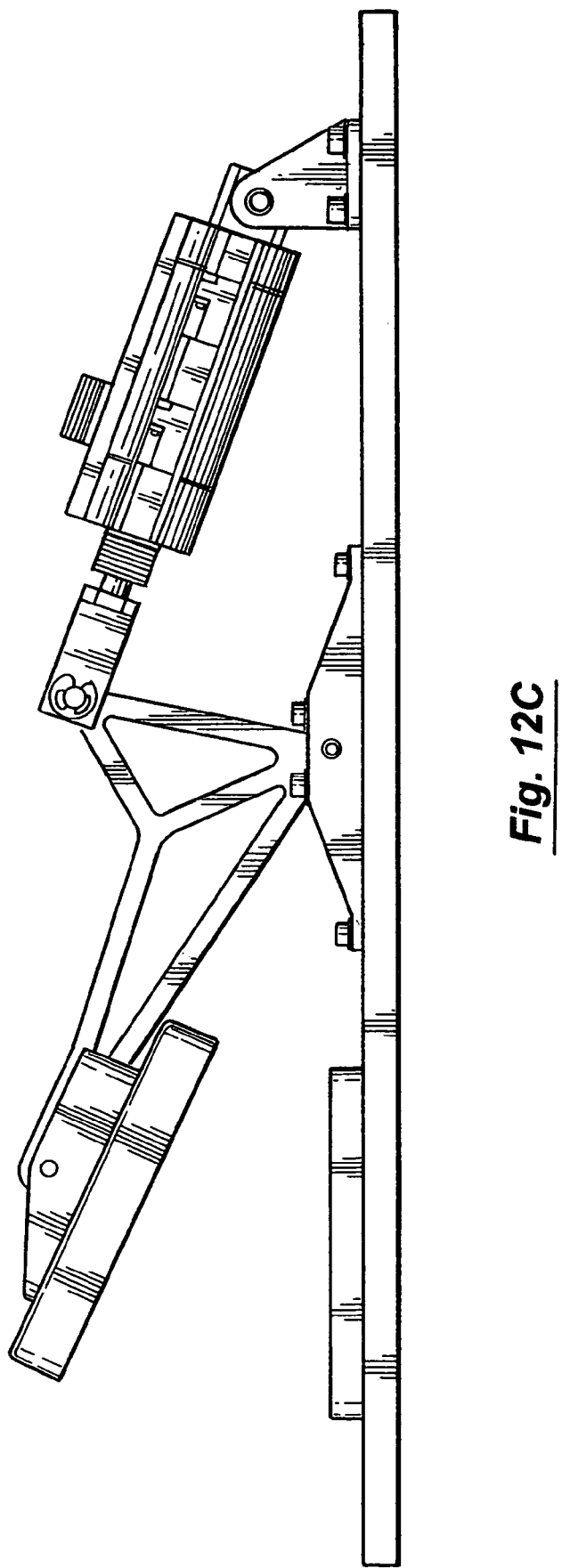
FIG. 12C is a side view of the station of FIG. 12A with the platen in an up position.
Figure 12D:
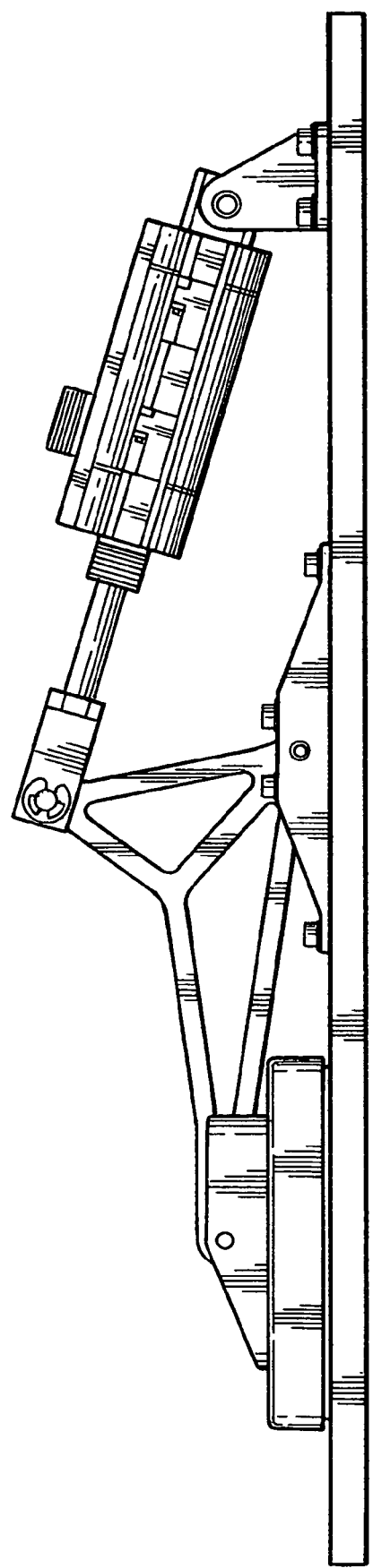
Figure 12E:
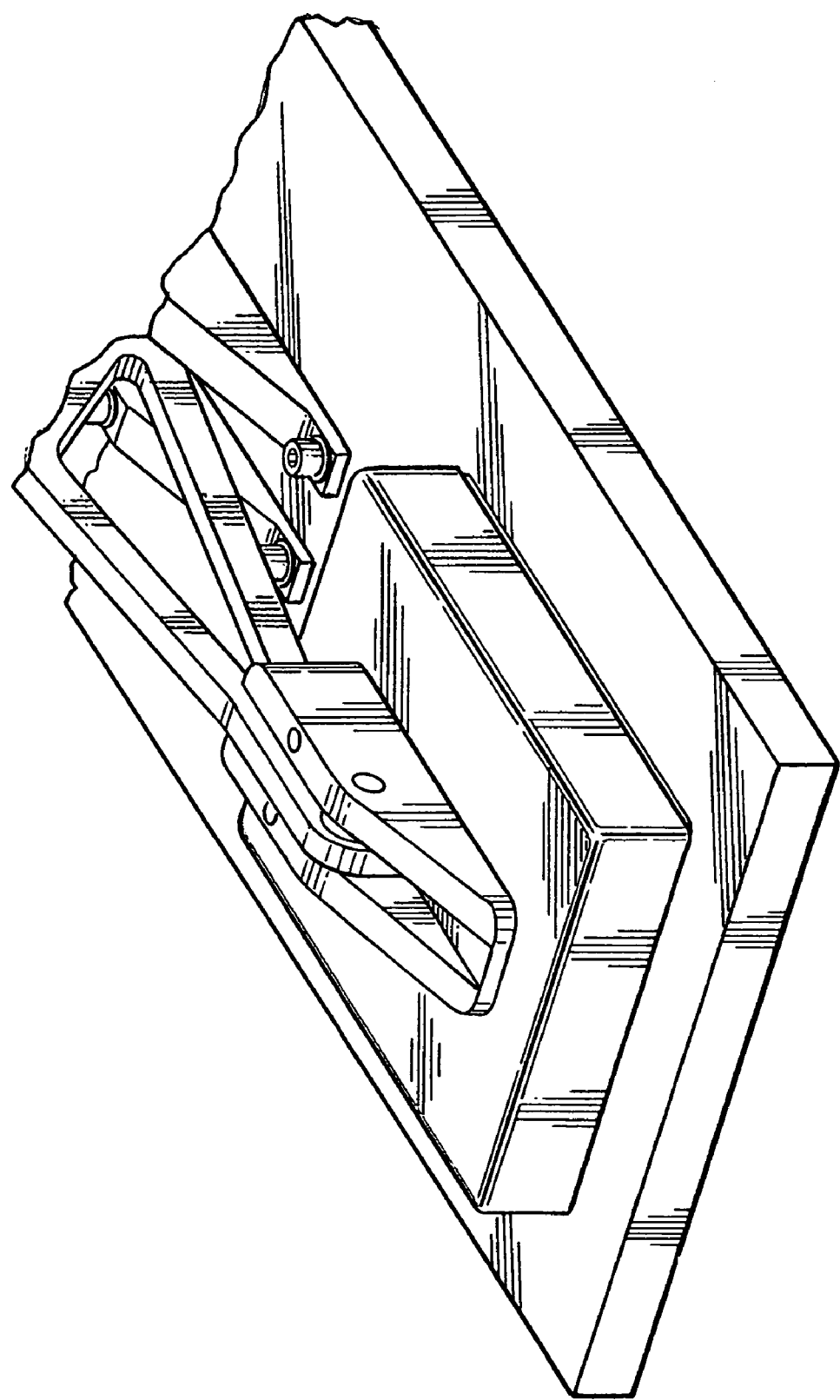
FIG. 12E depicts a close-up view of the platen of FIG. 12A.

FIGS. 12C and 12D provide side-views of charging station 1200 in both up and down positions, respectively. FIG. 12E depicts a close-up view of platen 1207 in a down position.

Figure 12F:
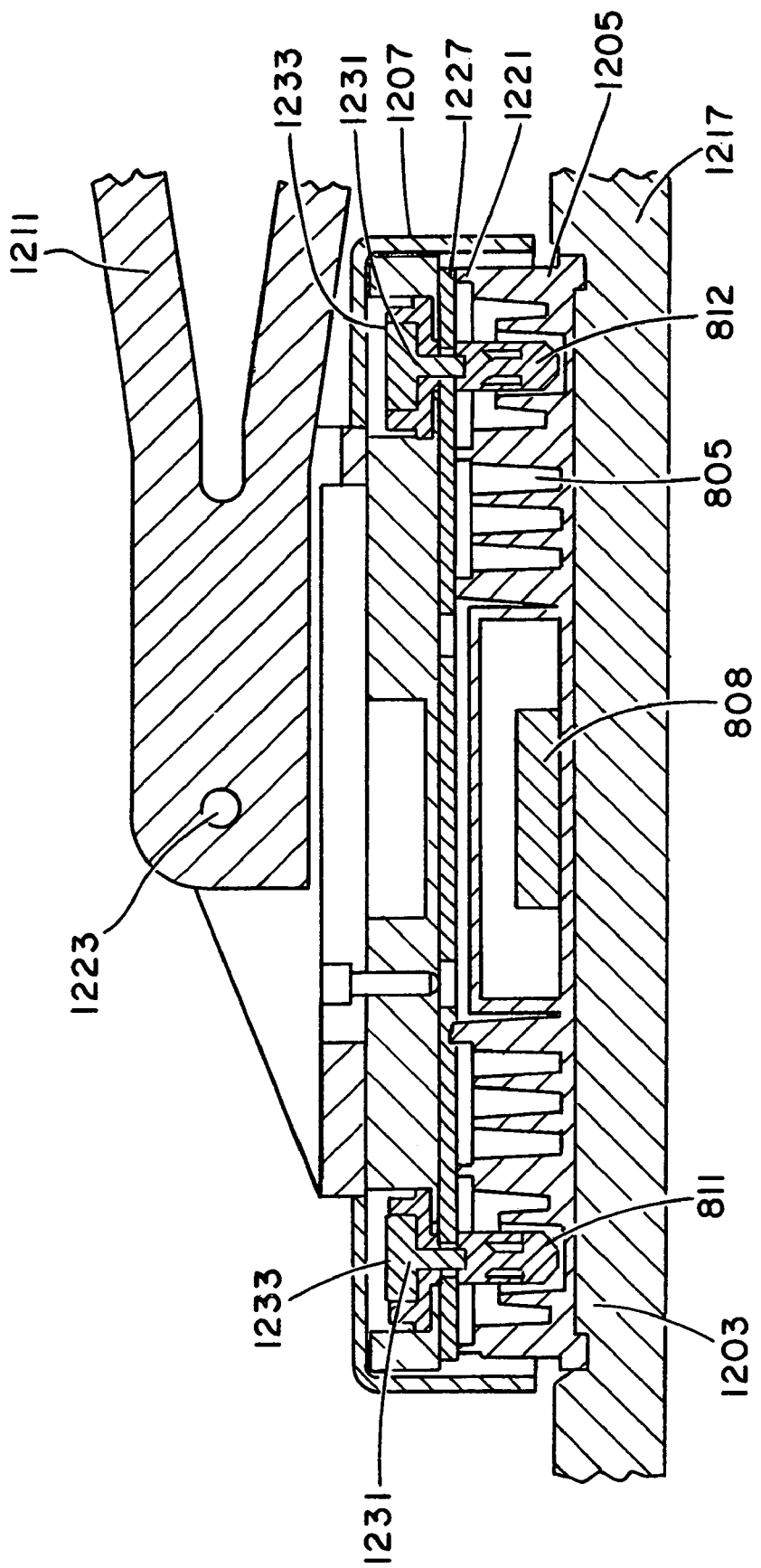
FIG. 12F depicts a cut-away side view of the platen of FIG. 12A.

FIG. 12F depicts a cut-away side-view of platen 1207 urged against upper face 1221 of microfluidic device 1205. Platen 1207 is urged against upper face 1221 of microfluidic device 1205 to form a fluid tight seal between microfluidic device 1205 and a platen face 1227, or between portions of device 1205 and face 1227. Platen face 1227, in one embodiment, includes or is made of a compliant material such as a resilient elastomer, preferably chemical resistant rubber or the like. Inside platen 1207 are separate fluid pressure lines, preferably gas pressure lines, which mate with various locations on upper face 1221 of microfluidic device 1205. Also shown are check valve purge actuators 1233 which are actuated, preferably pneumatically, and which when actuated, push a pin 1231 downward into check valve 812 to open and relieve fluid pressure, or permit the introduction of fluid through check valve 812 by overcoming its opening resistance. In one embodiment, platen 1207 has first and second purge actuators 1233 which engage check valves 811 and 812 (see FIG. 8B).

In another embodiment, chip or device 1205 is manufactured with normally closed containment and/or interface valves. In this embodiment, accumulators would not be necessary to hold valves shut during incubation. Pressure would be applied to carrier or device 1205 well regions when interface and/or containment valves are desired to be opened. For all or most other times, the valves would remain closed to separate the various chip experiments from one another, and/or to separate reagent and protein wells on the chip from one another.

Figure 12G:
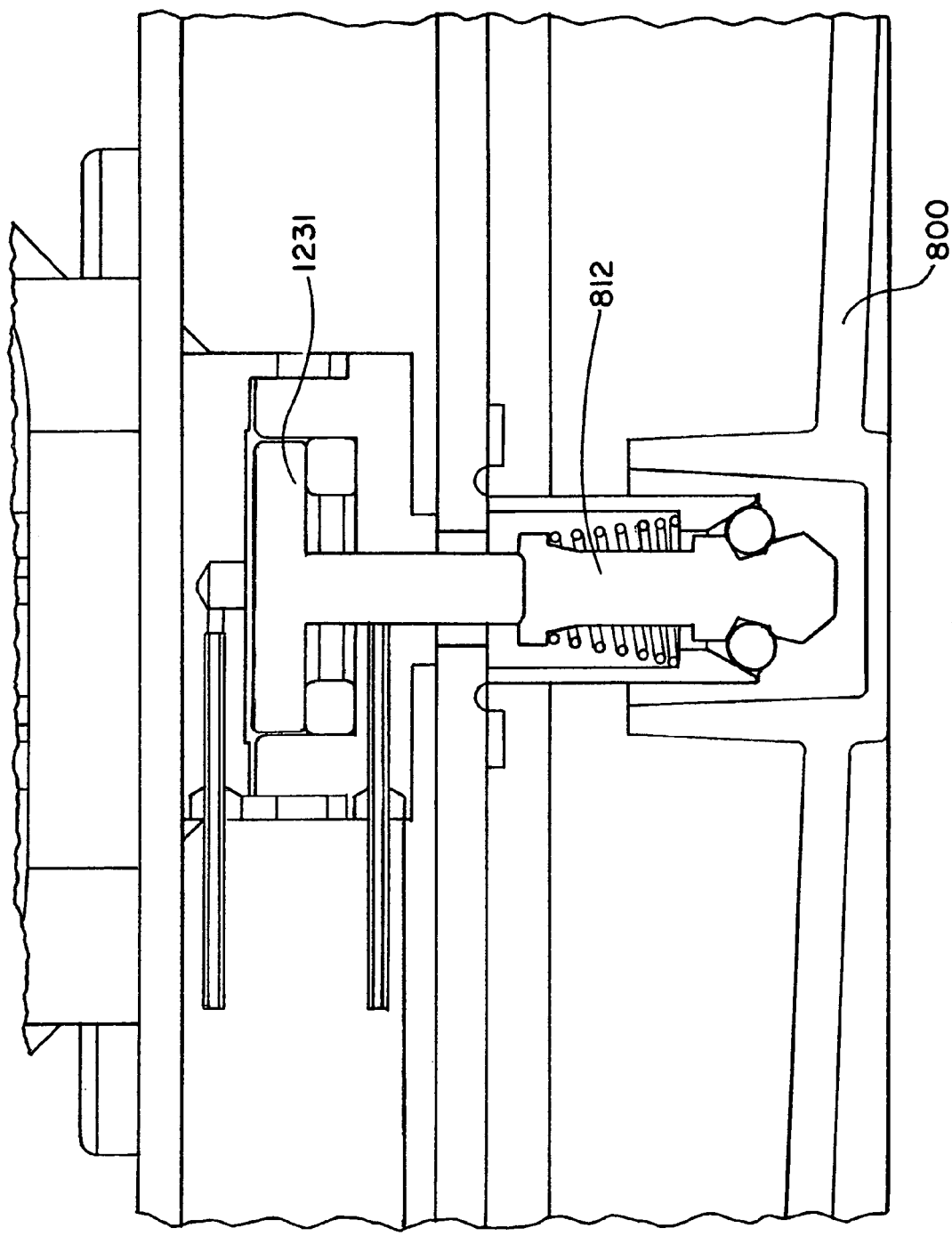
FIG. 12G is a close-up view of a purge actuator acting on a check valve according to an embodiment of the present invention.

FIG. 12G provides an extreme close-up view of purge actuator 1233 acting upon check valve 812 located within substrate 800 of microfluidic device 1205.

Figure 12H:
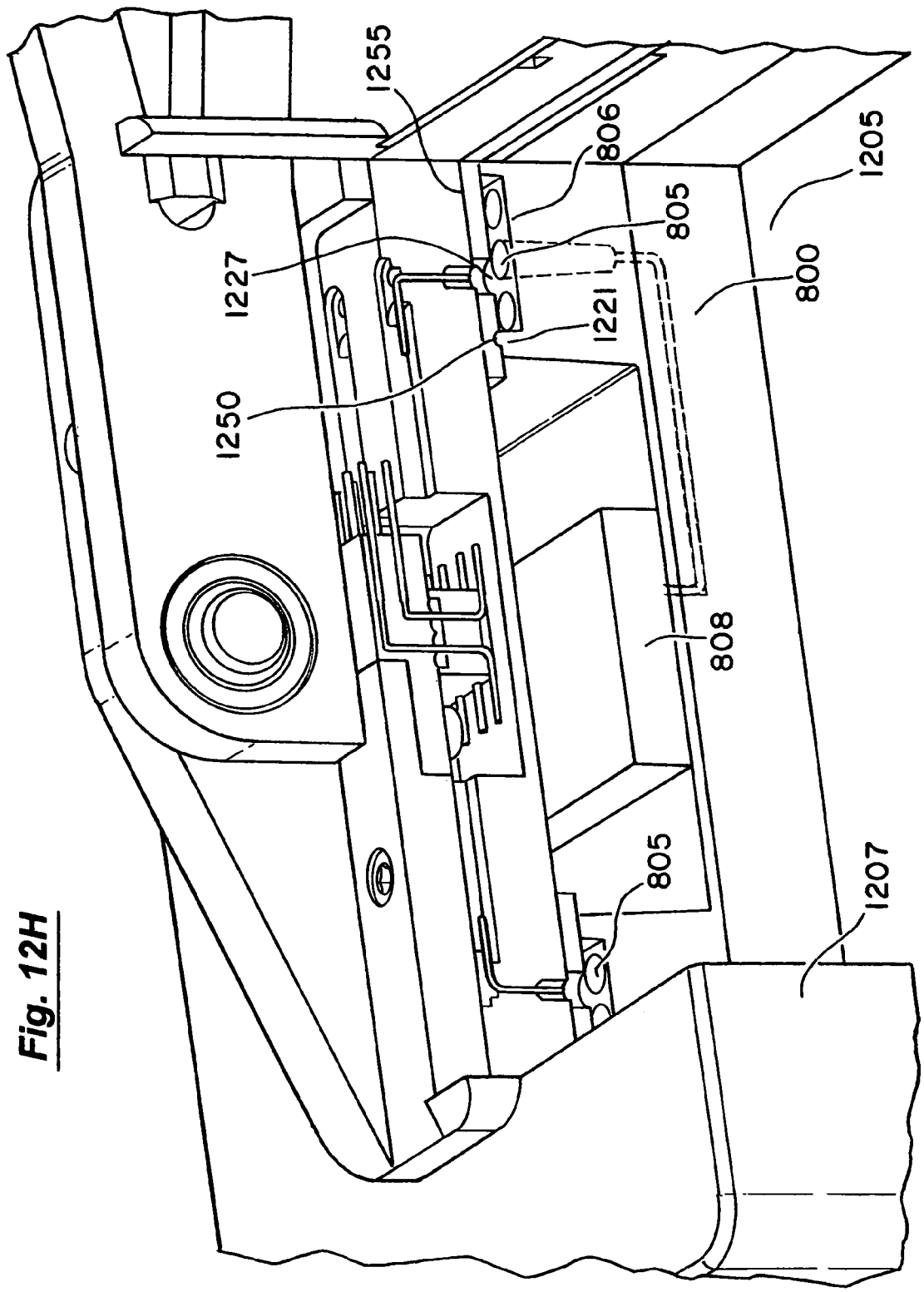
FIG. 12H depicts a cut-away view of a platen urged against the upper face of a microfluidic device according to an embodiment of the present invention.

FIG. 12H depicts a cut-away view of platen 1207 urged against upper face 1221 of microfluidic device 1205 wherein a pressure cavity 1255 is formed above well row 806 by contacting platen face 1227 against a ridge 1250 of upper face

1221. Fluid pressure, preferably gas pressure, is then applied to pressure cavity 1255 by introducing a fluid into cavity 1255 from pressure lines running down arm 1211 of charging station 1200. Pressure is regulated by pressure regulators associated with charging station 1200, preferably by electronically controlled variable pressure regulators that can change output pressure in accordance with signals sent by a charging station controller, preferably under computer control. Fluid pressure inside of pressure cavity 1255 in turn drives liquid within well 805 through the channels within substrate 800 and into channels and/or chambers of elastomeric block 808 to fill channels or chambers or to actuate a deflectable portion of elastomeric block 808, preferably a deflectable membrane valve as previously described.

FIG. 13 depicts a rear plan view of the fluidic routing within platen face 1227, and the spatial location of each fluid pressure port of platen face 1227 according to a particular embodiment of the present invention. In a particular embodiment, fluid interfaces of platen 1207 are positioned to be aligned with fluid ports, wells 805, check valves and the like when platen 1207 engages microfluidic device 1205. In a particular embodiment, microfluidic device 1205 is an integrated carrier and microfluidic chip such as the Topaz® 1.96 or Topaz® 4.96 chips.

Interrupted diffusion is believed to allow diffusion for a period of time sufficient to cause the smaller crystallizing agents to diffuse into the chamber containing protein while limiting the counter diffusion of proteins into the crystallization reagent chamber by closing the interface valve. The interface valve, when actuated, separates the chamber containing protein from the chamber containing crystallization reagent.

The present invention provides for devices, systems and methods for using such devices and systems, for holding and manipulating microfluidic devices, in particular, multilayer elastomeric microfluidic devices wherein at least one deflectable membrane acts as a valve to interrupt or separate fluid within a microfluidic channel having a cross-sectional dimension of about 500 micrometers. Exemplary microfluidic devices are used to screen for conditions which cause protein crystals to form from protein solutions by free-interface diffusion (FID). In use, the microfluidic devices are loaded with a protein solution and a crystallization agent, typically in the form of a reagent solution, wherein each solution enters into individual chambers interconnected by a channel having a valve therein. Containment valves are then used to keep each of the solutions in their respective chamber as the valve located in the channel separating the chambers is opened to initiate diffusion between the chambers. In preferred devices, the valves are actuated by changes in fluid pressure, for example either hydraulically or pneumatically. Therefore, a means for changing fluid pressure to each of the valve is helpful.

Figure 14A:
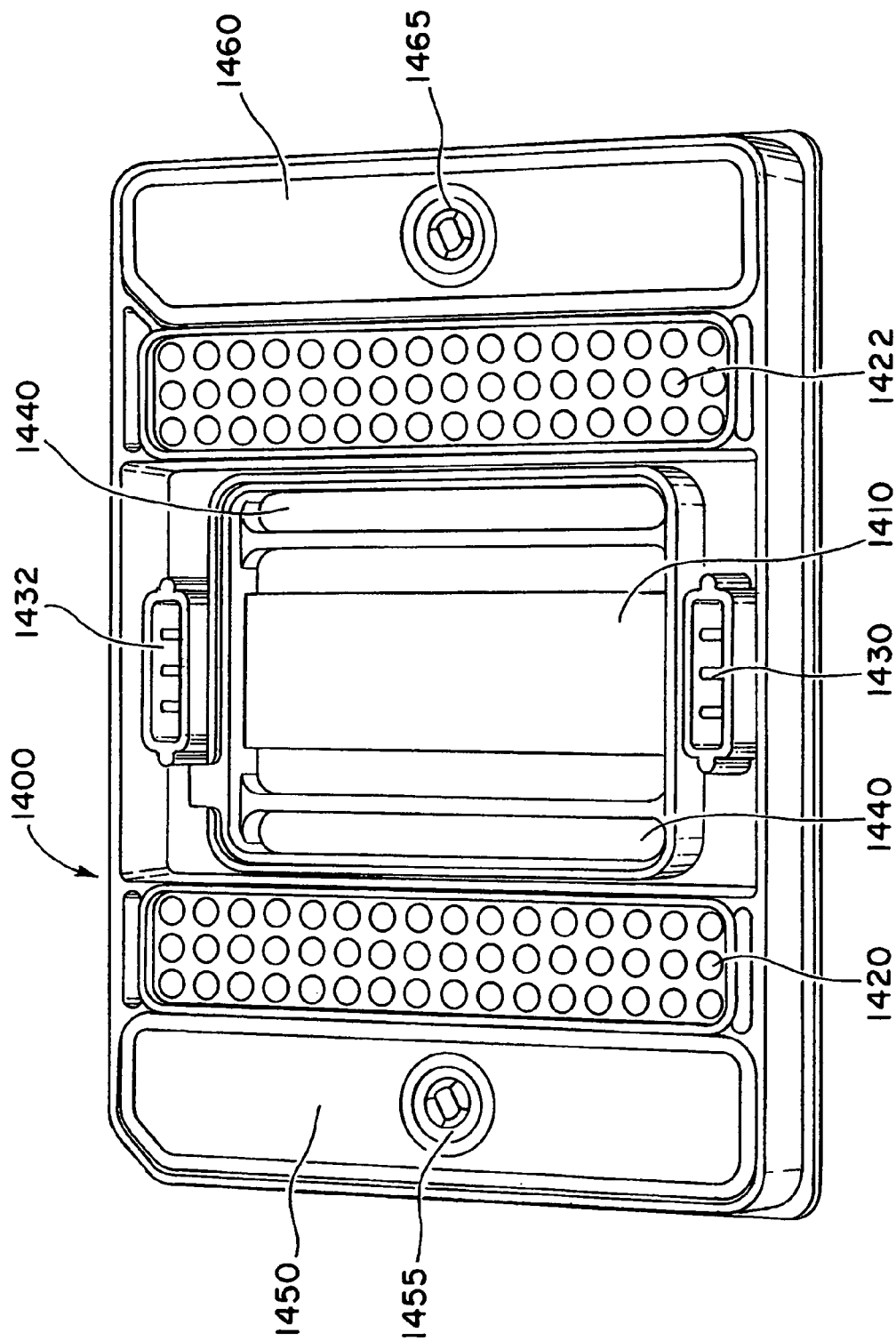
FIG. 14A is perspective view of a carrier in accordance with an embodiment of the present invention.

The invention provides, in one aspect, for a carrier that provides access to controlled fluid pressure. FIG. 14A depicts a perspective view of a preferred embodiment. The carrier in FIG. 14A, which in one embodiment has about a three inch square footprint and is about one inch in height, is preferably made from a polymer, preferably acrylic. Other materials may be used depending on the nature of the experiments to be performed using the carrier, and the solvents that the carrier may be exposed to during use. For example, a carrier could be made from polypropylene to provide resistance to certain solvents such as acetone.

Figure 14B:
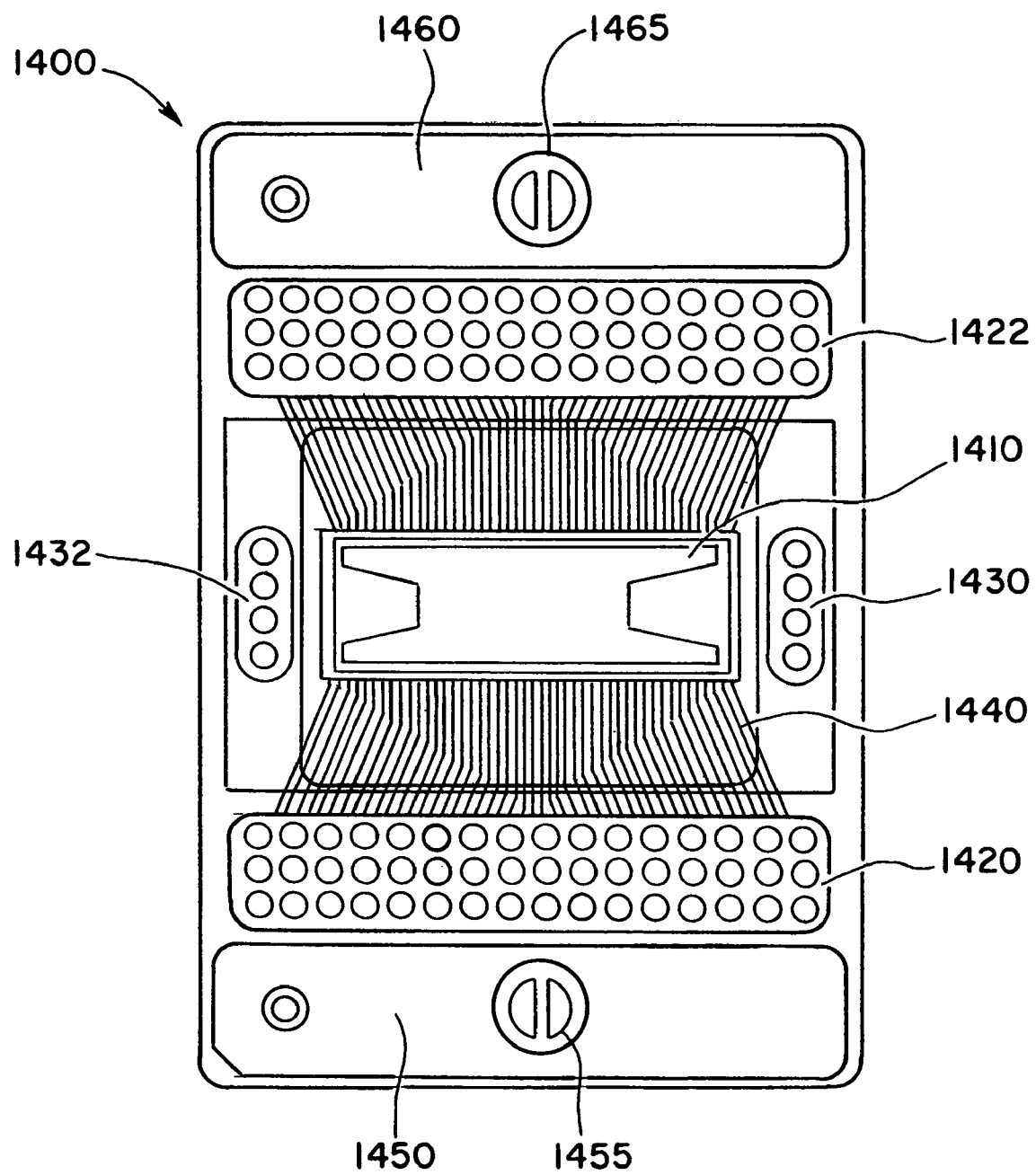
FIG. 14B is a top view of an integrated carrier and chip according to an embodiment of the present invention.

Turning now to FIGS. 14A and 14B a particular embodiment of the present invention will be described. FIG. 14A depicts a carrier 1400 adapted to receive a microfluidic device or chip (not shown in FIG. 14A), such as a chip used to grow protein crystals. The chip is mounted in carrier 1400, integrally formed with carrier 1400, or is a stand alone chip having similar size, features and functions as carrier 1400. In one embodiment, carrier 1400 includes a plurality of ports or wells that are in fluid communication with corresponding wells on the microfluidic device. In this manner, fluids provided to the carrier wells can in turn be delivered to the microfluidic device. Further, fluids disposed in the carrier or device wells can be delivered to testing regions within the device by applying pressure to the ports or wells on carrier 1400.

In a particular embodiment, the microfluidic device or chip is received in a chip region 1410 disposed in carrier 1400, or integrally formed therewith. In one embodiment, carrier 1400 includes a first well region 1420 and a second well region 1422 adapted to receive a plurality of reagents. In one embodiment, first well region 1420 and second well region 1422 are each adapted to receive up to forty-eight (48) reagents apiece. In one embodiment, regions 1420 and 1422 comprise a plurality of wells that are coupled to corresponding wells on the microfluidic device when the device is disposed within carrier 1400. This may occur, for example, using channels in carrier 1400 as previously described. In one embodiment, carrier 1400 further includes a first protein region 1430 and a second protein region 1432. First protein region 1430 includes a plurality of wells, and in a particular embodiment four wells or ports, adapted to receive desired proteins. In another embodiment, second protein region 1432 is adapted to receive up to four proteins. In a particular embodiment, second protein region 1432 provides vents for carrier 1400. In other embodiments, the number of wells vary from those noted herein for regions 1420, 1422, 1430 and 1432 depending on a wide range of factors including, without limitation, the desired number of experiments or tests, the desired well or crystal size, the carrier size, and the like.

In some embodiments it is desirable to control the humidity of the chip. In one embodiment, a hydration chamber 1440 is formed around the chip, with hydration chamber 1440 adapted to hold a fluid or a fluid source. In a particular embodiment, a sponge, a gel package, a woven material such as a piece of cloth or a cotton ball/pad, or other material adapted to hold a liquid is disposed within hydration chamber 1440. In a particular embodiment, fluid-containing material may be disposed on both sides of the chip as indicated in FIG. 14B. The sponge or other material may be hydrated with water, buffer, a crystallization reagent, or a solvent. Alternatively, a desiccating material may added to remove moisture from the microfluidic device. Carrier 1400 further includes an interface accumulator 1460 having a check valve 1465 and a containment accumulator 1450 having a check valve 1455. As previously described in conjunction with earlier embodiments, check valves 1455, 1465 are adapted to allow the increase or release of pressure within accumulators 1450 and 1460, to introduce or remove fluids from accumulators 1450 and 1460, and also to operate to maintain the pressure within carrier 1400, and thus to maintain or apply pressure to appropriate regions of the microfluidic device disposed therein. The advantage of having an "on-board" source of controlled fluid pressure is that the microfluidic device, if actuated by changes in fluid pressure, can be kept in an actuated state independent of an external source of fluid pressure, thus liberating the microfluidic device and carrier from an umbilical cord attached to that external source of fluid pressure. The accumulator may further include a gas pressurization inlet port, a liquid addition port, and a pressurized fluid outlet for communicating fluid pressure to the connection block.

Figure 15A:
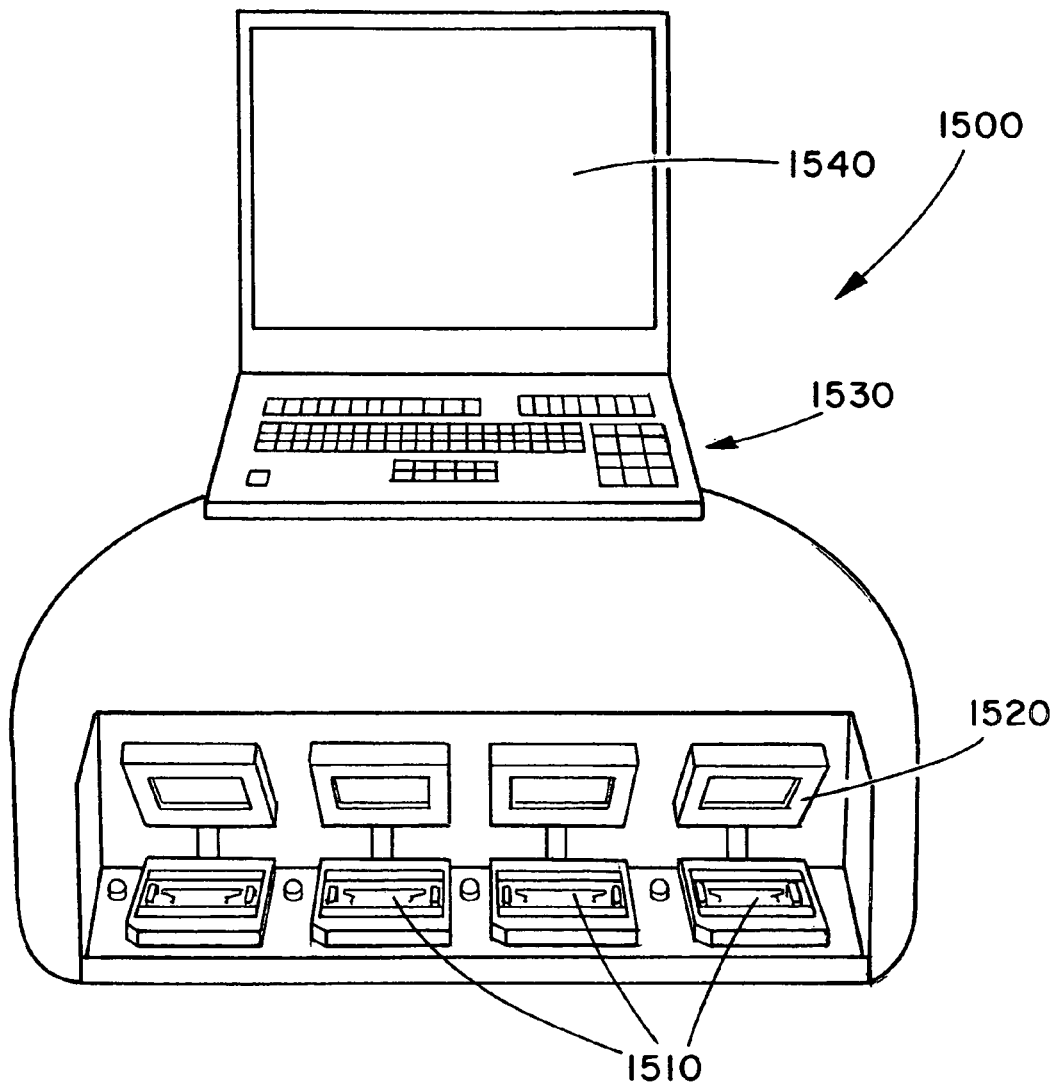
FIG. 15A is a simplified overall view of a system according to an embodiment of the present invention.
Figure 15B:
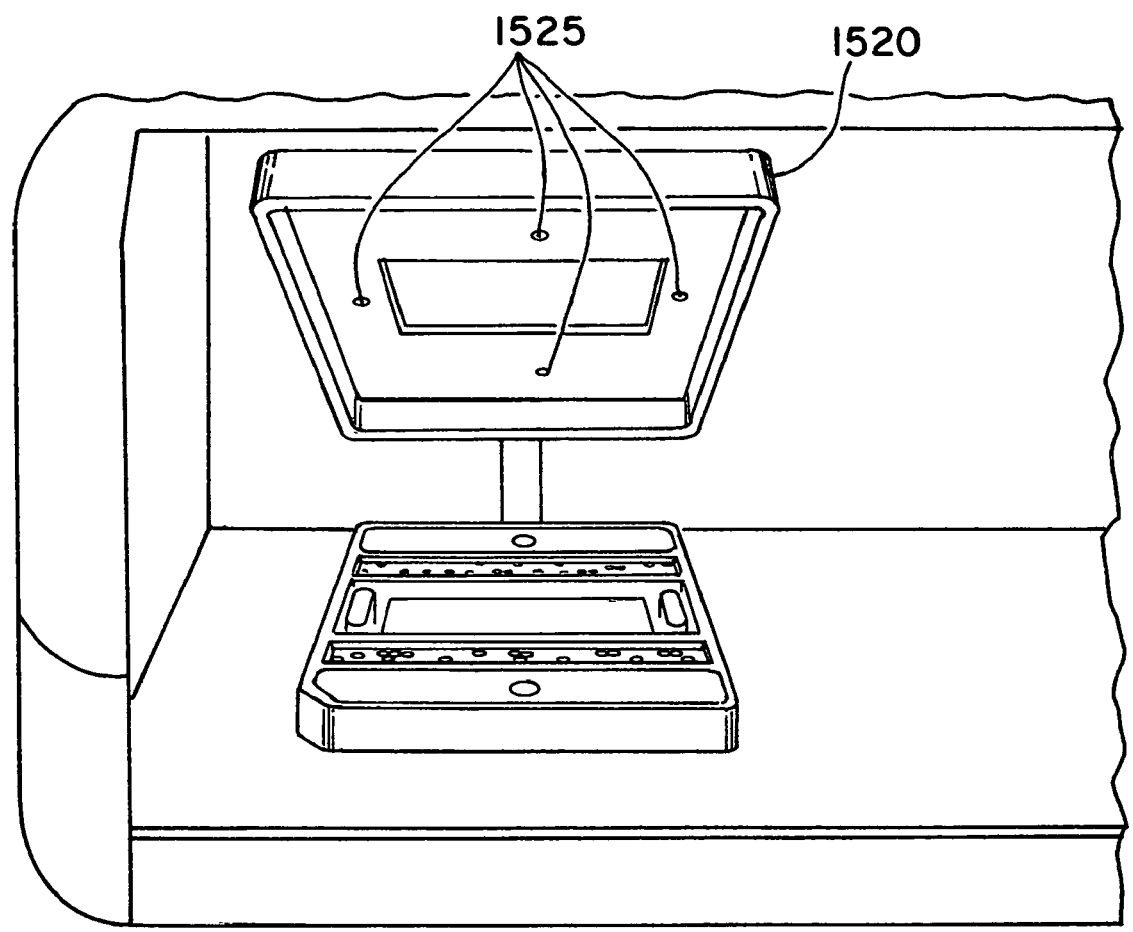
FIG. 15B is a perspective view of a receiving station in the system of FIG. 15A.

In a particular embodiment, the integrated carrier 1400 and microfluidic device are adapted for performing desired experiments according to embodiments of the present invention by using the systems of the present invention. More specifically, as shown in FIG. 15A, a system 1500 includes one or more receiving stations 1510 each adapted to receive a carrier 1400. In a particular embodiment, system 1500 includes four (4) receiving stations 1510, although fewer or a greater number of stations 1510 are provided in alternative embodiments of the present invention. FIG. 15B depicts carrier 1400 and a device in combination disposed in station 1510 under an interface plate 1520. Interface plate 1520 is adapted to translate downward in FIG. 15B so that interface plate 1520 engages the upper surface of carrier 1400 and its microfluidic device. In some embodiments, station 1510 and platen 1520 are similar to station 1200 and platen 1207. Interface plate 1520 includes one or more ports 1525 for coupling with regions in carrier 1400 which are adapted to receive fluids, pressure, or the like. In some embodiments, interface plate 1520 includes two ports, three ports, four ports, five ports, six ports, seven ports, eight ports, nine ports, ten ports, or the like. In a preferred embodiment, interface plate 1520 is coupled to six lines for providing pressure to desired regions of carrier 1400, and two lines for providing a mechanism for activating check valves 1455 and 1465.

Figure 15C:
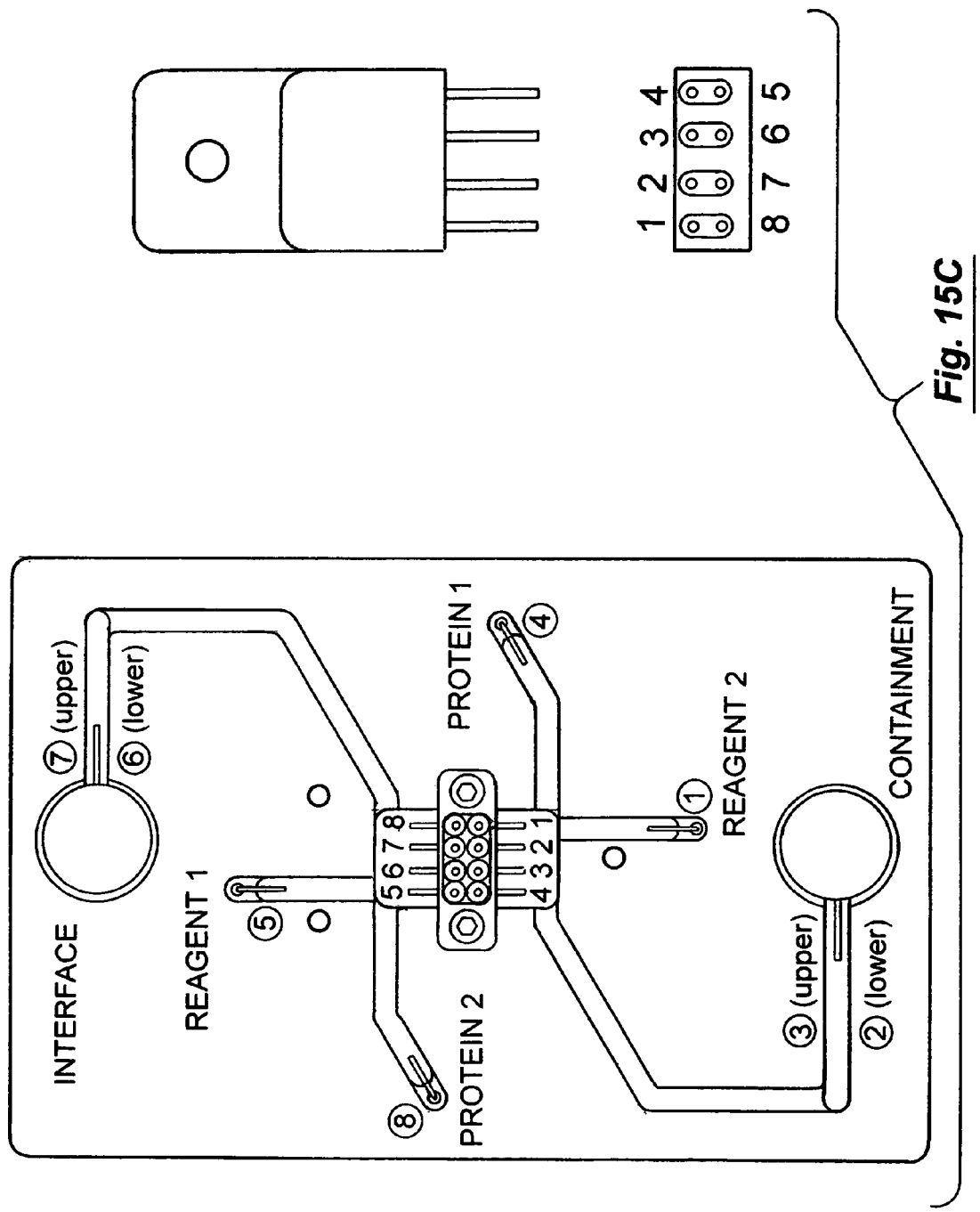
FIG. 15C is a rear plan view of fluidic routing within a plate interface or platen according to another embodiment of the present invention

FIG. 15C depicts various regions of interface plate 1520 according to a particular embodiment of the present invention, similar to FIG. 13. In alternative embodiments interface plate 1520 includes a different number or configuration of ports than those depicted in FIG. 15C.

Figure 17:
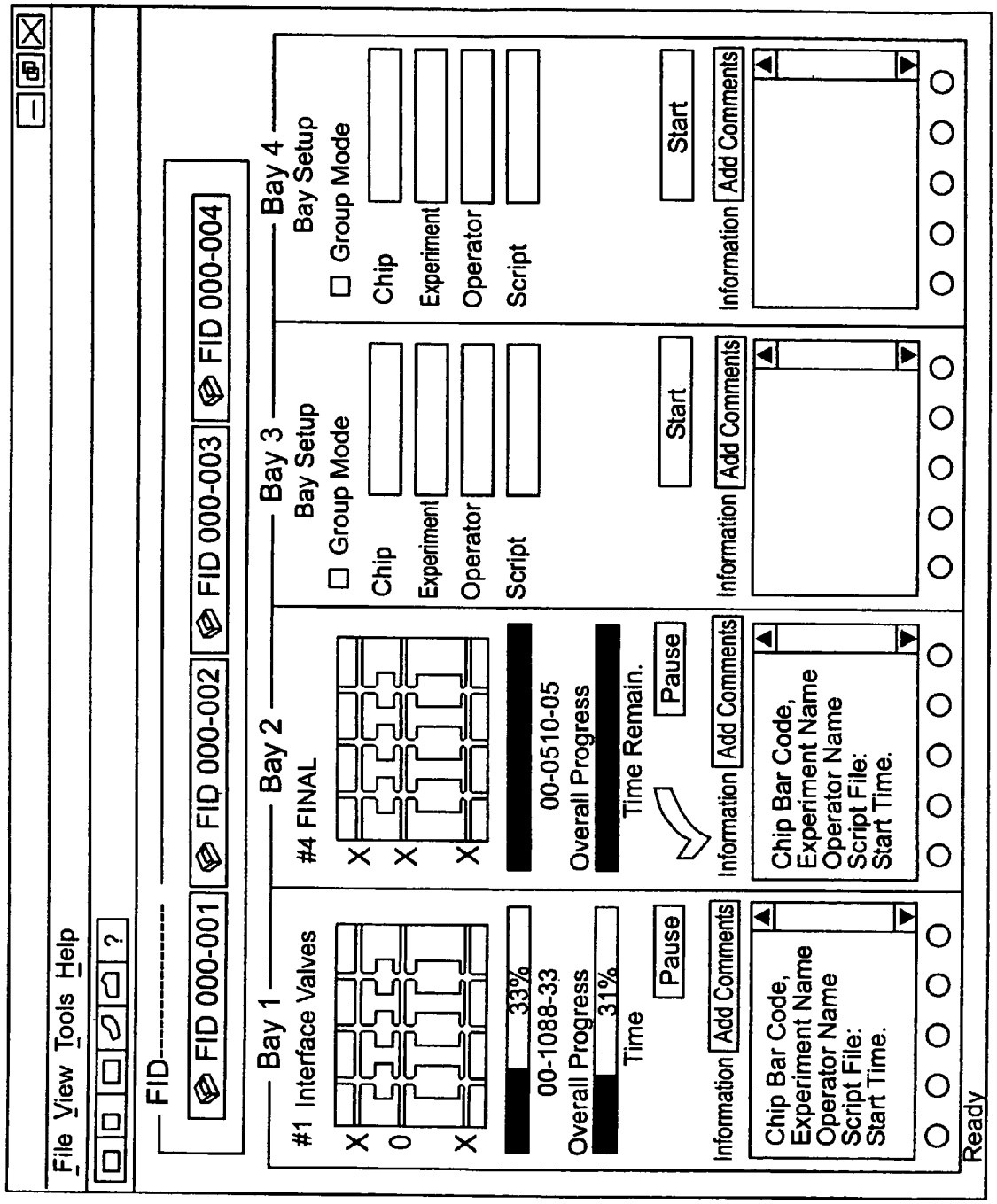
FIG. 17 is an example screen shot available with the system of FIG. 15A.

As shown in FIG. 15A, system 1500 further includes a processor that, in one embodiment, is a processor associated with a laptop computer or other computing device 1530. Computing device 1530 includes memory adapted to maintain software, scripts, and the like for performing desired processes of the present invention. Further, computing device 1530 includes a screen 1540 for depicting results of studies and analyses of microfluidic devices, with FIG. 17 depicting one embodiment of a screen shot for display on system 1500. System 1500 is coupled to one or more pressure sources, such as a pressurized fluid, gas, or the like, for delivering same to the microfluidic devices which are fluidly coupled to interface plate(s) 1520.

Figure 16A:
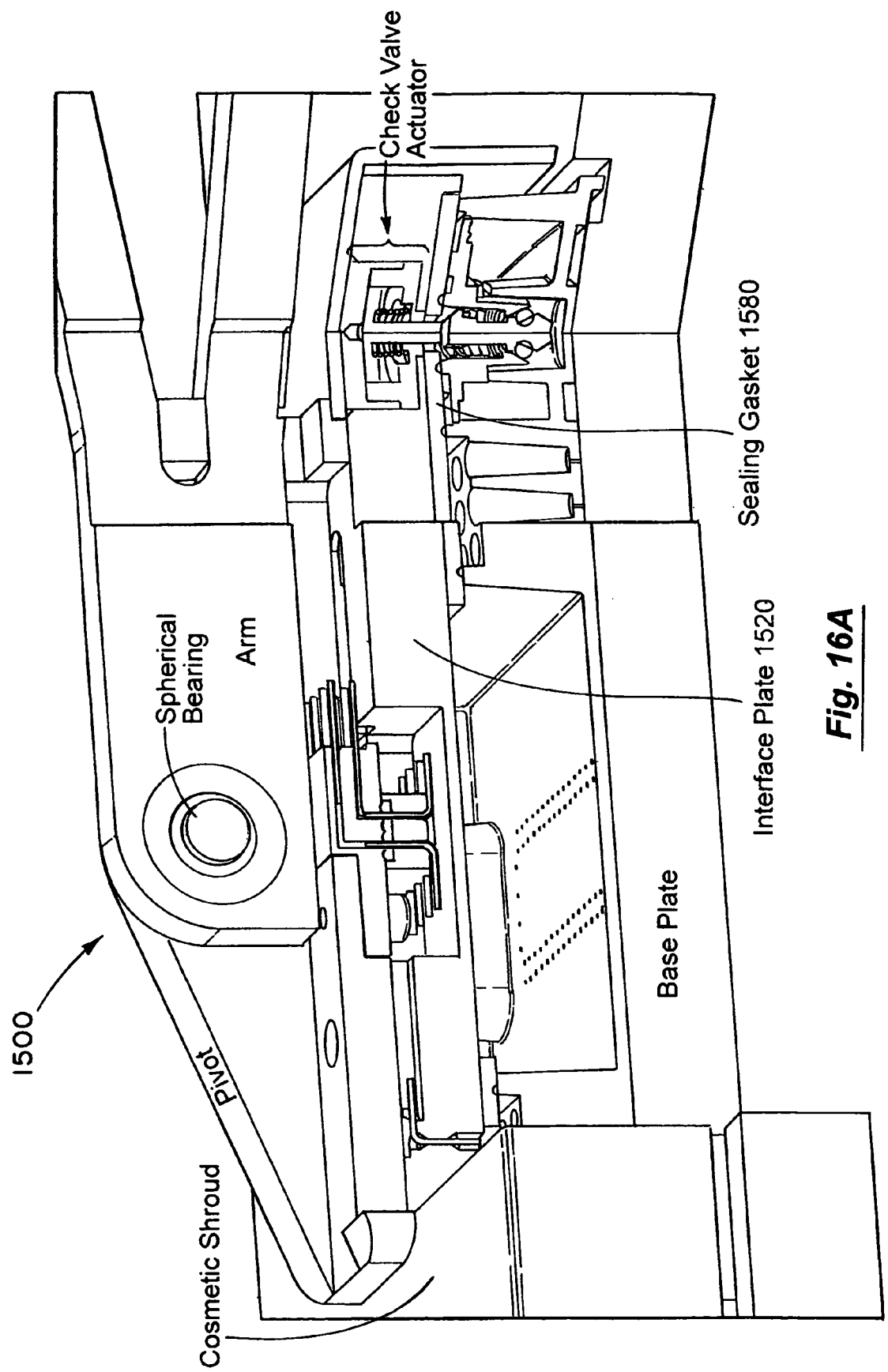
FIGS. 16A and 16B are cross sectional side views showing an interface plate mated to a carrier according to an embodiment of the present invention.
Figure 16B:
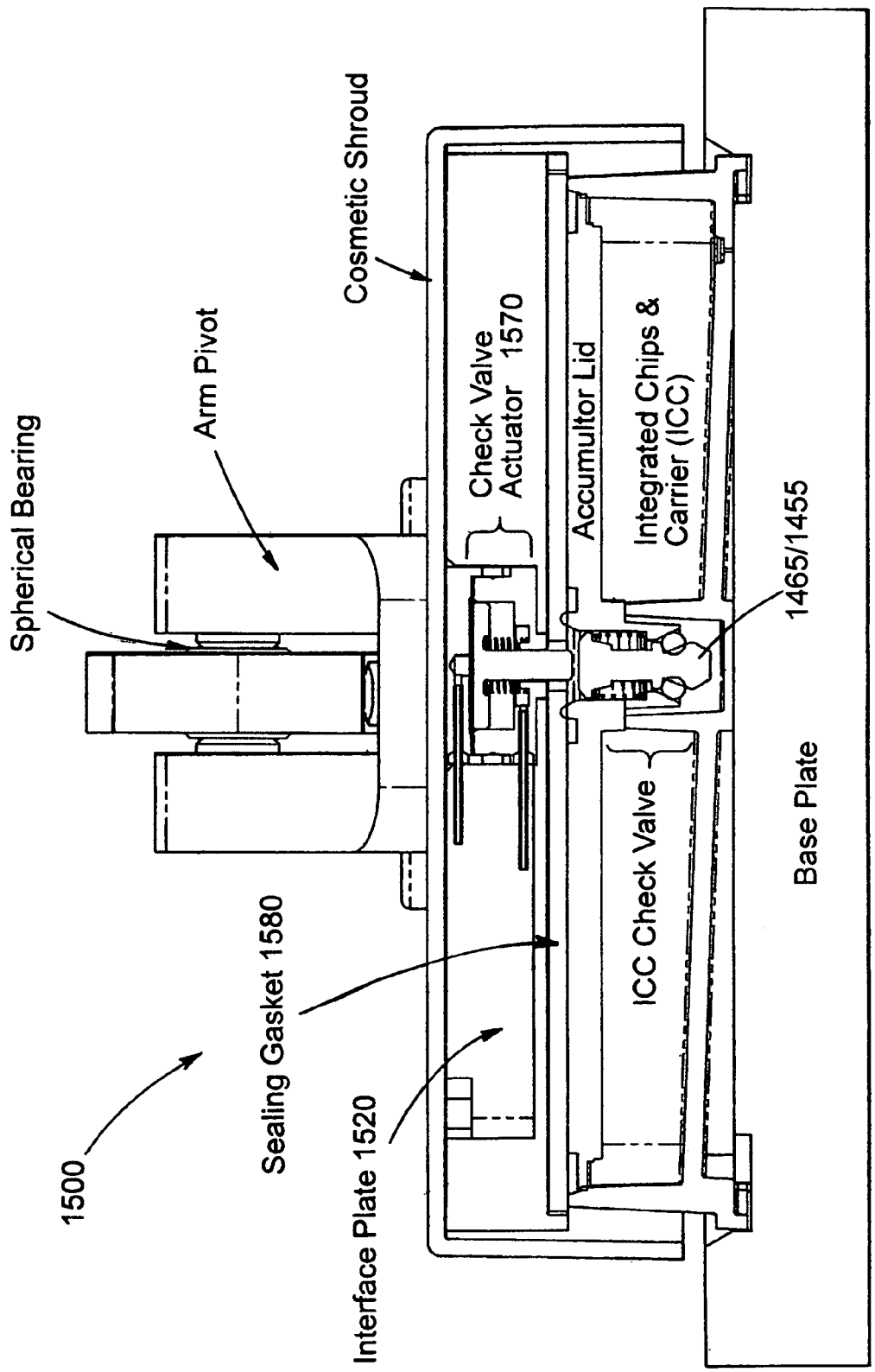

FIGS. 16A and 16B depict a particular embodiment of system 1500, and more specifically, of interface plate 1520. In FIG. 16A, interface plate 1520 is coupled to the integrated chip and carrier 1400 in a manner that fluidly seals certain regions thereof. In particular, fluid seals are provided between interface plate 1520 and one or more regions of carrier 1400 and chip, such as the first protein region 1430, second protein region 1432, first well region 1420, second well region 1422, interface accumulator 1460, check valve 1465, containment accumulator 1450, and/or check valve 1455. In one embodiment, interface plate 1520 provides fluid seals to regions 1420, 1422, 1430, 1432, and to accumulator 1450 and 1460. In one embodiment, interface plate 1520 provides one or more check valve actuators 1570 as best seen in FIG. 16B.

In some embodiments, interface plate 1520 provides all of the desired fluid seals to carrier 1400 and the microfluidic device. In doing so, interface plate 1520 may include a sealing gasket 1580. Sealing gasket 1580 may comprise a wide range of materials, including without limitation silicon rubber, an elastomer, or the like. In some embodiments, gasket 1580 comprises a compliant material to help form fluidic seals at the desired locations. In this manner, system 1500 can provide the desired pressures to appropriate regions of chip and carrier 1400. In other embodiments, interface plate 1520 is a two or more plate components. For example, the regions or ports on carrier 1400 and the microfluidic device each may be fluidly coupled to a separate plate 1520 adapted to fit that port or region. System 1500 then would include the necessary number of interface plates 1520 for the various ports or regions. Further, in some embodiments, more than one region or port is coupled to a particular interface plate 1520, while other regions or ports are coupled to a separate interface plate 1520. Other combinations of interface plates and carrier/chip regions and ports also fall within the scope of the present invention.

The operation of system 1500, in one embodiment, involves the loading of one or more carriers 1400 into receiving station(s) 1510. In some embodiments, carriers 1400 include the microfluidic device coupled thereto, and have desired reagents and proteins loaded into the carrier wells prior to placing the carriers into receiving stations 1510. In other embodiments, the carriers 1400 are placed into receiving stations 1510, and subsequently loaded with reagents and proteins. Carriers 1400 further may be loaded with a hydration fluid. Hydration fluid may be placed in hydration chamber 1440. After carriers 1400 are loaded into system 1500, interface plates 1520 are lowered or otherwise translated to engage carriers 1400. Plates 1520 may be manually, robotically, or otherwise lowered to fluidly seal with portions or all of chip/carrier 1400. A hydration fluid is provided to interface accumulator 1460 and/or containment accumulator 1450 and is driven into the chip by applying the appropriate pressure to accumulators 1450, 1460 using a pressure source coupled to interface plate 1520. In a particular embodiment, system 1500 automatically performs this process, which in a particular embodiment occurs within about twenty (20) hours after the hydration fluid is added to carrier 1400. As a result, the chip is sufficiently loaded with hydraulic fluid to operate chip containment and/or interface valves, as described herein and more fully in the patents and applications previously incorporated herein by reference.

The proteins and reagents are dispensed into the chip by applying the desired pressure to the appropriate sealed chip regions around the appropriate inlets. For example, applying a pressure between about 1 psi and about 35 psi to first and second well regions 1420 and 1422 operates to drive the reagents into the chip. Similarly, applying a pressure between about 1 psi and about 35 psi to first and second protein regions 1430, 1432 operates to drive the proteins into the chip. In a particular embodiment, this occurs within about sixty (60) minutes after loading the chip with hydraulic fluid. Once the proteins and reagents have been driven to the desired wells, chambers, reservoirs or the like within the chip, the interface valves within the chip are opened by releasing check valve 1465 in interface accumulator 1460. In a particular embodiment, check valve 1465 is released, to open interface valves in the chip, when system 1500 activates check valve actuator 1570 which engages check valve 1465. In some embodiments, check valve actuator 1570 includes a pin, a post, or the like adapted to engage check valve 1465 in order to release pressure within interface accumulator 1460. In an alternative embodiment, check valve 1465 is manually released or opened.

After the reagent and proteins are allowed to mix for a desired period of time, using free interface diffusion or other appropriate processes, the interface valves are closed. A pressure is applied to actuators 1450 and/or 1460 in order to maintain closed interface valves and containment valves. The carrier 1400 may be removed from system 1500 for incubation or storage. Actuators 1450 and 1460 hold the pressure for a desired period of time, from hours to days, in order to prevent or help prevent the containment and interface valves from opening. In a particular embodiment, actuators 1450 and 1460 maintain the pressure within the chip above a desired threshold pressure sufficient to keep containment and/or interface valves closed. In one embodiment, actuators 1450 and 1460 maintain the pressure above the threshold pressure for at least two (2) days, at least seven (7) days, and the like. The length of time actuators 1450 and 1460 maintain the desired pressure depends in part on the incubation temperature. Depending in part on the desired incubation period length and/or incubation conditions, carrier 1400 may be returned to system 1500 in order to recharge or repressurize actuators 1450, 1460. In this manner, the incubation period may be extended to help provide for desired crystal growth or other chemical or related processes.

FIG. 17 depicts a typical graphical user interface computer screen generated by a computer driving station 1510 as described above. In a preferred embodiment which is shown, four different charging stations can be actuated independently, as shown by the four separate screen columns indicating status. The software can be linked to a data input device and a database to correlate experimental conditions, reagents used, user identification, sample character, valve actuation profiles, humidity, and post reaction analysis data by associating a unique identifier, preferably a bar or spatial dot optical code or an encoded radio frequency device with a microfluidic device of the present invention. Information may be generated by different laboratory instruments, such as robotic dispensing stations, robotic plate handlers, incubators, charging stations as described herein, and optical inspection stations, such as those described in copending U.S. Provisional Patent Application Nos. 60/472,226 by Lee et al filed on May 20, 2003, 60/490,712 and 60/490,584, both by Taylor, and 60/490,666 by Quan, each of the three filed on Jul. 28, 2003 and are all commonly assigned to the assignee of the present application, and which are each herein incorporated by reference in their entireties for all purposes.

Software used to operate the charging stations described herein may further provide for an end-user script writing feature which allows an end user to write custom scripts to actuate and otherwise control or manipulate the microfluidic devices described herein. Such custom scripts may further integrate with other computer programs and computer controlled devices used in experiments involving the microfluidic devices of the present invention.

EXAMPLE 1

In a preferred embodiment, a protein crystallization reactions may be carried out by controlling diffusion by closing the interface valve after a period of time, for example, after 60 minutes. Table 1, below, highlights the steps for using an exemplary protein crystallization device of the invention in a manner for which diffusion is interrupted after a period of time.

TABLE 1

| Script Name | Time | Description |
| --- | --- | --- |
| 1_Prime | 1 min. | Fills interface and containment lines with control line fluid and closes control line valves. Allows a pause to inspect valve closure. The last step opens interface valves. Use to prepare 1.96 Chip for experiment setup and test accumulator pressurization. |
| 2_Load 1.96 | 20 min. | Closes containment valves, pressurizes reagent and protein blindfill up to containment valves, closes interface valves, opens containment valves, continues loading protein and reagent up to interface valve, closes containment valve. Chip is ready for T0 scan at end of script. |
| 2-5_Load | 120 min. | Merges 2_Load 1.96 with 5_Ctrld FID 60 min. Use in place of the two scripts. Use to blind fill reagents, begin diffusion, and then stop FID after to min. Use if T0 scan is not needed. |
| 2-52 4C Load | 100 min. | Merges 2_Load 1.96 5_2 4C Ctrld FID 100 min. Use in place of the two scripts Use at 4° C. after 1_Prime to load reagents and protein. Chip is ready for T0 scan at end of script. |
| 3_Reload 1.96 | 16 min. | Closes interface valves, pressurizes reagent and protein blindfill up to interface valves, closes containment valves. Use if wells are not completely filled at the end of the 2_Load 1.96 script. Chip is ready for T0 scan at end of script. |
| 2_53 13C Load | 100 min. | Merges 2_Load 1.96 5_2 13C Ctrld FID 80 min. Use in place of the two scripts. Use at 13° C. after 1_Prime to load reagents and protein. Chip is ready for T0 scan at end of script. |
| 4_Post T0 | 30 sec. | Opens interface valves to begin diffusion. Use after T0 scan. Chip is ready for incubation at end of script. |
| 5_Controlled FID 60 min | 60.5 min. | Opens interface valves to begin diffusion, then, after a 60-min. period of diffusion, closes interface valves and recharges containment accumulator. Use after T0 scan as an alternative to 4_Post T0 to begin diffusion and then interrupt FID after |

TABLE 1-continued

| Script Name | Time | Description |
| --- | --- | --- |
| | | 60 min. |
| 5__2 4C Ctrld FID 100 min | 100 min. | Opens interface valves to begin diffusion. After a 100-min. period of diffusion, closes interface valves and recharges containment accumulator. Use at 4° C. after T0 scan as an alternative to 4__Post T0 to begin diffusion and then interrupt FID after 100 min. |
| 5__2 13C Ctrld FID 80 min | 80 min. | Opens interface valves to begin diffusion. After a 80-min. period of diffusion, closes interface valves and recharges containment accumulator. Use at 4° C. after T0 scan as an alternative to 4__Post T0 to begin diffusion and then interrupt FID after 80 min. |
| 5__2__4C Ctrld FID | 2.5 hr. | Opens interface valves to begin diffusion, then, after a 90-min. period of diffusion, closes interface valves and recharges containment accumulator. Use at 4° C., after T0 scan as to begin diffusion and then interrupt FID after 60 min. |
| 5__3__13C Ctrld FID | 2 hr. | Opens interface valves to begin diffusion, then, after a 90-min. period of diffusion, closes interface valves and recharges containment accumulator. Use at 4° C., after T0 scan as to begin diffusion and then interrupt FID after 90 min. |
| 6__Recharge | 30 sec. | Recharges interface and containment accumulator. Use every 24 hr. during incubation. |

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. For example, in addition to pressure based actuation systems described above, optional electrostatic and magnetic actuation systems are also contemplated. It is also possible to actuate the device by causing a fluid flow in the control channel based upon the application of thermal energy, either by thermal expansion or by production of gas from liquid. Further, in another embodiment, centrifugal force are used to drive protein and reagents into the chip. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention, but that the invention will include all embodiments and equivalents falling within the scope of the claims.

The disclosure set forth above may encompass one or more distinct inventions, with independent utility. Each of these inventions has been disclosed in its preferred form(s). These preferred forms, including the specific embodiments thereof as disclosed and illustrated herein, are not intended to be considered in a limiting sense, because numerous variations are possible. The subject matter of the inventions includes all novel and nonobvious combinations and subcombinations of the various elements, features, functions, and/or properties disclosed herein.

What is claimed is:

1. An apparatus for operating a microfluidic device, comprising a carrier portion, the apparatus comprising:
a platen having a platen face with one or more fluid ports therein and one or more check valve purge actuators, the fluid ports spatially corresponding to one or more inlets on a surface of the carrier portion of the microfluidic device and the one or more check valve purge actuators comprising one or more pins;
a platform for holding the microfluidic device relative to the platen;
a platen actuator for urging the platen against the microfluidic device so that at least one of the fluid ports of the platen is urged against one of the inlets to form a pressure chamber comprising the inlet and the port, so that when pressurized fluid is introduced or removed into or from the pressure chamber though one of the ports, fluid pressure is changed therein; and
a fluid line in fluid communication with at least a portion of the platen actuator, wherein the fluid line is configured to deliver a pressurized fluid to at least one of the fluid ports.

2. The apparatus as in claim 1 wherein the platen actuator comprises a robotic platen actuator.

3. The apparatus as in claim 2 wherein the platen actuator is under electronic control by a controller.

4. The apparatus as in claim 3 wherein the controller is a computer or under computer control.

5. The apparatus as in claim 4 wherein the computer is following a program.

6. The apparatus as in claim 5 wherein the program was customized by a user of the apparatus.

7. The apparatus as in claim 1, wherein the fluid line is configured to deliver the pressurized fluid to the at least one fluid pressure port using a pressure between about one (1) psi and about thirty-five (35) psi.

8. The apparatus as in claim 7, wherein the pressurized fluid is a gas.

9. The apparatus as in claim 8, wherein the gas is air.

10. An apparatus for operating a microfluidic device comprising a carrier portion, the apparatus comprising:
a platen having a platen face with a plurality of fluid ports therein and one or more check valve purge actuators, the fluid ports spatially corresponding to one or more inlets on a surface of the carrier portion of the microfluidic device and the one or more check valve purge actuators comprising one or more pins;

a platform for holding the micrOfluidic device relative to the platen; and a platen actuator for urging the platen against the microfluidic device so that at least one of the fluid ports of the platen is urged against one of the inlets to form a pressure chamber comprising the inlet and the port, so that when pressurized fluid is introduced or removed into or from the pressure chamber through one of the ports, fluid pressure is changed therein, and wherein the platen actuator is configured to deliver a pressurized fluid to the at least one fluid pressure port using a pressure between about one (1) psi and about thirty-five (35) psi.

11. The apparatus as in claim 10, wherein the pressurized fluid is a gas.

12. The apparatus as in claim 11, wherein the gas is air.

* * * * *